US008192390B2

(12) United States Patent
Hood et al.

(10) Patent No.: US 8,192,390 B2
(45) Date of Patent: Jun. 5, 2012

(54) METHOD AND SYSTEM FOR CONTROL OF OSMOTIC PUMP DEVICE

(75) Inventors: Leroy E. Hood, Seattle, WA (US); Muriel Y. Ishikawa, Livermore, CA (US); Edward K. Y. Jung, Bellevue, WA (US); Robert Langer, Newton, MA (US); Clarence T. Tegreene, Bellevue, WA (US); Lowell L. Wood, Jr., Livermore, CA (US); Victoria Y. H. Wood, Livermore, CA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 870 days.

(21) Appl. No.: 12/229,352

(22) Filed: Aug. 22, 2008

(65) Prior Publication Data
US 2009/0018704 A1 Jan. 15, 2009

Related U.S. Application Data

(62) Division of application No. 11/302,450, filed on Dec. 13, 2005, now Pat. No. 7,699,834.

(51) Int. Cl.
*A61N 1/30* (2006.01)
(52) U.S. Cl. ........................................................ 604/19
(58) Field of Classification Search ............... 604/890.1, 604/891.1, 892.1, 65–67, 131; 128/DIG. 12, 128/DIG. 13
See application file for complete search history.

(56) References Cited

U.S. PATENT DOCUMENTS

| 3,760,806 | A | 9/1973 | Leeper |
|---|---|---|---|
| 3,923,426 | A | 12/1975 | Theeuwes |
| 4,053,952 | A | 10/1977 | Goldstein |
| 4,263,910 | A | 4/1981 | Pardekooper et al. |
| 4,360,019 | A | 11/1982 | Portner et al. |
| 4,373,527 | A | 2/1983 | Fischell |
| 4,457,752 | A | 7/1984 | Vadasz |
| 4,513,034 | A | 4/1985 | Sparer et al. |
| 4,579,837 | A | 4/1986 | Busch et al. |
| 4,642,230 | A | 2/1987 | Whitehead et al. |
| 4,692,147 | A | 9/1987 | Duggan |
| 4,714,462 | A | 12/1987 | DiDomenico |
| 4,753,636 | A | 6/1988 | Free |
| 4,779,806 | A | 10/1988 | Langer et al. |
| 4,787,888 | A | 11/1988 | Fox |
| 4,834,704 | A | 5/1989 | Reinicke |

(Continued)

FOREIGN PATENT DOCUMENTS

JP 60118289 A 6/1985
(Continued)

OTHER PUBLICATIONS

UK Intellectual Property Office Examination Report Under Section 18(3); App. No. GB0921925.4; Jun. 9, 2011; pp. 1-5.

(Continued)

*Primary Examiner* — Manuel Mendez

(57) ABSTRACT

Embodiments of a system including a remotely controlled osmotic pump device and associated controller are described. Methods of use and control of the device are also disclosed. According to some embodiments, an osmotic pump device is placed in an environment in order to pump a material into the environment or into an additional fluid handling structure within the osmotic pump device. Exemplary environments include a body of an organism, a body of water, or an enclosed volume of a fluid. In selected embodiments, a magnetic field, an electric field, or electromagnetic control signal may be used.

28 Claims, 33 Drawing Sheets

U.S. PATENT DOCUMENTS

| | | |
|---|---|---|
| 4,861,484 A | 8/1989 | Lichtin et al. |
| 4,883,666 A | 11/1989 | Sabel et al. |
| 4,929,233 A | 5/1990 | Roth et al. |
| 4,944,659 A | 7/1990 | Labbe et al. |
| 4,952,406 A | 8/1990 | Brown et al. |
| 5,019,372 A | 5/1991 | Folkman et al. |
| 5,045,082 A | 9/1991 | Ayer et al. |
| 5,049,141 A | 9/1991 | Olive |
| 5,059,175 A | 10/1991 | Hanover et al. |
| 5,167,625 A | 12/1992 | Jacobsen et al. |
| 5,170,801 A | 12/1992 | Casper et al. |
| 5,207,666 A | 5/1993 | Idriss et al. |
| 5,217,449 A | 6/1993 | Yuda et al. |
| 5,279,607 A | 1/1994 | Schentag et al. |
| 5,370,611 A | 12/1994 | Niezink et al. |
| 5,370,672 A | 12/1994 | Fowler et al. |
| 5,391,164 A * | 2/1995 | Giampapa ............... 604/891.1 |
| 5,395,366 A | 3/1995 | D'Andrea et al. |
| 5,484,403 A | 1/1996 | Yoakum et al. |
| 5,505,706 A | 4/1996 | Maus et al. |
| 5,523,746 A | 6/1996 | Gallagher |
| 5,643,246 A | 7/1997 | Leeb et al. |
| 5,644,177 A | 7/1997 | Guckel et al. |
| 5,651,979 A * | 7/1997 | Ron et al. ............... 424/423 |
| 5,655,539 A | 8/1997 | Wang et al. |
| 5,666,977 A | 9/1997 | Higgins et al. |
| 5,667,504 A | 9/1997 | Baumann et al. |
| 5,698,220 A | 12/1997 | Cardinal et al. |
| 5,719,296 A | 2/1998 | Acton, III et al. |
| 5,733,313 A | 3/1998 | Barreras, Sr. et al. |
| 5,770,222 A | 6/1998 | Unger et al. |
| 5,797,898 A | 8/1998 | Santini, Jr. et al. |
| 5,800,420 A | 9/1998 | Gross et al. |
| 5,814,599 A | 9/1998 | Mitragotri et al. |
| 5,827,186 A | 10/1998 | Chen et al. |
| 5,830,207 A | 11/1998 | Leeb et al. |
| 5,869,078 A | 2/1999 | Baudino |
| 5,879,329 A | 3/1999 | Ginsburg |
| 5,928,195 A | 7/1999 | Malamud et al. |
| 5,935,593 A | 8/1999 | Ron et al. |
| 5,945,762 A | 8/1999 | Chen et al. |
| 5,993,414 A | 11/1999 | Haller |
| 6,048,328 A | 4/2000 | Haller et al. |
| 6,048,734 A | 4/2000 | Burns et al. |
| 6,077,837 A | 6/2000 | Kozak |
| 6,086,582 A * | 7/2000 | Altman et al. ............... 606/41 |
| 6,116,863 A | 9/2000 | Ahn et al. |
| 6,122,536 A | 9/2000 | Sun et al. |
| 6,146,103 A | 11/2000 | Lee et al. |
| 6,152,181 A | 11/2000 | Wapner et al. |
| 6,198,950 B1 | 3/2001 | Kraus |
| 6,198,963 B1 | 3/2001 | Haim et al. |
| 6,203,523 B1 | 3/2001 | Haller et al. |
| 6,206,914 B1 | 3/2001 | Soykan et al. |
| 6,261,584 B1 | 7/2001 | Peery et al. |
| 6,269,340 B1 | 7/2001 | Ford et al. |
| 6,270,680 B1 | 8/2001 | Silveri et al. |
| 6,272,370 B1 | 8/2001 | Gillies et al. |
| 6,312,393 B1 | 11/2001 | Abreu |
| 6,339,897 B1 | 1/2002 | Hayes et al. |
| 6,358,247 B1 * | 3/2002 | Altman et al. ............... 606/41 |
| 6,395,292 B2 | 5/2002 | Peery et al. |
| 6,408,878 B2 | 6/2002 | Unger et al. |
| 6,416,495 B1 | 7/2002 | Kriesel et al. |
| 6,436,069 B1 | 8/2002 | Jellie |
| 6,454,759 B2 | 9/2002 | Krulevitch et al. |
| 6,458,118 B1 | 10/2002 | Lent et al. |
| 6,464,687 B1 | 10/2002 | Ishikawa et al. |
| 6,475,750 B1 | 11/2002 | Han et al. |
| 6,491,061 B1 | 12/2002 | Lopez et al. |
| 6,491,684 B1 | 12/2002 | Joshi et al. |
| 6,500,165 B1 | 12/2002 | Frank |
| 6,500,168 B1 | 12/2002 | Jellie |
| 6,511,473 B2 | 1/2003 | Bartha et al. |
| 6,537,256 B2 | 3/2003 | Santini, Jr. et al. |
| 6,544,193 B2 | 4/2003 | Abreu |
| 6,554,822 B1 | 4/2003 | Holschneider et al. |
| 6,562,000 B2 * | 5/2003 | Thompson et al. ............... 604/48 |
| 6,565,526 B2 | 5/2003 | Seward |
| 6,569,152 B2 | 5/2003 | Brines et al. |
| 6,571,125 B2 | 5/2003 | Thompson |
| 6,585,763 B1 | 7/2003 | Keilman et al. |
| 6,589,205 B1 | 7/2003 | Meadows |
| 6,590,267 B1 | 7/2003 | Goodwin-Johansson et al. |
| 6,607,553 B1 | 8/2003 | Healy et al. |
| 6,615,855 B2 | 9/2003 | Lopez et al. |
| 6,628,989 B1 | 9/2003 | Penner et al. |
| 6,632,216 B2 | 10/2003 | Houzego et al. |
| 6,635,837 B2 | 10/2003 | Subramanian et al. |
| 6,653,124 B1 | 11/2003 | Freeman |
| 6,663,821 B2 | 12/2003 | Seward |
| 6,669,683 B2 | 12/2003 | Santini, Jr. et al. |
| 6,682,521 B2 | 1/2004 | Petrakis |
| 6,719,449 B1 | 4/2004 | Laugharn, Jr. et al. |
| 6,720,402 B2 | 4/2004 | Langer et al. |
| 6,723,086 B2 | 4/2004 | Bassuk et al. |
| 6,755,621 B2 | 6/2004 | Lopez et al. |
| 6,761,420 B2 | 7/2004 | Maluf et al. |
| 6,768,425 B2 | 7/2004 | Flaherty et al. |
| 6,768,920 B2 | 7/2004 | Lange et al. |
| 6,773,429 B2 | 8/2004 | Sheppard, Jr. et al. |
| 6,793,753 B2 | 9/2004 | Unger et al. |
| 6,796,956 B2 | 9/2004 | Hartlaub et al. |
| 6,802,489 B2 | 10/2004 | Marr et al. |
| 6,802,811 B1 | 10/2004 | Slepian |
| 6,805,783 B2 * | 10/2004 | Ohkawa ............... 204/454 |
| 6,808,522 B2 | 10/2004 | Richards et al. |
| 6,824,561 B2 | 11/2004 | Soykan et al. |
| 6,830,936 B2 | 12/2004 | Anderson et al. |
| 6,845,267 B2 | 1/2005 | Harrison et al. |
| 6,849,463 B2 | 2/2005 | Santini, Jr. et al. |
| 6,929,636 B1 | 8/2005 | von Alten |
| 6,935,165 B2 | 8/2005 | Bashir et al. |
| 6,948,843 B2 | 9/2005 | Laugharn, Jr. et al. |
| 6,970,741 B1 | 11/2005 | Whitehurst et al. |
| 7,048,730 B2 | 5/2006 | Petrakis |
| 7,083,593 B2 | 8/2006 | Stultz |
| 7,104,988 B2 * | 9/2006 | Altman et al. ............... 606/41 |
| 7,118,531 B2 | 10/2006 | Krill |
| 7,214,190 B1 * | 5/2007 | Wilson ............... 600/309 |
| 7,351,239 B2 | 4/2008 | Gill |
| 7,424,330 B2 | 9/2008 | Duerr et al. |
| 7,699,834 B2 | 4/2010 | Hood et al. |
| 7,811,279 B2 * | 10/2010 | John ............... 604/890.1 |
| 2001/0033796 A1 | 10/2001 | Unger et al. |
| 2001/0036672 A1 | 11/2001 | Anderson et al. |
| 2001/0039414 A1 | 11/2001 | Brines et al. |
| 2001/0044620 A1 | 11/2001 | Krulevitch et al. |
| 2002/0009015 A1 | 1/2002 | Laugharn, Jr. et al. |
| 2002/0065509 A1 | 5/2002 | Lebel et al. |
| 2002/0070116 A1 | 6/2002 | Ohkawa |
| 2002/0072784 A1 | 6/2002 | Sheppard, Jr. et al. |
| 2002/0077673 A1 | 6/2002 | Penner et al. |
| 2002/0090388 A1 | 7/2002 | Humes et al. |
| 2002/0107472 A1 | 8/2002 | Thompson et al. |
| 2002/0111601 A1 | 8/2002 | Thompson |
| 2002/0127736 A1 | 9/2002 | Chou et al. |
| 2002/0173772 A1 | 11/2002 | Olsen |
| 2002/0173773 A1 | 11/2002 | Olsen |
| 2002/0188323 A1 | 12/2002 | Penner et al. |
| 2003/0015768 A1 | 1/2003 | Bosco et al. |
| 2003/0036746 A1 | 2/2003 | Penner et al. |
| 2003/0069560 A1 | 4/2003 | Adamis et al. |
| 2003/0070677 A1 | 4/2003 | Handique et al. |
| 2003/0104590 A1 | 6/2003 | Santini, Jr. et al. |
| 2003/0142901 A1 | 7/2003 | Lahann et al. |
| 2003/0147812 A1 | 8/2003 | Ueberle |
| 2003/0163223 A1 | 8/2003 | Blomquist |
| 2003/0171257 A1 | 9/2003 | Stirbl et al. |
| 2003/0171738 A1 | 9/2003 | Konieczynski et al. |
| 2003/0210997 A1 | 11/2003 | Lopez et al. |
| 2003/0219470 A1 | 11/2003 | Zhang et al. |
| 2003/0234220 A1 | 12/2003 | Lee et al. |
| 2003/0235504 A1 | 12/2003 | Lemoff et al. |
| 2004/0007051 A1 | 1/2004 | Bashir et al. |
| 2004/0010219 A1 | 1/2004 | McCusker et al. |
| 2004/0015154 A1 | 1/2004 | Harper et al. |

| | | | |
|---|---|---|---|
| 2004/0032187 A1 | 2/2004 | Penner et al. | |
| 2004/0034332 A1 | 2/2004 | Uhland | |
| 2004/0036455 A1 | 2/2004 | Cho | |
| 2004/0049245 A1 | 3/2004 | Gass et al. | |
| 2004/0055648 A1 | 3/2004 | Erickson | |
| 2004/0058101 A1 | 3/2004 | Klemm | |
| 2004/0076559 A1 | 4/2004 | Brucker et al. | |
| 2004/0079424 A1 | 4/2004 | Takeda et al. | |
| 2004/0082908 A1 | 4/2004 | Whitehurst et al. | |
| 2004/0106914 A1 | 6/2004 | Coppeta et al. | |
| 2004/0115128 A1 | 6/2004 | Schnitzer | |
| 2004/0120827 A1 | 6/2004 | Kim et al. | |
| 2004/0121486 A1 | 6/2004 | Uhland et al. | |
| 2004/0127844 A1 | 7/2004 | Flaherty | |
| 2004/0133188 A1 | 7/2004 | Vardi et al. | |
| 2004/0137300 A1 | 7/2004 | Gemmen et al. | |
| 2004/0147906 A1 | 7/2004 | Voyiazis et al. | |
| 2004/0166140 A1 | 8/2004 | Santini, Jr. et al. | |
| 2004/0193144 A1 | 9/2004 | Krumme | |
| 2004/0193166 A1 | 9/2004 | Biscup | |
| 2004/0204744 A1 | 10/2004 | Penner et al. | |
| 2004/0210184 A1 | 10/2004 | Kost et al. | |
| 2004/0219732 A1 | 11/2004 | Burns et al. | |
| 2004/0220553 A1 | 11/2004 | Olsen | |
| 2004/0223985 A1 | 11/2004 | Dunfield et al. | |
| 2004/0230182 A1 | 11/2004 | Heruth et al. | |
| 2004/0242976 A1 | 12/2004 | Abreu | |
| 2004/0256584 A1 | 12/2004 | Zimmerling et al. | |
| 2004/0264293 A1 | 12/2004 | Laugharn, Jr. et al. | |
| 2005/0016605 A1 | 1/2005 | Sherman et al. | |
| 2005/0037075 A1 | 2/2005 | Farokhzad et al. | |
| 2005/0055014 A1 | 3/2005 | Coppeta et al. | |
| 2005/0096587 A1 | 5/2005 | Santini, Jr. et al. | |
| 2005/0119733 A1 | 6/2005 | Wiliams et al. | |
| 2005/0123563 A1 | 6/2005 | Doranz et al. | |
| 2005/0143802 A1 | 6/2005 | Soykan et al. | |
| 2005/0181366 A1 | 8/2005 | Ostermeier | |
| 2005/0187515 A1 | 8/2005 | Varrichio et al. | |
| 2005/0187677 A1 | 8/2005 | Walker | |
| 2005/0191194 A1 | 9/2005 | Falk et al. | |
| 2005/0191708 A1 | 9/2005 | Saul et al. | |
| 2005/0192637 A1 | 9/2005 | Girouard et al. | |
| 2005/0234431 A1 | 10/2005 | Williams et al. | |
| 2005/0267440 A1 | 12/2005 | Herman et al. | |
| 2006/0004417 A1 | 1/2006 | Rossing et al. | |
| 2006/0089751 A1 | 4/2006 | Herbst | |
| 2006/0116641 A1 | 6/2006 | Gordon et al. | |
| 2006/0149321 A1 | 7/2006 | Merry et al. | |
| 2006/0201432 A1 | 9/2006 | Pratt | |
| 2006/0224128 A1 | 10/2006 | Lurvey et al. | |
| 2006/0241747 A1 | 10/2006 | Shaoulian et al. | |
| 2007/0016171 A1 | 1/2007 | Podvin et al. | |
| 2007/0074722 A1 | 4/2007 | Giroux et al. | |
| 2007/0078445 A1 | 4/2007 | Malloy | |
| 2007/0106281 A1 | 5/2007 | Hood et al. | |
| 2009/0227988 A1 | 9/2009 | Wood, Jr. et al. | |

FOREIGN PATENT DOCUMENTS

| | | |
|---|---|---|
| WO | WO 02/056790 A2 | 7/2002 |
| WO | WO 03/049592 A2 | 6/2003 |
| WO | WO 2005/084273 A3 | 9/2005 |

OTHER PUBLICATIONS

UK Intellectual Property Office Examination Report Under Section 18(3); App. No. GB0809489.8; bearing a date of Jul. 25, 2011; pp. 1-2.

UK Intellectual Property Office Examination Report Under Section 18(3); App. No. GB0809510.1; bearing a date of Oct. 27, 2010; pp. 1-2.

UK Intellectual Property Office Examination Report Under Section 18(3); App. No. GB0809489.8; bearing a date of Oct. 27, 2010; pp. 1-3.

UK Intellectual Property Office Examination Report Under Section 18(3); App. No. GB0809491.4; bearing a date of Oct. 27, 2010; pp. 1-2.

UK Intellectual Property Office Examination Report Under Section 18(3); App. No. GB0809498.9; Jan. 7, 2011; 3 pages.

UK Intellectual Property Office Examination Report Under Section 18(3); App. No. GB0809500.2; bearing a date of Jul. 29, 2011; pp. 1.

UK Intellectual Property Office Examination Report Under Section 18(3); App. No. GB0809510.1; bearing a date of Jul. 29, 2011; pp. 1.

UK Intellectual Property Office Examination Report Under Section 18(3); App. No. GB0809491.4; bearing a date of Aug. 4, 2011; pp. 1-2.

UK Intellectual Property Office Examination Report Under Section 18(3); App. No. GB0809487.2; bearing a date of Oct. 1, 2010; pp. 1-2.

Agarwal, Abhishek K.; Atencia, Javier; Beebe, David J.; Jiang, Hongrui; "Magnetically-driven temperature-controlled microfluidic actuators"; pp. 1-5; located at: http://www.unl.im.dendai.ac.jp/INSS2004/INSS2004_papers/OralPresentations/C2.pdf.

"Artificial Muscle Research Institute"; University of New Mexico; Bearing dates of May 29, 2000 and Oct. 14, 2005, printed on Oct. 21, 2005; pp. 1-7; located at: http://www.unm.edu/~amri/.

Bagnato, Joshua D.; Eilers, Alanna L.; Horton, Robert A.; Grissom, Charles B.; "Synthesis and Characterization of a Cobalamin-Colchicine Conjugate as a Novel Tumor-Targeted Cytotoxin"; The Journal of Organic Chemistry; Bearing dates of 2004 and Jun. 3, 2004, printed on Oct. 21, 2005; pp. 8987-8996 (pp. 1-1); vol. 69, No. 26; American Chemical Society; located at: http://pubs.acs.org/cgi-bin/abstract.cgi/joceah/2004/69/i26/abs/jo049953w.html.

Boniface, J. Jay; Lyons, Daniel S.; Wettstein, Daniel A.; Allbritton, Nancy L.; Davis, Mark M.; "Evidence for a Conformational Change in a Class II Major Histocompatibility Complex Molecule Occuring in the Same pH Range Where Antigen Binding Is Enhanced"; J. Exp. Med.; Bearing dates of Jan. 1996 and Jun. 26, 2005; pp. 119-126; vol. 183; The Rockefeller University Press; located at: http://www.jem.org.

Chen, Haitao; Rosengart, Axel J.; Kaminski, Michael D.; Caviness, Patricia L.; Mertz, Carol J.; Balasubramanian, Viji; Ebner, Armin D.; Ritter, James A.; "Achieving and Optimizing Separation of Magnetic Carriers from Pulsatile Blood Flow"; pp. 1-1; Collaborative Investigators for Applied Nanotechnology in Medicine; located at: http://www.cmt.anl.gov/nanomedicine/posters/carrier-separation.pdf.

Chen, Haitao; Kaminski, Michael D.; Rosengart, Axel J.; Ebner, Armin D.; Guy, Sandra G.; Mertz, Carol J.; Caviness, Patricia L.; Ritter, James A.; "Magnetizable Intravascular Stent and Functionalized Magnetic Carriers: A Novel Approach for Noninvasive Yet Targeted Drug Delivery"; pp. 1-1; Collaborative Investigators for Applied Nanotechnology in Medicine; located at: http://www.cmt.anl.gov/nanomedicine/posters/stent.pdf.

Chen, Haitao; Ebner, Armin D.; Ritter, James A.; Kaminski, Michael D.; Rosengart, Axel J.; "Sequestration of Blood-Borne Magnetic Drug Carrier Particles Using Magnetizable Intravascular Stents"; pp. 1-1; Collaborative Investigators for Applied Nanotechnology in Medicine; located at: http://cmtpub.cmt.anl.gov/nanomedicine/posters/sequestration.pdf.

Davison, Brian H.; Adams, M.W.W.; "Characterization of Chemically Modified Enzymes for Bioremediation Reactions"; Final Report: U.S. Department of Energy; Bearing dates of Sep. 22, 2000, Oct. 1, 1996 to Aug. 31, 2000; pp. 1-14.

Edelman, E.R.; Kost, J.; Bobeck, H.; Langer, R.; "Regulation of drug release from polymer matrices by oscillating magnetic fields"; Journal of Biomedical Materials Research; Bearing a date of 1985; pp. 67-83; vol. 19; John Wiley and Sons, Inc.

Edwards, David A.; Ben-Jebria, Abdelaziz; Langer, Robert; "Invited Review: Recent advances in pulmonary drug delivery using large, porous inhaled particles"; Journal of Applied Physiology; Bearing a date of 1998, downloaded on Oct. 12, 2005; pp. 379-385; vol. 84 (sic 85), Issue 2; The American Physiological Society; located at: http://jap.physiology.org.

Erion, Mark D.; Van Poelje, Paul D.; Mackenna, Deidre A.; Colby, Timothy J.; Montag, Annika C.; Fujitaki, James M.; Linemeyer, David L.; Bullough, David A.; "Absorption, Distribution, Metabolism, and Excretion: Liver-Targeted Drug Delivery Using HepDirect Prodrugs"; Journal of Pharmacology and Experimental Therapeutics *Fast Forward*; Bearing dates of Aug. 31, 2004 and 2005, printed on Oct. 21, 2005; pp. 1-2; Metabasis Therapeutics, Inc. and American Society for Pharmacology and Experimental Therapeutics; San Diego; located at: http://jpet.aspetjournals.org/cgi/content/abstract/312/2/554.

"Ferrofluids"; Liquidsresearch.com; Bearing a date of 2000, printed on Oct. 21, 2005; pp. 1-1; Liquids Research Limited; located at: http://www.liquidsresearch.com/products/ferro.asp.

Jacque, David; "Science and Technology: Magnetic Nanoparticles Eyed as Biohazard Treatment"; Argonne News; Bearing a date of Nov. 10, 2003, printed on Oct. 21, 2005; pp. 1-3; located at: http://www.cmt.anl.gov/science-technology/processchem/magnetic-nanoparticles.shtml.

Johnson, Audrey M.; Sadoway, Donald R.; Cima, Michael J.; Langer, Robert; "Design and Testing of an Impedance-Based Sensor for Monitoring Drug Delivery"; Journal of the Electrochemical Society; Bearing a date of 2005; pp. H6-H11; vol. 152, Issue 1; The Electrochemical Society, Inc.

Jonnalagadda, Sriramakamal; Robinson, Dennis H.; "A Bioresorbable, Polylactide Reservoir for Diffusional and Osmotically Controlled Drug Delivery"; AAPS PharmSciTech; Bearing a date of 2000; pp. 1-9; vol. 1, No. 4, Article 29; located at: http://www.pharmscitech.com/.

Kaminski, Michael D.; Rosengart, Axel J.; "Biohazard Detoxification Using Magnetic Nanoparticles"; Argonne National Laboratory and The University of Chicago; located at: http://www.cmt.anl.gov/science-technology/processchem/BiohazardDetoxification.pdf.

Knapp, Louise; "Ironing Out Blood Impurities"; Wired News; Bearing dates of Dec. 8, 2003 and 2005, printed on Oct. 21, 2005; pp. 1-4; Lycos, Inc.; located at: http://www.wired.com/news/print/0,1294,61505,00.html and http://www.wired.com/news/medtech/0,1286,61505,00.html.

Kohane, Daniel S.; Plesnila, Nikolaus; Thomas, Sunu S.; Le, Dean; Langer, Robert; Moskowitz, Michael A.; "Lipid-sugar particles for intracranial drug delivery: safety and biocompatibility"; Brain Research; Bearing a date of 2002; pp. 206-213; vol. 946; Elsevier Science B.V.; located at: http://www.elsevier.com/locate/bres.

Kost, Joseph; Wolfrum, Jackie; Langer, Robert; "Magnetically enhanced insulin release in diabetic rats"; Journal of Biomedical Materials Research; Bearing a date of 1987; pp. 1367-1373; vol. 21; John Wiley and Sons, Inc.

Lavan, David A.; McGuire, Terry; Langer, Robert; "Small-Scale Systems for in vivo drug delivery"; Nature Biotechnology: Review; Bearing dates of 2003 and Oct. 2003; pp. 1184-1191; vol. 21, No. 10; Nature Publishing Group; located at: http://www.nature.com/naturebiotechnology.

"Lecture 9. Biochemistry 3521—Fordham University—1999"; BIFC 3521: Lecture; Bearing dates of Feb. 10, 1999 and 1999, printed on Oct. 24, 2005; pp. 1-11; located at: http://dwb.unl.edu/Teacher/NSF/C10/C10Links/www.fordham.edu/Biochem_3521/lec.t9/lect9.html.

Li, Yawen; Shawgo, Rebecca S.; Tyler, Betty; Henderson, Paul T.; Vogel, John S.; Rosenberg, Aron; Storm, Phillip B.; Langer, Robert; Brem, Henry; Cima, Michael J.; "In vivo release from a drug delivery MEMS device"; Journal of Controlled Release; Bearing dates of 2004 and Sep. 28, 2004; pp. 211-219; vol. 100; Elsevier B.V.; located at: http://www.sciencedirect.com and http://www.elsevier.com/locate/jconrel.

Lindsey, Keiran; "DMD00 The 2000 Guide to the Membrane Industry"; Bearing a date of Dec. 2000, printed on Aug. 12, 2005; pp. 1-16; Business Communications Company, Inc.; located at: http://www.bccresearch.com/print/membrane_p/DMD00_print.html.

Lurie, Karen; "Instant Armor"; ScienCentral News; Bearing dates of Dec. 4, 2003, Oct. 21, 2005 and 2000-2005, printed on Oct. 21, 2005; pp. 1-3; ScienCentral, Inc.; Located at: http://www.sciencentral.com/articles/view.php3?article_id=21839212&language=english.

"Magnetorheological Fluids"; Liquidsresearch.com; Bearing a date of 2000, printed on Oct. 21, 2005; pp. 1-2; Liquids Research Limited; located at: http://www.liquidsresearch.com/products/magnet.asp.

"Membrane"; pp. 1-11.

Moses, Marsha A.; Brem, Henry; Langer, Robert; "Review: Advancing the field of drug delivery: Taking aim at cancer"; Cancer Cell; Bearing dates of 2003 and Nov. 2003; pp. 337-341; vol. 4; Cell Press.

Neto, A.M. Figueiredo; Godinho, M.H.; Toth-Katona, T.; Palffy-Muhoray, P.; "Optical, Magnetic and Dielectric Properties of Non-Liquid Crystalline Elastomers Doped with Magnetic Colloids"; Brazilian Journal of Physics; Bearing a date of Mar. 2005; pp. 184-189; vol. 35, No. 1.

"Our Technology"; Dynal Invitrogen Corporation; printed on Oct. 21, 2005; pp. 1-3; Dynal Biotech; located at: http://www.dynalbiotech.com/kunder/dynal/dynalpub401.nsf/($All)/A24F11400EF33100C1256EA60054D9C1?OpenDocument.

Paschke, R; Paetz, C; Mueller, T; Schmoll, HJ; Mueller H; Sorkau, E; Sinn, E; "Biomolecules linked to transition metal complexes—new chances for chemotherapy"; Current Medicinal Chemistry; Bearing dates of Oct. 2003 and Oct. 18, 2005, printed on Oct. 24, 2005; pp. 2033-2044 (pp. 1-2); vol. 10, No. 19; PubMed; located at: http://www.ncbi.nlm.nih.gov/entrez/query.fcgi?cmd=Retrieve&db=PubMed&list_uids=12871101&dopt=Abstract.

"Polymer Gel Actuators and Sensors"; web.mit.edu; pp. 1-5; located at: http://web.mit.edu/cmse/www/Leeb97.pdf.

Prausnitz, Mark R.; Mitragotri, Samir; Langer, Robert; "Reviews: Current Status and Future Potential of Transdermal Drug Delivery"; Nature Reviews: Drug Discovery; Bearing a date of Feb. 2004; pp. 115-124; vol. 3; located at: http://www.nature.com/reviews/drugdisc.

Puccetti, L; Fasolis, G; Vullo, D; Chohan, ZH; Scozzafava, A; Supuran, CT; "Carbonic anhydrase inhibitors. Inhibition of cytosolic/tumor-associated carbonic anhydrase isozymes I, II, IX, and XII with Schiff's bases incorporating chromone and aromatic sulfonamide moieties, and their zinc complexes"; Bioorganic & Medicinal Chemistry Letters; Bearing dates of Jun. 15, 2005 and Oct. 18, 2005, printed on Oct. 24, 2005; pp. 3096-3101 (pp. 1-2); vol. 15, No. 12; PubMed; located at: http://www.ncbi.nlm.nih.gov/entrez/query.fcgi?cmd=Retrieve&db=pub....

"Quantitative Physiology: Cells and Tissues-Lecture 6"; Bearing a date of Sep. 20, 2004; pp. 1-6; vol. 1: 4.1-4.3.2.3; 4.4-4.5.1.2; located at: http://umech.mit.edu/6.021J/2004/lectures/lec06hi.pdf.

U.S. Appl. No. 11/272,573, filed May 10, 2007, Hood et al.
U.S. Appl. No. 11/272,572, filed May 10, 2007, Hood et al.
U.S. Appl. No. 11/271,146, filed May 10, 2007, Hood et al.
U.S. Appl. No. 11/271,145, filed May 10, 2007, Hood et al.
U.S. Appl. No. 11/270,799, filed May 10, 2007, Hood et al.
Japanese Examination Report; App. No. 2008-540179; Oct. 6, 2011; pp. 1-3; no translation provided.
U.S. Appl. No. 11/521,076, filed May 10, 2007, Hood et al.
U.S. Appl. No. 11/505,259, filed Jun. 14, 2007, Hood et al.
U.S. Appl. No. 11/482,097, filed May 10, 2007, Hood et al.
U.S. Appl. No. 11/474,068, filed May 10, 2007, Hood et al.
U.S. Appl. No. 11/450,159, filed May 10, 2007, Hood et al.
U.S. Appl. No. 11/372,492, filed Jun. 28, 2007, Hood et al.
U.S. Appl. No. 11/372,226, Jun. 28, 2007, Hood et al.
U.S. Appl. No. 11/335,911, filed May 10, 2007, Hood et al.
U.S. Appl. No. 11/335,788, filed May 10, 2007, Hood et al.
U.S. Appl. No. 11/335,786, filed May 10, 2007, Hood et al.
U.S. Appl. No. 11/335,785, filed May 10, 2007, Hood et al.
U.S. Appl. No. 11/302,449, filed Jun. 14, 2007, Hood et al.
U.S. Appl. No. 11/302,407, filed Jun. 14, 2007, Hood et al.
U.S. Appl. No. 11/302,321, filed Jun. 14, 2007, Hood et al.

"Ferromagnetic SMA Actuator"; Midé; Bearing a date of 2004, printed on Aug. 11, 2005; pp. 1-2; Mide Technology Corporation; located at: http://www.mide.com/pdf_html/FSMAA.htm.

"Filtration and Ultrafiltration Equipment and Techniques"; Membranes.nist.gov; printed on Aug. 12, 2005; pp. 1-14; located at: http://www.membranes.nist.gov/ACSchapter/pellePAGE.html.

Grayson, Amy C. Richards; Shawgo, Rebecca S.; Johnson, Audrey M.; Flynn, Nolan T.; Li, Yawen; Cima, Michael J.; Langer, Robert; "A BioMEMS Review: MEMS Technology for Physiologically Integrated Devices"; Proceedings of the IEEE; Bearing dates of 2004 and Jan. 2004; pp. 6-21; vol. 92, No. 1; IEEE.

Grayson, Amy C. R.; Voskerician, Gabriela; Lynn, Aaron; Anderson, James M.; Cima, Michael J.; Langer, Robert; "Differential degradation rates in vivo and in vitro of biocompatible poly(lactic acid) and poly(glycolic acid) homo-and co-polymers for a polymeric drug-delivery microchip"; Journal of Biomaterials Science, Polymer Edition; Bearing a date of 2004; pp. 1281-1304; vol. 15, No. 10; VSP; located at: http://www.vsppub.com.

Grayson, Amy C. Richards; Choi, Insung S.; Tyler, Betty M.; Wang, Paul P.; Brem, Henry; Cima, Michael J.; Langer, Robert; "Multipulse drug delivery from a resorbable polymeric microchip device"; Nature Materials; Bearing dates of 2003 and Nov. 2003; pp. 767-772; vol. 2; Nature Publishing Group; located at: http://www.nature.com/naturematerials.

Gu, H; Ho, PL; Tsang, KW; Wang, L; Xu, B; "Using biofunctional magnetic nanoparticles to capture vancomycin-resistant enterococci and other gram-positive bacteria at ultralow concentration"; Journal of the American Chemical Society; Bearing dates of Dec. 24, 2003 and Oct. 18, 2005, printed on Oct. 21, 2005; pp. 15702-15703 (pp. 1-1); vol. 125, No. 51; PubMed; located at: http://www.ncbi.nlm.nih.gov/entrez/query.fcgi?cmd=Retrieve&db=PubMed&list_uids=14677934&dopt=Abstract.

Kozhevnikov, Ivan V.; "Catalysts for Fine Chemical Synthesis, vol. 2, Catalysis by Polyoxometalates"; Chipsbooks.com; Bearing dates of 2002 and 1998-2006, printed on Oct. 21, 2005; pp. 1-3 (201 pages); vol. 2; Culinary and Hospitality Industry Publications Services; located at: http://www.chipsbooks.com/catcem2.htm.

Krauβ, Robert; Liu, Mario; Reimann, Bert; Richter, Reinhard; Rehberg, Ingo; "Fluid pumped by magnetic stress"; Bearing a date of Jul. 1, 2004; pp. 1-3.

Krauβ, Robert; Liu, Mario; Reimann, Bert; Richter, Reinhard; Rehberg, Ingo; "Fluid pumped by magnetic stress"; Bearing dates of Oct. 11, 2005 and Apr. 4, 2005; pp. 1-3; located at: http://arxiv.org/PS_cache/physics/pdf/0405/0405025.pdf.

Langer, Robert; Peppas, Nicholas A.; "Bioengineering, Food, and Natural Products: Advances in Biomaterials, Drug Delivery, and Bionanotechnology"; AIChE Journal; Bearing a date of Dec. 2003; pp. 2990-3006; vol. 49, No. 12.

Langer, Robert; "Biomaterials in Drug Delivery and Tissue Engineering: One Laboratory's Experience"; Accounts of Chemical Research; Bearing a date of 2000; pp. 94-101; vol. 33, No. 2; American Chemical Society.

Langer, Robert; "Commentary: Transdermal drug delivery: past progress, current status, and future prospects"; Advanced Drug Delivery Reviews; Bearing a date of 2004; pp. 557-558; vol. 56; Elsevier B.V.; located at: http://www.sciencedirect.com and http://www.elsevier.com/locate/addr.

Langer, Robert; "Perspectives: Drug Delivery: Drugs on Target"; Science; Bearing a date of Jul. 6, 2001; pp. 58-59; vol. 293; located at: http://www.sciencemag.org.

Langer, Robert; "Reviews: Drug Delivery and Targeting"; Nature: Therapeutic Horizons; Bearing a date of Apr. 30, 1998; pp. 4-10; vol. 392 Supplement, No. 6679.

Lavan, David A.; Lynn, David M.; Langer, Robert; "Perspectives: Moving smaller in drug discovery and delivery"; Nature Reviews: Drug Discovery; Bearing dates of 2001 and Jan. 2002; pp. 77-84; vol. 1; Macmillan Magazines Ltd; located at: http://www.nature.com/reviews/drugdisc.

"Research/Team 02: Project 2.4: Chemically-switchable magnetic materials for actuators"; MIT Institute For Soldier Nanotechnologies; printed on Oct. 21, 2005; pp. 1-2; located at: http://web.mit.edu/isn/research/team02/project02_04.html.

Robinson, Mark A.; Charlton, Stuart T.; Garnier, Philippe; Wang, Xiang-Tao; Davis, Stanley S.; Perkins, Alan C.; Frier, Malcolm; Duncan, Ruth; Savage, Tony J.; Wyatt, David A.; Watson, Susan A.; Davis, Benjamin G.; "Pharmacology: LEAPT: Lectin-directed enzyme-activated prodrug therapy"; PNAS; Bearing dates of Sep. 24, 2004, Oct. 5, 2004, and 2004, printed on Oct. 21, 2005; pp. 14527-14532 (pp. 1-16); vol. 101, No. 40; National Academy of Sciences; located at: http://www.pnas.org/cgi/content/full/101/40/14527.

Ross, Jennifer L.; Santangelo, Christian D.; Makrides, Victoria; Fygenson, D. Kuchnir; "Tau induces cooperative Taxol binding to microtubules"; PNAS; Bearing dates of Aug. 31, 2004 and 2004; pp. 12910-12915; vol. 101, No. 35; The National Academy of Sciences of the USA; located at: http://gabriel.physics.ucsb.edu/~deborah/pub/RossPNASv101p12910y04.pdf.

Safarik, Ivo; Safarikova, Mirka; "Magnetic techniques for the isolation and purification of proteins and peptides"; BioMagnetic Research and Technology; Bearing dates of 2004, Nov. 26, 2004 and 1999-2005, printed on Oct. 21, 2005; pp. 1-21; vol. 2, No. 7; BioMed Central Ltd.; located at: http://www.biomagres.com/content/2/1/7.

Santini, Jr., John T.; Richards, Amy C.; Scheidt, Rebecca; Cima, Michael J.; Langer, Robert; "Reviews: Microchips as Controlled Drug-Delivery Devices"; Angewandte Chemie International Edition; Bearing a date of 2000; pp. 2396-2407; vol. 39; Wiley-VCH.

Shahinpoor, M.; Bar-Cohen, Y.; Simpson, J.O.; Smith, J.; "Artificial Muscle Research Institute: Paper: Ionic Polymer-Metal Composites (IPMC) As Biomimetic Sensors, Actuators and Artificial Muscles—A Review"; University of New Mexico; printed on Oct. 21, 2005; pp. 1-28; located at: http://www.unm.edu/~amri/paper.html.

Shahinpoor, Mohsen; Kim, Kwang J; "Ionic polymer-metal composites: I. Fundamentals"; Smart Materials and Structures; Bearing dates of Aug. 7, 2001 and 2001; pp. 819-833; vol. 10; IOP Publishing Ltd; UK.

Shawgo, Rebecca S.; Voskerician, Gabriela; Linh Ho Duc, Hong; Li, Yawen; Lynn, Aaron; MacEwan, Matthew; Langer, Robert; Anderson, James M.; Cima, Michael J.; "Repeated in vivo electrochemical activation and the biological effects of microelectromechanical systems drug delivery device"; Journal of Biomedical Materials Research; Bearing dates of 2004 and Oct. 26, 2004; pp. 559-568; vol. 71A; Wiley Periodicals, Inc; located at: http://www.interscience.wiley.com.

Sridhar, J; Wei, ZL; Nowak, I; Lewin, NE; Ayres, JA; Pearce LV; Blumberg, PM; Kozikowski, AP; "New bivalent PKC ligands linked by a carbon spacer: enhancement in binding affinity"; J Med Chem.; Bearing dates of Sep. 11, 2003 and Oct. 18, 2005, printed on Oct. 24, 2005; pp. 4196-4204 (pp. 1-2); vol. 46, No. 19; PubMed; Located at: http://www.ncbi.nlm.nih.gov/entrez/query.fcgi?cmd=Retrieve&db=PubMed&list_uids=12954072&dopt=Abstract.

Su, Yu-Chuan; Lin, Liwei; "A Water-Powered Micro Drug Delivery System"; Journal of Microelectromechanical Systems; Bearing dates of 2004 and Feb. 2004; pp. 75-82; vol. 13, No. 1; IEEE.

Theeuwes, F.; Yum, S.I.; "Principles of the Design and Operation of Generic Osmotic Pumps for the Delivery of Semisolid or Liquid Drug Formulations"; Annals of Biomedical Engineering; Bearing a date of Dec. 1976 and 1976; pp. 343-353; vol. 4, No. 4; Academic Press, Inc.

Voskerician, Gabriela; Shive, Matthew S.; Shawgo, Rebecca S.; Von Recum, Horst; Anderson, James M.; Cima, Michael J.; Langer, Robert; "Biocompatibility and biofouling of MEMS drug delivery devices"; Biomaterials; Bearing a date of 2003; pp. 1959-1967; vol. 24; Elsevier Science Ltd.; located at: http://www.sciencedirect.com and http://www.elsevier.com/locate/biomaterials.

Voskerician, Gabriela; Shawgo, Rebecca S.; Hiltner, P. Anne; Anderson, James M.; Cima, Michael J.; Langer, Robert; "In Vivo Inflammatory and Wound Healing Effects of Gold Electrode Voltammetry for MEMS Micro-Reservoir Drug Delivery Device"; IEEE Transactions on Biomedical Engineering; Bearing dates of 2004 and Apr. 2004; pp. 627-635; vol. 51, No. 4; IEEE.

Zrinyi, M.; Barsi, L.; Büki, A.; "Direct Observation of Discrete and Reversible Shape Transition in Magnetic Field Sensitive Polymer Gels"; printed on Oct. 21, 2005; pp. 1-6; located at: http://www.kfki.hu/~cheminfo/hun/olvaso/zrinyi/polymgel.html.

Chen, Haitao; Rosengart, Axel J.; Kaminski, Michael D.; Caviness, Patricia L.; Mertz, Carol J.; Balasubramanian, Viji; Ebner, Armin D.; Ritter, James A.; "Achieving and Optimizing Separation of Magnetic Carriers from Pulsatile Blood Flow"; created on Mar. 1, 2010; pp. 1-1; Collaborative Investigators for Applied Nanotechnology in Medicine; located at: http://www.cmt.anl.gov/nanomedicine/posters/carrier-separation.pdf.

Chen, Haitao; Kaminski, Michael D.; Rosengart, Axel J.; Ebner, Armin D.; Guy, Sandra G.; Mertz, Carol J.; Caviness, Patricia L.; Ritter, James A.; "Magnetizable Intravascular Stent and Functionalized Magnetic Carriers: A Novel Approach for Noninvasive Yet Targeted Drug Delivery"; created on Mar. 1, 2010; pp. 1-1; Collaborative Investigators for Applied Nanotechnology in Medicine; located at: http://www.cmt.anl.gov/nanomedicine/posters/stent.pdf.

Chen, Haitao; Ebner, Armin D.; Ritter, James a.; Kaminski, Michael D.; Rosengart, Axel J.; "Sequestration of Blood-Borne Magnetic Drug Carrier Particles Using Magnetizable Intravascular Stents"; created on Mar. 1, 2010; pp. 1-1; Collaborative Investigators for Applied Nanotechnology in Medicine; located at: http://cmtpub.cmt.anl.gov/nanomedicine/posters/sequestration.pdf.

Kaminski, Michael D.; Rosengart, Axel J.; "Biohazard Detoxification Using Magnetic Nanoparticles"; created on Mar. 1, 2010; Argonne National Laboratory and The University of Chicago; located at: http://www.cmt.anl.gov/science-technology/processchem/BiohazardDetoxification.pdf "Membrane"; created on Mar. 1, 2010; pp. 1-11.

"Polymer Gel Actuators and Sensors"; web.mit.edu; created on Mar. 1, 2010; pp. 1-5; located at: http://web.mit.edu/cmse/www/Leeb97.pdf.

* cited by examiner $T_1 < T_2$

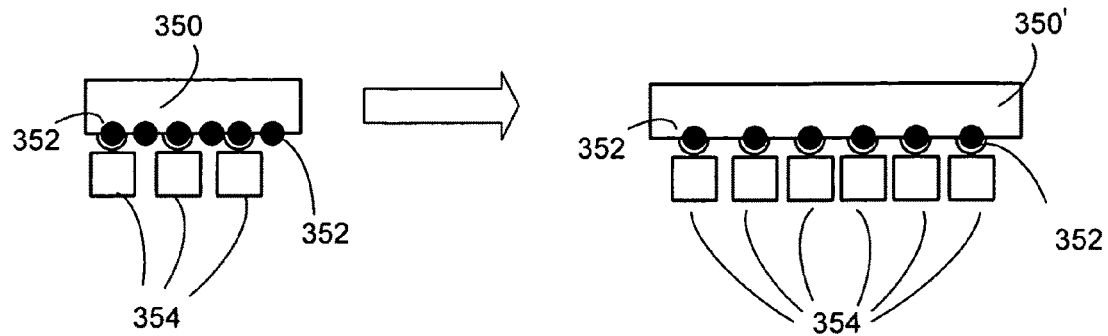
FIG. 9A  FIG. 9B
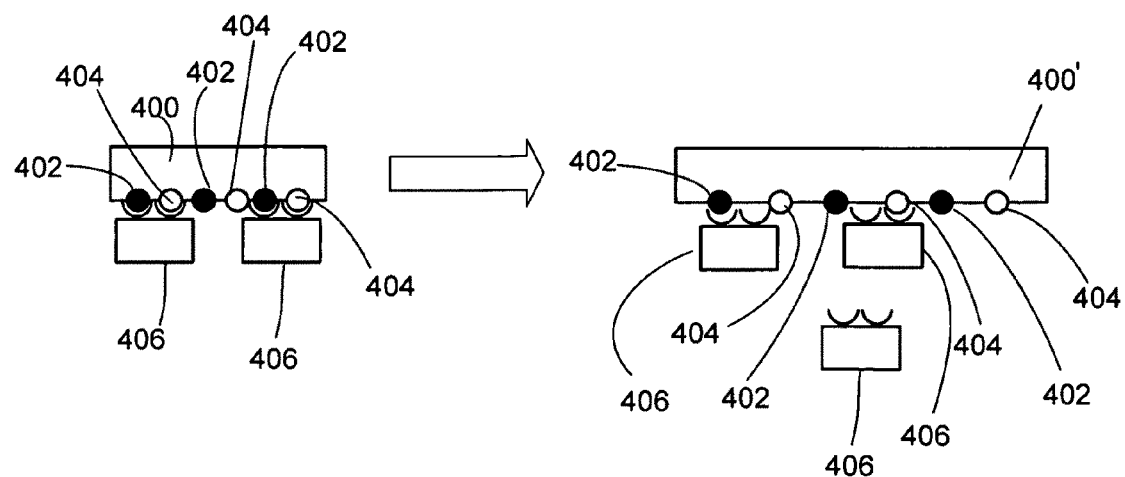
FIG. 10A  FIG. 10B

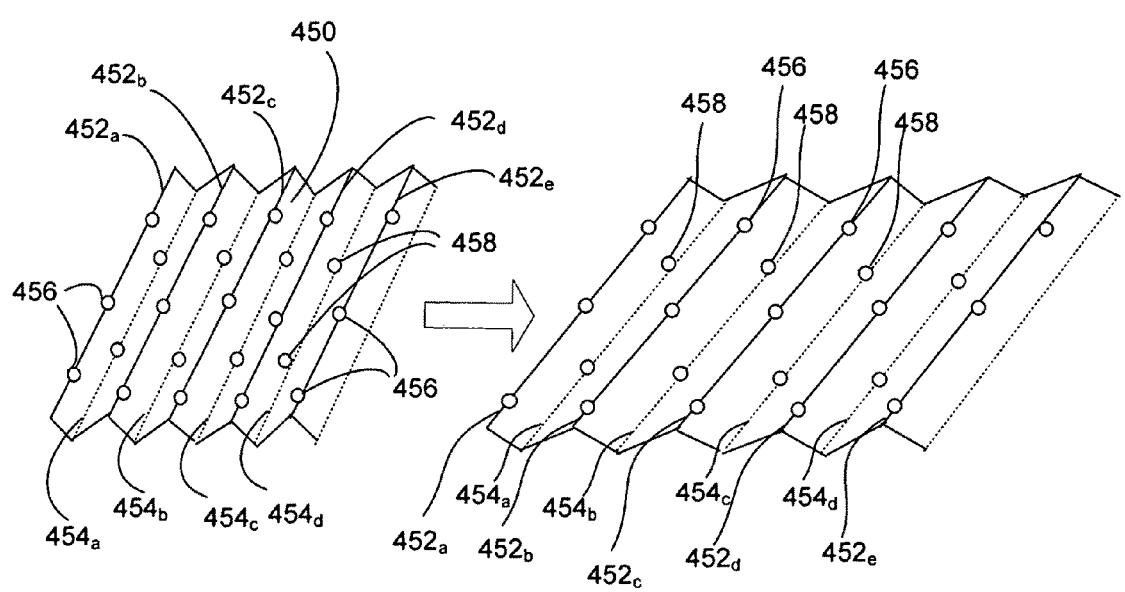
FIG. 11A                                    FIG. 11B

METHOD AND SYSTEM FOR CONTROL OF OSMOTIC PUMP DEVICE

CROSS-REFERENCE TO RELATED APPLICATIONS

For purposes of the United States Patent Office (USPTO) extra-statutory requirements, the present application is a DIVISION application of U.S. patent application Ser. No. 11/302,450 titled METHOD AND SYSTEM FOR CONTROL OF OSMOTIC PUMP DEVICE, naming LEROY E. HOOD; MURIEL Y. ISHIKAWA; EDWARD K. Y. JUNG; ROBERT LANGER; CLARENCE T. TEGREENE; LOWELL L. WOOD, JR.; AND VICTORIA Y. H. WOOD as inventors, filed 13 Dec. 2005, which is copending, or is an application of which a co-pending application is entitled to the benefit of the filing date. The present application claims the benefit of the earliest available effective filing date(s) (i.e., claims earliest available priority dates for other than provisional patent applications or claims benefits under 35 USC §119(e) for provisional patent applications) for any and all applications to which patent application Ser. No. 11/302,450 claims the benefit of priority, including but not limited to U.S. patent application Ser. No. 11/272,524, titled REMOTE CONTROLLED IN SITU REACTION DEVICE, naming LEROY E. HOOD, MURIEL Y. ISHIKAWA, EDWARD K. Y. JUNG, ROBERT LANGER, CLARENCE T. TEGREENE, LOWELL L. WOOD, JR. AND VICTORIA Y. H. WOOD as inventors, filed 9 Nov. 2005. All subject matter of U.S. patent application Ser. No. 11/302,450 and of any and all applications from which it claims the benefit of the earliest available effective filing date(s) is incorporated herein by reference to the extent such subject matter is not inconsistent herewith. The applicant entity has provided above a specific reference to the application(s) from which priority is being claimed—as required by statute. Applicant entity understands that the statute is unambiguous in its specific reference language and does not require either a serial number or any characterization, such as "continuation" or "continuation-in-part" or "divisional," for claiming priority to U.S. patent applications. Notwithstanding the foregoing, the applicant entity has provided above a specific reference to the application(s) from which priority is being claimed, but expressly points out that such designations are not to be construed in any way as any type of commentary and/or admission as to whether or not the present application contains any new matter in addition to the matter of its parent application(s). Any designation that the present application is a "division" should not be construed as an admission that the present application claims subject matter that is patentably distinct from claimed subject matter of its parent application.

TECHNICAL FIELD

The present application relates, in general, to the field of osmotic pump devices and systems, and/or methods for remotely controlling the operation of osmotic pump devices.

BACKGROUND

Implantable controlled release devices for drug delivery have been developed. Certain devices rely upon the gradual release of a drug from a polymeric carrier over time, due to degradation of the carrier. Polymer-based drug release devices are being developed that include a drug in a ferropolymer that may be heated by an externally applied magnetic field, thus influencing the drug release. MEMS based drug release devices that include integrated electrical circuitry are also under development, as are MEMS based systems for performing chemical reactions. Implantable osmotic pump devices have been developed for drug delivery purposes. Wireless transmission of electromagnetic signals of various frequencies is well known in the areas of communications and data transmission, as well as in selected biomedical applications.

SUMMARY

The present application relates, in general, to the field of osmotic pump devices and systems. In particular, the present application relates to remotely controlled osmotic pump devices that make use of control signals carried between a remote controller and an osmotic pump device in an environment by electrical, magnetic, or electromagnetic fields or radiation. Embodiments of a system including a remotely controlled osmotic pump device and associated controller are described. Methods of use and control of the device are also disclosed. According to various embodiments, an osmotic pump device is placed in an environment in order to eject a material into the environment. Exemplary environments include a body of an organism, a body of water or other fluid, or an enclosed volume of a fluid.

BRIEF DESCRIPTION OF THE FIGURES

FIGS. 9A and 9B depict an example of the effect of stretching of an interaction region;

FIGS. 10A and 10B depict another example of an effect of stretching of an interaction region;

FIGS. 11A and 11B depict unfolding of a pleated interaction region;

DETAILED DESCRIPTION

Figure 1:
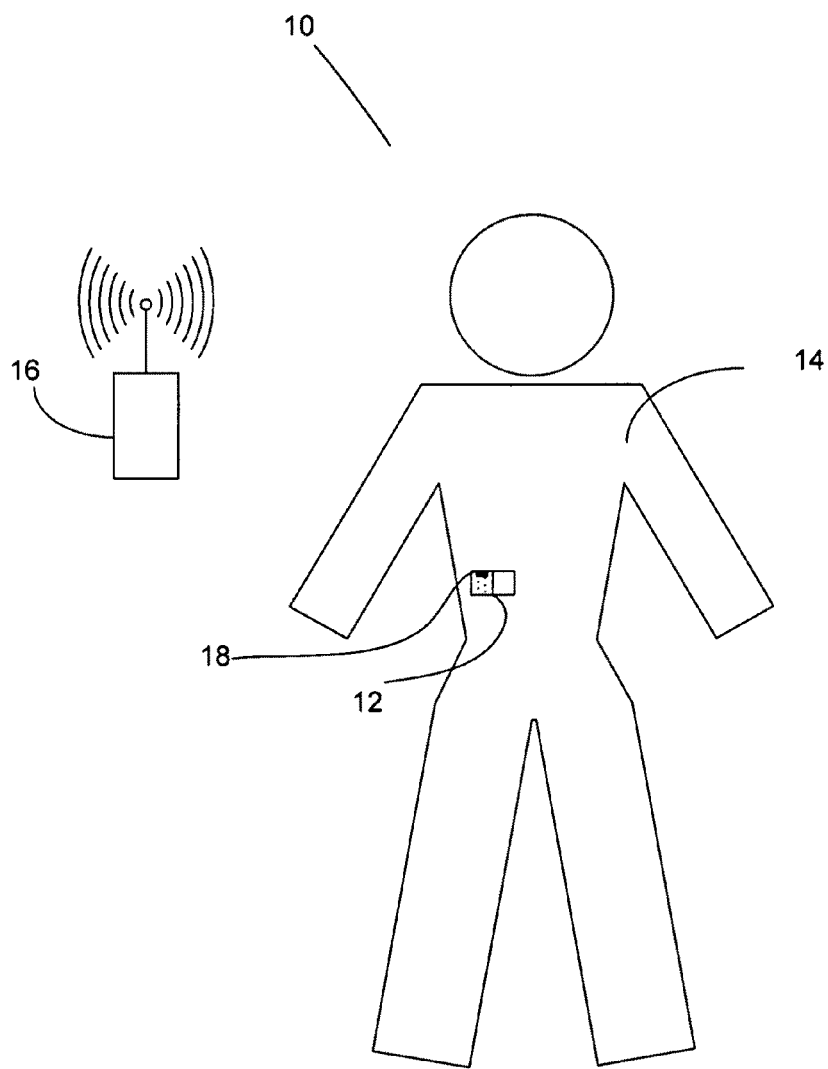
FIG. 1 illustrates an embodiment of a system including a remotely controlled osmotic pump device.

FIG. 1 depicts a first exemplary embodiment of an osmotic pump system 10. In the embodiment of FIG. 1, osmotic pump system 10 includes osmotic pump device 12 located in an environment 14, (which, in this particular example, is a human body) and remote controller 16. As used herein, the term "remote" refers to the transmission of information (e.g. data or control signals) or power signals or other interactions between spatially separated devices or apparatuses, such as the remote controller or the osmotic pump system without a connecting element such as a wire or cable linking the remote controller and the osmotic pump system, and does not imply a particular spatial relationship between the remote controller and the osmotic pump device, which may, in various embodiments, be separated by relatively large distances (e.g. miles or kilometers) or a relatively small distances (e.g. inches or millimeters). Osmotic pump device 12 includes a remotely activatable control element 18 that is responsive to an electromagnetic control signal generated by remote controller 16.

Figure 2A:
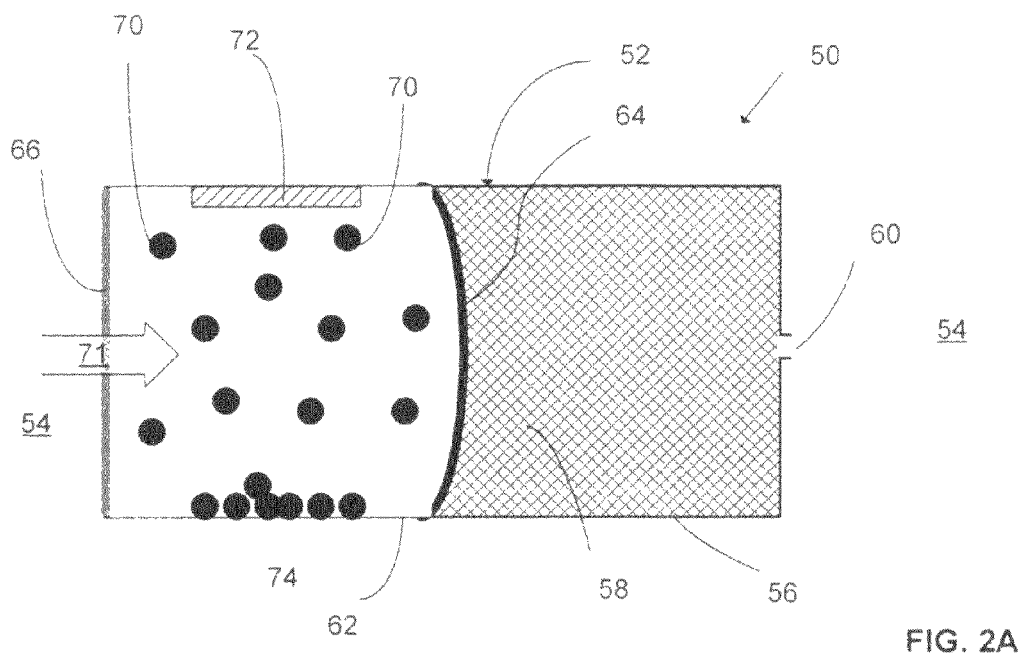
FIGS. 2A and 2B illustrate operation of an osmotic pump device.
Figure 2B:
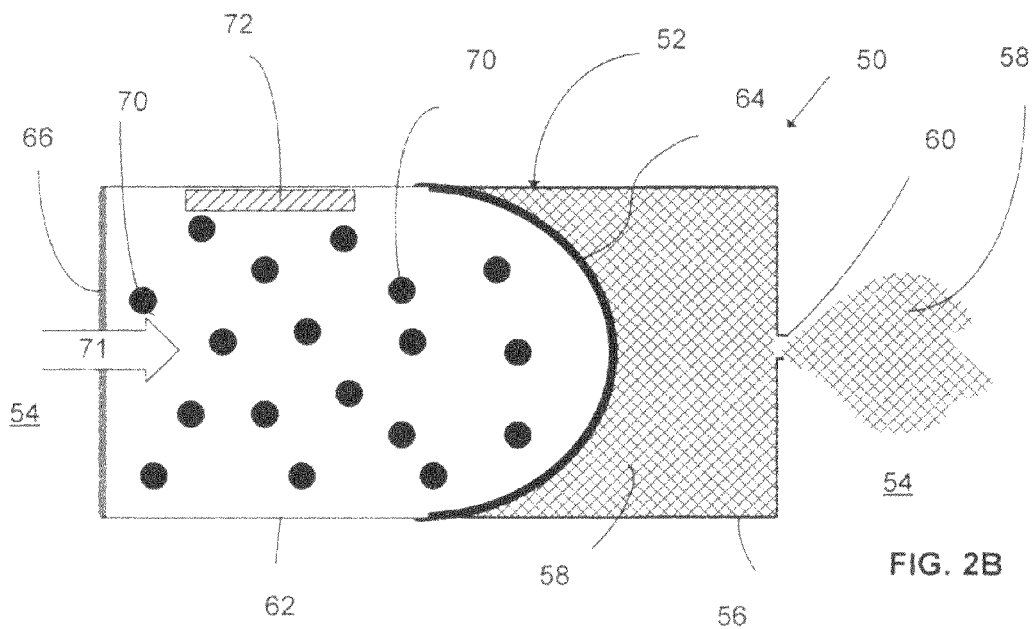

According to one exemplary embodiment of an osmotic pump device, as depicted in FIGS. 2A and 2B, an osmotic pump system may include a body structure 52 configured for placement in an environment 54, a delivery reservoir 56 capable of containing a delivery fluid 58 to be delivered into the environment 54, e.g. via outlet 60, an osmotic chamber 62, a pressure-responsive movable barrier 64 separating the osmotic chamber 62 from delivery reservoir 56, and semi-permeable membrane 66 separating the osmotic chamber 62 from an osmotic fluid source, which in this example is environment 54. An osmotic pressure-generating material 70 may be contained within the osmotic chamber 62, with the generation of osmotic pressure by the osmotic pressure-generating material 70 controllable by an electromagnetic field control signal. The pressure-responsive movable barrier 64 may be substantially impermeable to the osmotic pressure-generating material 70 and configured to move in response to a change in pressure in the osmotic chamber 62 to produce a change in at least one of pressure or volume in the delivery reservoir 56, and the semi-permeable membrane 66 separating the osmotic chamber 62 from an osmotic fluid source 68 may be substantially permeable by fluid 71 from the osmotic fluid source 68 but substantially impermeable to the osmotic pressure-generating material 70. The pressure-responsive movable barrier 64 may include a flexible membrane 64, as depicted in FIGS. 2A and 2B, or a piston, as depicted in, e.g., FIGS. 5A and 5B at reference number 206.

The body structure of the osmotic pump device (e.g. body structure 52 in FIG. 2A) may be adapted for a specific environment. The size, shape, and materials of the body structure influence suitability for a particular environment. For example, a device intended for use in a body of a human or other organism would typically have suitable biocompatibility characteristics. For use in any environment, the body structure (and device as a whole) may be designed to withstand environmental conditions such as temperature, chemical exposure, and mechanical stresses. Moreover, the body structure may include features that allow it to be placed or positioned in a desired location in the environment, or targeted to a desired location in the environment. Such features may include size and shape features, tethers or gripping structures to prevent movement of the body structure in the environment (in the case that the device is placed in the desired location) or targeting features (surface chemistry, shape, etc.)

that may direct the device toward or cause it to be localized in a desired location. Small devices (e.g. as may be used for placement in the body of an organism) may be constructed using methods known to those in skill of the art of microfabrication. In applications where size is not a constraint, a wide variety of fabrication methods may be employed. The body structure of the osmotic pump device may be formed from various materials or combinations of materials, including but not limited to plastics and other polymers, ceramics, metals, and glasses, and by a variety of manufacturing techniques. In some embodiments, the osmotic fluid source may be the environment, while in other embodiments, the osmotic pump system may include a fluid-containing reservoir that serves as an osmotic fluid source.

Various different osmotic pressure-generating materials may be used in osmotic pump systems as described herein. For example, the osmotic pressure-generating material may include ionic and non-ionic water-attracting or water absorbing materials, non-volatile water-soluble species, salts, sugars, polysaccharides, polymers, hydrogels, osmopolymers, hydrophilic polymers, and absorbent polymers, among others. Water-attracting materials may include non-volatile, water-soluble species such as magnesium sulfate, magnesium chloride, potassium sulfate, sodium chloride, sodium sulfate, lithium sulfate, sodium phosphate, potassium phosphate, d-mannitol, sorbitol, inositol, urea, magnesium succinate, tartaric acid, raffinose, various monosaccharides, oligosaccharides and polysaccharides, such as sucrose, glucose, lactose, fructose, dextran, and mixtures thereof. Water absorbing materials include osmopolymers for example hydrophilic polymers that swell upon contact with water. Examples of water-absorbing materials include poly(hydroxyl alkyl methacrylates) MW 30,000-5,000,000, polyvinylpyrrolidone MW 10,000-360,000, anionic and cationic hydrogels, polyelectrolyte complexes, poly(vinyl alcohol) having low acetate residual, optionally cross linked with glyoxal, formaldehyde, or glutaraldehyde and having a degree of polymerization of 200 to 30,000, mixtures of e.g., methylcellulose, cross linked agar and carboxymethylcellulose; or hydroxypropyl methycellulose and sodium carboxymethylcellulose; polymers of N-vinyllactams, polyoxyethylene polyoxypropylene gels, polyoxybutylene-polyoxethylene block copolymer gels, carob gum, polyacrylic gels, polyester gels, polyuria gels, polyether gels, polyamide gels, polypeptide gels, polyamino acid gels, polycellulosic gels, carbopol acidic carboxy polymers MW 250,000-4,000,000, cyanamer polyacrylamides, cross-linked indene-maleic anhydride polymers, starch graft copolymers, acrylate polymer polysaccharides. Other water attracting and/or water absorbing materials include absorbent polymers such as poly(acrylic acid) potassium salt, poly (acrylic acid) sodium salt, poly(acrylic acid-co-acrylamide) potassium salt, poly(acrylic acid) sodium salt-graft-poly(ethylene oxid), poly(2-hydroxethyl methacrylate) and/or poly (2-hydropropyl methacrylate) and poly(isobutylene-co-maleic acid). A variety of osmotic pressure-generating materials and/or water-absorbing materials are described in US 2004/0106914 and US 2004/0015154, both of which are incorporated herein by reference in its entirety.

The osmotic pressure-generating ability of the osmotic pressure-generating material may depend on the solubility of the osmotic pressure-generating material in the osmotic fluid, and/or upon the concentration of the osmotic pressure-generating material in the osmotic fluid, and varying either concentration or solubility may modify the osmotic-pressure generating ability of the osmotic pressure-generating material. Concentration of the osmotic pressure-generating material in the osmotic fluid may be modifiable by a change in solubility of the osmotic pressure-generating material in response to an electromagnetic field control signal or by a change in the osmotic fluid in response to an electromagnetic field control signal.

The osmotic pump system of FIGS. 2A and 2B may include a remotely activatable control element 72 responsive to the electromagnetic field control signal to control the generation of osmotic pressure by the osmotic pressure-generating material 70. As depicted in FIG. 2A, a portion 74 of osmotic pressure-generating material 70 is not in solution. Following activation of remotely activatable control element 72, a larger amount of the osmotic pressure-generating material 70 is in solution, as depicted in FIG. 2B, to produce a higher concentration of osmotic pressure-generating material 70, and thus a larger flow of osmotic fluid 71 into osmotic chamber 62, and an increased pumping rate of delivery fluid 58 out of delivery reservoir 56.

Remotely activatable control elements used in various embodiments of osmotic pump devices and systems may include one or more electromagnetically active material, for example a magnetically active material such as a permanently magnetizable material, a ferromagnetic material, a ferrimagnetic material, a ferrous material, a ferric material, a dielectric material, a ferroelectric material, a piezoelectric material, a diamagnetic material, a paramagnetic material, an antiferromagnetic material, or an electrically active material, such as a permanently 'poled' dielectric, a ferroelectric, a dielectric or a piezoelectric material.

Figure 3:
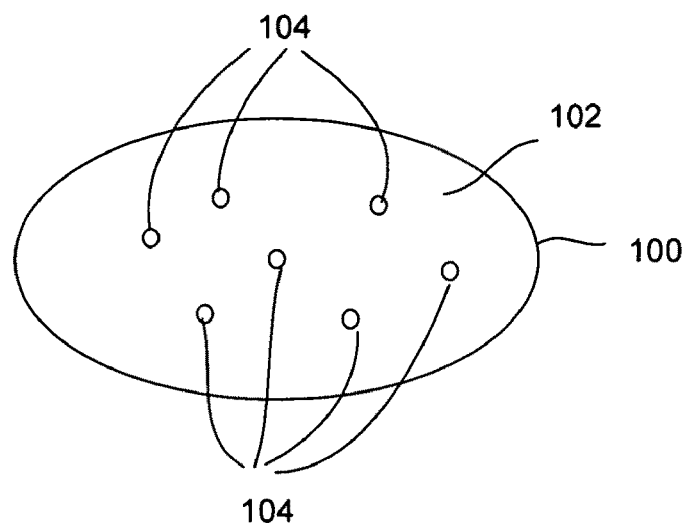
FIG. 3 depicts a remotely activatable element including a plurality of electromagnetically active elements.

Remotely activatable control elements may, in some embodiments, by composite structures. FIG. 3 depicts an example of a remotely activatable control element 100 including a composite structure formed from a polymer 102 and multiple electrically or magnetically active components in the form of multiple particles 104 distributed through polymer 102. In some embodiments, the electrically or magnetically active components may be heatable by the electromagnetic control signal, and heating of the electrically or magnetically active components may cause the polymer to undergo a change in configuration. An example of a magnetically responsive polymer is described, for example, in Neto, et al, "Optical, Magnetic and Dielectric Properties of Non-Liquid Crystalline Elastomers Doped with Magnetic Colloids"; Brazilian Journal of Physics; bearing a date of March 2005; pp. 184-189; Volume 35, Number 1, which is incorporated herein by reference. Other exemplary materials and structures are described in Agarwal et al., "Magnetically-driven temperature-controlled microfluidic actuators"; pp. 1-5; located at: http://www.unl.im.dendai.ac.ip/INSS2004/INSS2004_papers/OralPresentations/C2.pdf or U.S. Pat. No. 6,607,553, both of which are incorporated herein by reference.

In some embodiments, the remotely activatable control element may include a shape memory material, such as a shape memory polymer or a shape memory metal. In other embodiments, the remotely activatable control element may include a bimetallic structure. In still other embodiments, the remotely activatable control element may include a polymer, ceramic, dielectric or metal. In some embodiments, the remotely activatable control element may include at least one of a hydrogel, a ferrogel or a ferroelectric. The remotely activatable control element may include a composite material or structure, such as a polymer and a magnetically or electrically active component.

The response of the remotely activatable control element to an electromagnetic field may be due to absorption of energy from the electromagnetic signal or due to torque or traction on all or a portion of the remotely activatable control element due to the electromagnetic field. The response will depend upon the intensity, the relative orientation and the frequency of the electromagnetic field and upon the geometry, composition and preparation of the material of the remotely activatable control element. A response may occur on the macro level, on a microscopic level, or at a nanoscopic or molecular level.

The remotely activatable control element may have various functional characteristics. In some embodiments, the remotely activatable control element may include or form a heating element (e.g., a resistive element) or a cooling element (which may be, for example, a thermoelectric device). In some embodiments, the remotely activatable control element may be an expanding element. In some embodiments, a remotely activatable control element may include a receiving element such as an antenna or other geometric gain structure to enhance the receiving of an electromagnetic control signal transmitted from a remote control signal generator.

Figure 4:
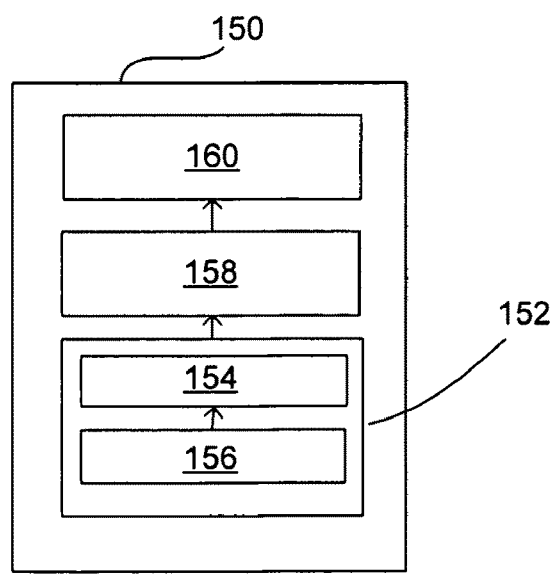
FIG. 4 is a schematic diagram of an embodiment of an osmotic pump device.

FIG. 4 depicts in schematic form an embodiment of an osmotic pump device 150 including a remotely activatable control element 152 that includes an active portion 154 and a receiving element 156. Osmotic pump device 150 also includes osmotic chamber 158 and delivery reservoir 160. The receiving element 156 may be any structure that has a size, shape, and material that is suitable for receiving and transducing electromagnetic energy of a particular frequency or frequency band. In some embodiments, receiving element 156 may be highly frequency-selective, while in other embodiments it may react usefully over a wide frequency band, or over multiple frequency bands. Receiving element 156 may be formed of various metallic or electrically or magnetically active materials. Active portion 154 may include various materials that respond mechanically, thermally or chemically to electromagnetic energy received and transduced by receiving element 156 to influence the generation of osmotic pressure in osmotic chamber 158 or the flow of fluid into osmotic chamber 158 or out of delivery reservoir 160, and consequently to modify the pumping rate of fluid from delivery reservoir 160.

Figure 5A:
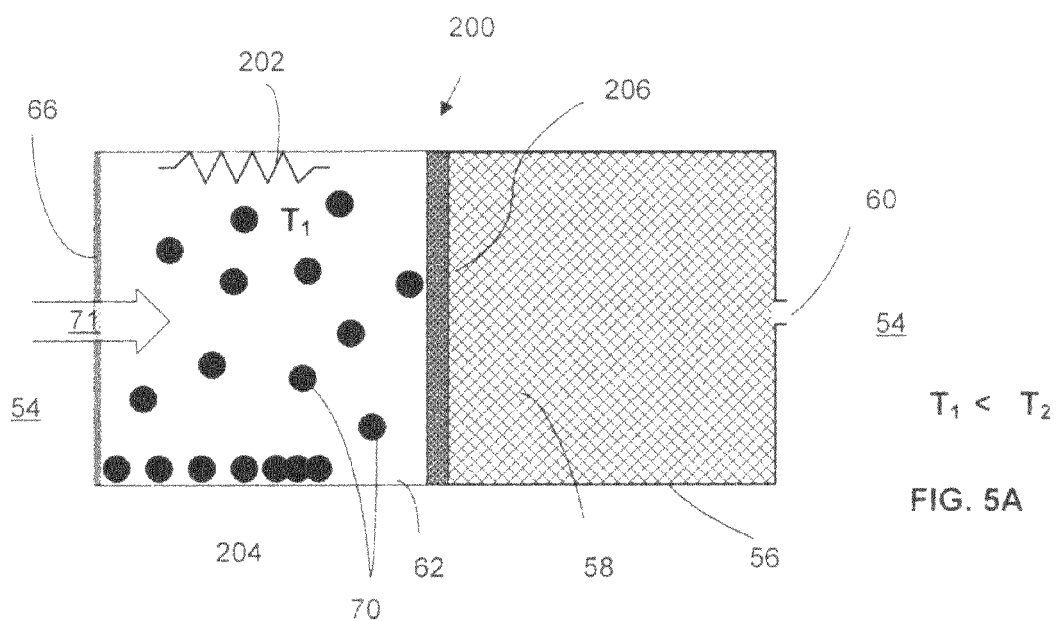
FIGS. 5A and 5B illustrate an embodiment of an osmotic pump device.
Figure 5B:
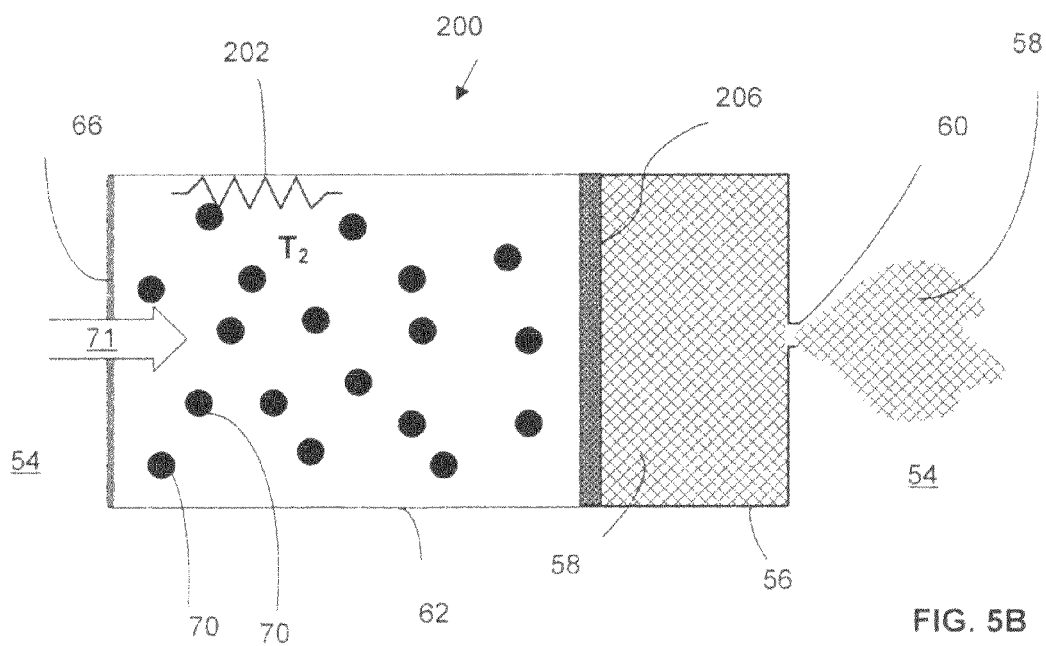

One method by which a remotely activatable control element may respond to the control signal is by producing or by absorbing heat. In some embodiments, a change in temperature of the remotely activatable control element may modify the generation of osmotic pressure directly. As shown in FIGS. 5A and 5B, in one embodiment the osmotic pump system may include an osmotic pump device 200 including a remotely activatable control element 202 that is an electromagnetic field activated heating element capable of producing an increase in temperature in the osmotic fluid, wherein the osmotic pressure-generating material 70 has a solubility in the osmotic fluid 71 that changes in response to an increase in temperature of the osmotic fluid. Osmotic pump device 200 may include an osmotic chamber 62 and delivery reservoir 56 containing delivery fluid 58, which may be ejected through outlet 60. The osmotic pump system 200 includes semi-permeable barrier 66 and osmotic fluid source (e.g. environment 54) as described previously in connection with FIGS. 2A and 2B. Pressure-responsive movable barrier 206 is depicted as a piston or slidable wall, rather than as the flexible membrane shown in FIGS. 2A and 2B, but is substantially functionally equivalent. Osmotic pressure generating material 70 is contained within osmotic chamber 62. Remotely activatable control element 202 may be located in the wall of osmotic chamber 62. Remotely activatable control element 202 has an initial temperature $T_1$. Following heating of remotely activatable control element 202 in response to an electromagnetic control signal, remotely activatable control element 202 has a subsequent temperature $T_2$, as shown in FIG. 5B. The change in temperature of remotely activatable control element 202 may modify the concentration of osmotic pressure generating material 70 within osmotic chamber 62. In FIG. 5A, portion 204 of osmotic pressure-generating material 70 is insoluble, while in FIG. 5B, all of osmotic pressure-generating material 70 has gone into solution, due to the change in temperature of osmotic fluid 71. The electromagnetic field activated heating element 202 may include a ferrous, ferric, or ferromagnetic material, or other material with a significant electromagnetic "loss tangent" or resistivity. In the present example, the solubility of the osmotic pressure-generating material 70 in the osmotic fluid 71 is depicted as increasing with increasing temperature, but in some embodiments, the solubility may decrease with increasing temperature.

In some embodiments, the osmotic pump system may include an electromagnetic field activated cooling element capable of producing a decrease in temperature in the osmotic fluid, wherein the osmotic pressure-generating material has a solubility in the osmotic fluid that changes in response to an decrease in temperature of the osmotic fluid. For example, the electromagnetic field activated cooling element may include a thermoelectric element. The solubility of the osmotic pressure-generating material may increase with decreasing temperature, or it may decrease with decreasing temperature. The concentration of the osmotic pressure-generating material in the osmotic fluid may be modifiable by a change in the volume of the osmotic chamber in response to the electromagnetic field control signal.

Figure 6A:
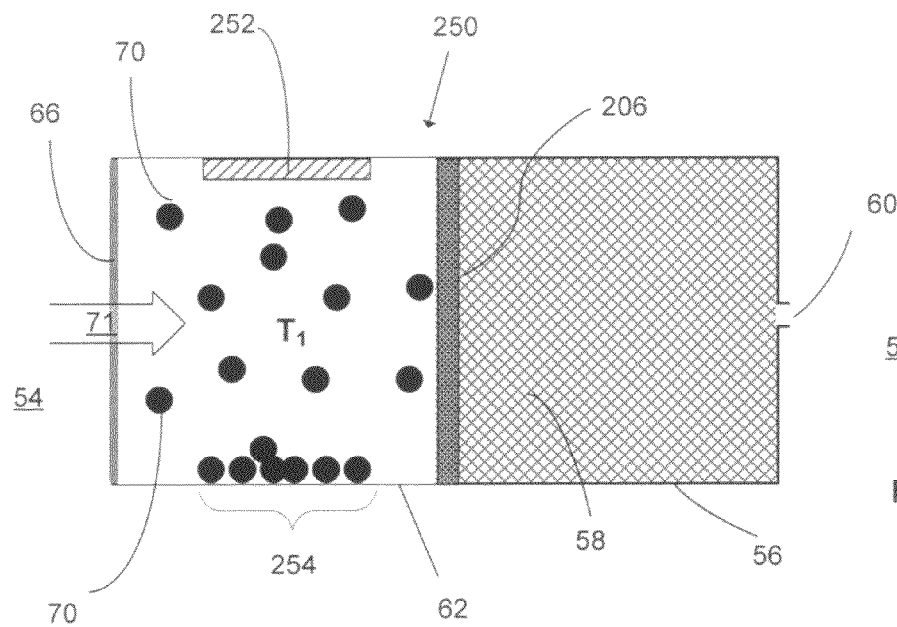
FIGS. 6A and 6B illustrate another embodiment of an osmotic pump device.
Figure 6B:
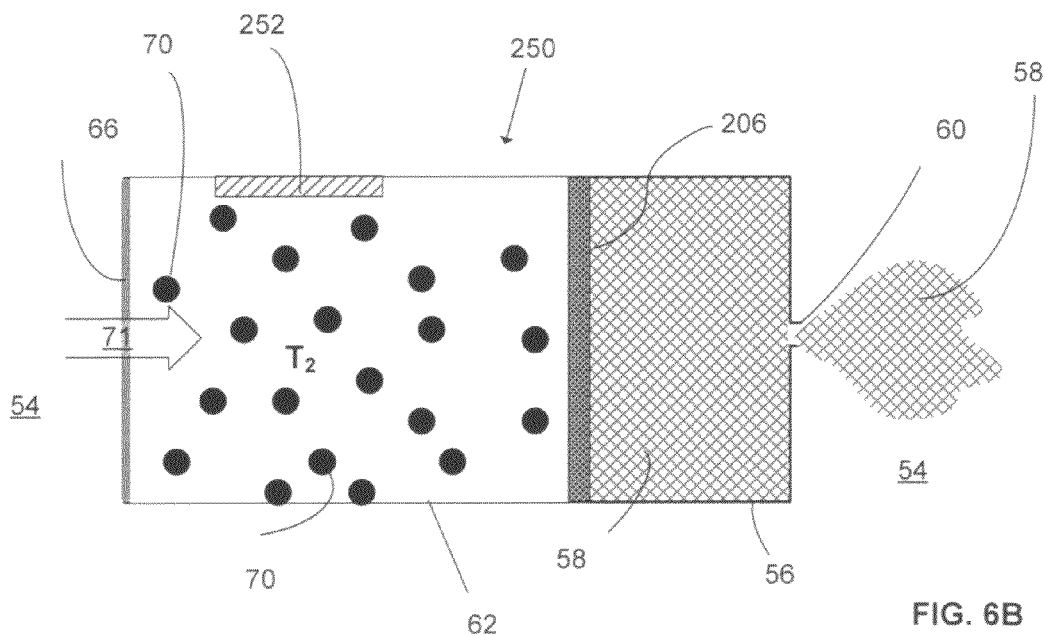

FIGS. 6A and 6B depict an osmotic pump device 250 in which remotely activatable control element 252 responds to an electromagnetic control signal by producing cooling. Methods and/or mechanisms of producing cooling may include, but are not limited to, thermoelectric (Peltier Effect) and liquid-gas-vaporization (Joule-Thomson) devices, or devices which employ "phase-changing" materials involving significant enthalpies of transition. In FIG. 6A, for example, cooling element 252 may be activated to produce cooling to temperature $T_1$, and hence a lower osmotic pressure in osmotic chamber 62. In FIG. 6B, the electromagnetic control signal may be modified so that cooling element 252 no longer produces cooling, and the temperature increases to a higher temperature $T_2$. The pressure in osmotic chamber 62 then increases to produce an increase in the flow of osmotic fluid 71 into osmotic chamber 62, with a corresponding increase in pumping rate of delivery fluid 58 from delivery reservoir 56 into the environment 54, via outlet 60.

Figure 7A:
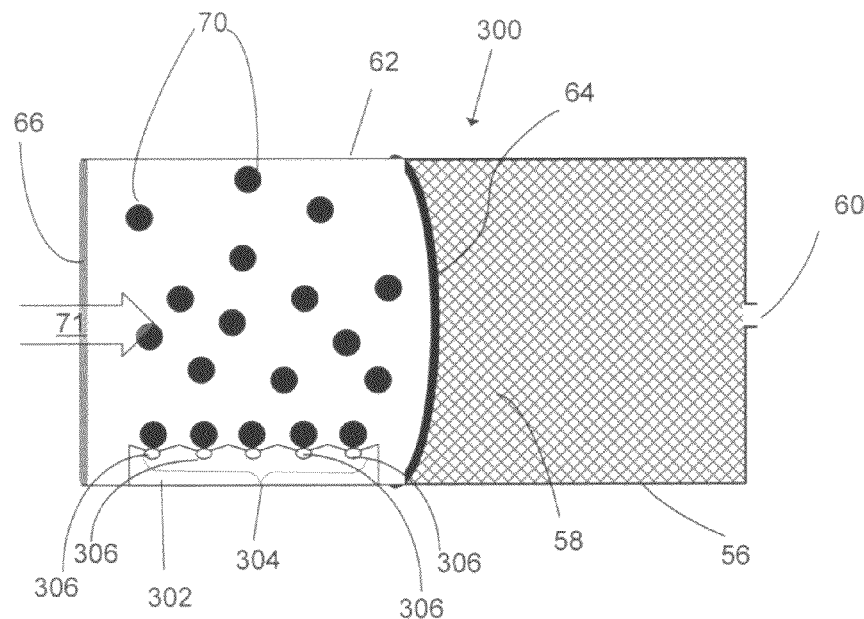
FIGS. 7A and 7B illustrate a further embodiment of an osmotic pump device.
Figure 7B:
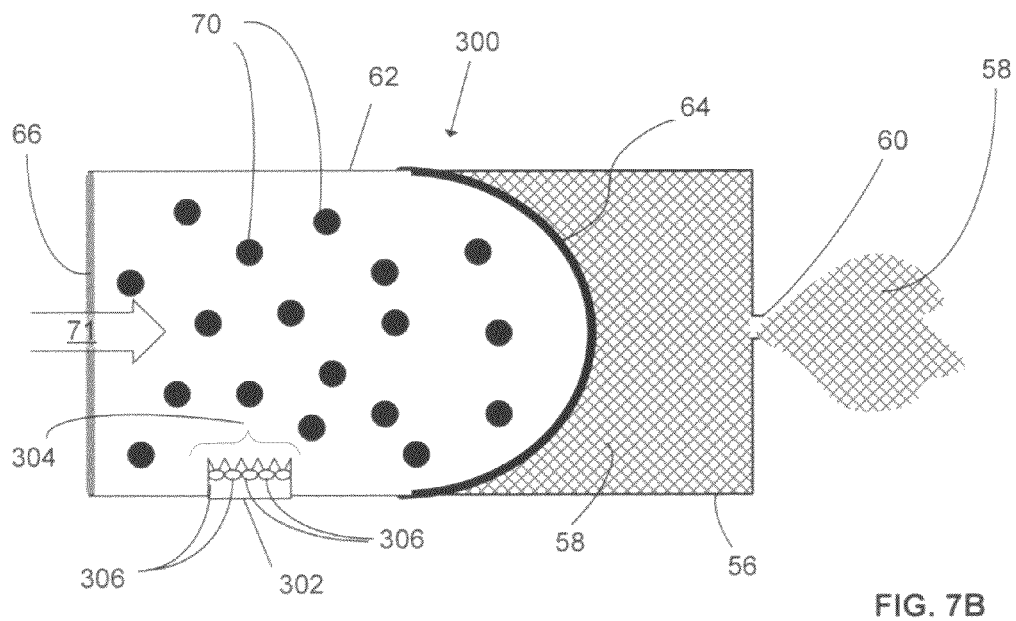

In some embodiments, a change in temperature of a remotely activatable control element of an osmotic pump device element may modify the generation of osmotic pressure, and hence the pumping rate, indirectly, for example by producing a change in dimension of a structure (which may be, for example, similar to the remotely activatable control element depicted in FIG. 3). FIG. 7A depicts osmotic pump system 300, including delivery reservoir 56 containing delivery fluid 58 and osmotic chamber 62 containing osmotic pressure generating material 70, pressure responsive movable barrier 64 and semi-permeable membrane 66, as described previously. Osmotic pump system 300 may include remotely activatable control element 302, which may change in dimension in response to an electromagnetic control signal. The change in dimension may be due to heating, or removal or loss of heat. Remotely activatable control element 302 may be located in the wall of osmotic chamber 62, as depicted in FIGS. 7A and 7B. An interaction region 304 including interaction sites 306 may be located on or adjacent to remotely activatable control element 302, so that the dimension of interaction region 304 is modified with the change in dimension of remotely activatable control element 302. Interaction sites 306 may bind osmotic pressure generating material 70, thus keeping it out of solution, and maintaining a lower osmotic pressure in osmotic chamber 62; a change in spacing or exposure of interaction sites 306 may modify the interaction of osmotic pressure generating material 70 with interaction sites 306, and thus modifies the osmotic pressure in osmotic chamber 62. For example, in FIG. 7B, the remotely activatable control element has contracted in at least one dimension to produce a corresponding decrease in size of interaction region 304, and reduction in spacing between interaction sites 306. In the example depicted in FIG. 7B, the reduction in interaction site spacing reduces interactions with osmotic pressure generating material 70, causing it to go into solution in fluid 71 in higher concentration.

The interaction sites may be localized to an interaction region, as depicted in FIGS. 7A and 7B, or the interaction sites may be distributed to various locations within the osmotic chamber. The osmotic pump may include a plurality of interaction sites for the osmotic pressure-generating material within the osmotic chamber, the likelihood of interaction of the osmotic pressure-generating material with the interaction sites controllable by the electromagnetic field control signal, wherein interaction of the osmotic pressure-generating material with the interaction sites causes a change in osmotic pressure within the osmotic chamber. The interaction sites may be capable of interacting with the osmotic pressure generating material by one or more of binding, reacting, interacting, or forming a complex with the osmotic pressure-generating material. The interaction sites may be responsive to an electromagnetic field control signal by a change in at least one characteristic, the change in the at least one characteristic modifying the interaction between the interaction sites and the osmotic pressure-generating material. The at least one characteristic may include, but is not limited to, at least one of a solubility, a reactivity, a distribution within the osmotic chamber, a density, a temperature, a conformation, an orientation, an alignment, or chemical potential, for example.

At least a portion of the osmotic chamber containing the interaction sites (e.g. interaction region 304 in FIGS. 7A and 7B) may be responsive to an electromagnetic field control signal by a change in the surface area of the portion of the osmotic chamber, the change in surface area modifying at least one of the number of interaction sites or likelihood of interaction of the osmotic pressure-generating material with the interaction sites. The change of surface area may be produced by stretching of the portion of the osmotic chamber, as depicted in FIGS. 8A-8D, or the change of surface area may be produced by unfolding of the portion of the osmotic chamber, as depicted in FIGS. 11A and 11B, or by some of change in conformation of at least a portion of the osmotic chamber.

Figures 8A, 8B:
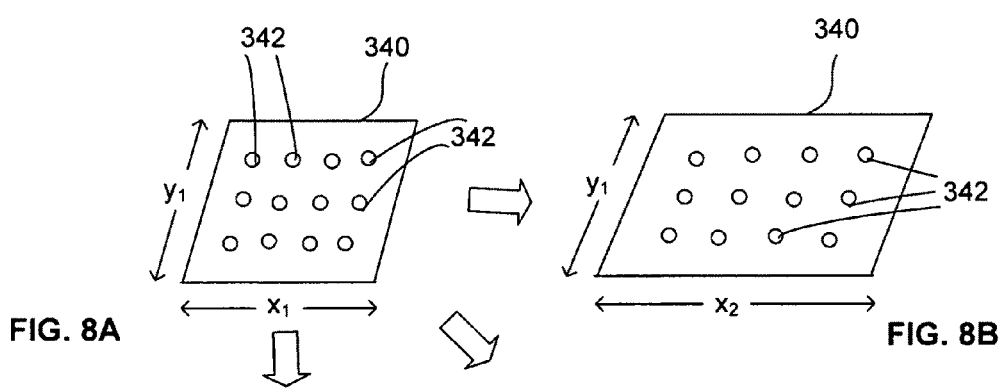
FIG. 8A depicts an exemplary interaction region.
FIG. 8B depicts expansion of the interaction region of FIG. 8A in a first direction.
Figures 8C, 8D:
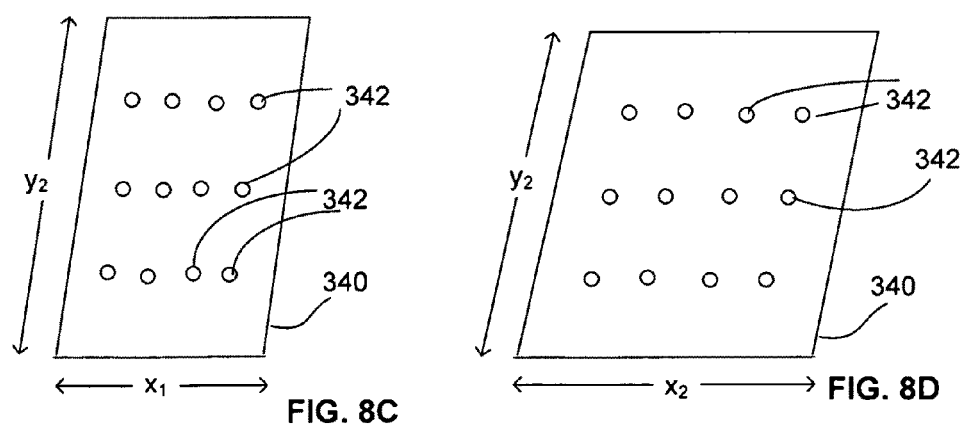
FIG. 8C depicts expansion of the interaction region of FIG. 8A in a second direction.
FIG. 8D depicts expansion of the interaction region of FIG. 8A in first and second directions.

FIGS. 8A-8D depict the effect of changes in one or two dimensions on an interaction region 340. For example, the interaction region may be formed on a remotely activatable control element that expands in response to a control signal. Interaction region 340 may include a plurality of reaction sites 342, and having initial length of $x_1$ in a first dimension and $y_1$ in a second dimension. FIG. 8B depicts interaction region 340 following a change in the first dimension, to a length $x_2$. FIG. 8C depicts interaction region 340 following a change in the second dimension, to a length $y_2$, and FIG. 8D depicts interaction region 340 following a change in both the first and second dimensions, to a size of $x_2$ by $y_2$. In each case, a change in dimension results in a change in distance between reaction sites 342. The dimension change depicted in FIGS. 8A-8D may be viewed as a 'stretching' or 'expansion' of the interaction region. Increasing the surface area of the interaction region may increase the rate of the reaction. Increasing the surface area of the interaction region (e.g., by stretching the surface) may increase the distance between reaction sites on the interaction region. An increased distance between reaction sites may lead to an increase in reaction rate (for example, in cases where smaller spacing between reaction sites leads to steric hindrance that blocks access of reactants to reaction sites).

The influence of modifying the surface area of an interaction region is described further in connection with FIGS. 9A and 9B and 10A and 10B. FIGS. 9A and 9B illustrate how an increase of the surface area of an interaction region by stretching or expansion may increase the rate of the interaction occurring at the interaction region. Multiple interaction sites 352 are located in interaction region 350. As shown in FIG. 9A, prior to stretch or expansion, interaction sites 352 are close together, and reactant 354, which binds to the interaction sites 352, is sufficiently large that it is not possible for reactant 354 to bind to each interaction site 352. When interaction region 350 has been stretched or expanded to expanded form 350' as depicted in FIG. 9B, so that the interaction sites 352 are further apart, it is possible for reactant 354 to bind to a larger percentage of the interaction sites, thus increasing the rate of interaction.

In some embodiments, an increase in the surface area of the interaction region by stretching or expansion may decrease the interaction rate (for example, in cases where a particular spacing is needed to permit binding or association of reactants with several interaction sites simultaneously). FIGS. 10A and 10B illustrate how an increase in the surface area of an interaction region 400 by stretching or expansion may decrease the rate of the interaction occurring at the interaction region. Again, multiple interaction sites 402 and 404 are located in the interaction region 400, as depicted in FIG. 10A. In the present example binding of a reactant 406 to interaction region 400 requires binding of a reactant 406 to two interaction sites 402 and 404. When interaction region 400 is stretched or expanded to expanded form 400' as depicted in FIG. 10B, the spacing of the two interaction sites 402 and 404 is changed so that reactant 406 does not readily bind to interaction region in the expanded form 400', thus reducing the rate of interaction.

Many materials expand when thermal energy is applied. By combining materials as in polymer gels one can use the differing properties of individual components to affect the whole. Thermally-responsive materials include thermally responsive gels (hydrogels) such as thermosensitive N-alkyl acrylamide polymers, Poly(N-isopropylacrylamide) (PNIPAAm), biopolymers, crosslinked elastin-based networks, materials that undergo thermally triggered hydrogelation, memory foam, resin composites, thermochromic materials, proteins, memory shape alloys, plastics, and thermoplastics. Materials that contract or fold in response to heating may include thermally-responsive gels (hydrogels) that undergo thermally triggered hydrogelation (e.g. Polaxamers, uncross-linked PNIPAAm derivatives, chitosan/glycerol formulations, elastin-based polymers), thermosetting resins (e.g. phenolic, melamine, urea and polyester resins), dental composites (e.g. monomethylacrylates), and thermoplastics.

Some examples of reactions that may be sped up by change in distance between reaction sites include those involving drugs designed with spacers, such as dual function molecules, biomolecules linked to transition metal complexes as described in Paschke et al, "Biomolecules linked to transition metal complexes—new chances for chemotherapy"; Current Medicinal Chemistry; bearing dates of October 2003 and Oct. 18, 2005, printed on Oct. 24, 2005; pp. 2033-44 (pp. 1-2); Volume 10, Number 19; PubMed; located at: http://www-w.ncbi.nlm.nih.gov/entrez/query.fcgi?cmd=Retrieve&db=PubMed&list_uids=12871101&dopt=Abstract, and Schiff bases as described in Puccetti et al., "Carbonic anhydrase inhibitors", Bioorg. Med. Chem. Lett. 2005 June 15; 15(12): 3096-101 (Abstract only), both of which are incorporated herein by reference. Other reactions include reactions responding to conformational (allosteric) changes including regulation by allosteric modulators, and reactions involving substrate or ligand cooperativity in multiple-site proteins, where binding affects the affinity of subsequent binding, e.g., binding of a first $O_2$ molecule to Heme increases the binding affinity of the next such molecule, or influence of Tau on Taxol, as described in Ross et al., "Tau induces cooperative Taxol binding to microtubules"; PNAS; Bearing dates of Aug. 31, 2004 and 2004; pp. 12910-12915; Volume 101, Number 35; The National Academy of Sciences of the USA; located at: http://gabriel.physics.ucsb.edu/~deborah/pub/RossPNASv101p12910y04.pdf, which is incorporated herein by reference. Reactions that may be slowed down by increased reaction site spacing include reactions responsive to conformational (allosteric) changes, influence or pH, or crosslinking. See for example Boniface et al., "Evidence for a Conformational Change in a Class II Major Histocompatibility Complex Molecule Occurring in the Same pH Range Where Antigen Binding Is Enhanced"; J. Exp. Med.; Bearing dates of January 1996 and Jun. 26, 2005; pp. 119-126; Volume 183; The Rockefeller University Press; located at: http://www.iem.org also incorporated herein by reference or Sridhar et al., "New bivalent PKC ligands linked by a carbon spacer: enhancement in binding affinity"; J Med. Chem.; Bearing dates of Sep. 11, 2003 and Oct. 18, 2005, printed on Oct. 24, 2005; pp. 4196-204 (pp. 1-2); Volume 46, Number 19; PubMed (Abstract); Located at: http://www.ncbi.nlm.nih.gov/entrez/query.fcgi?cmd=Retrieve&db=PubMed&list_uids=12954072&dopt=Abstract, also incorporated herein by reference.

In addition to increasing surface areas or reaction volumes, expansion of a remotely activatable control element may also have the effect of exposing additional portions of an interaction region or exposing additional functional group to influence a reaction condition. Increasing the surface area of the interaction region by unfolding or other forms of 'opening' of the interaction region structure of at least a portion of the reaction area may increase the number of reaction sites on the interaction region (e.g. by exposing additional reaction sites that were fully or partially hidden or obstructed when the interaction region was in a folded configuration). For example, the area of an interaction region may be increased by the unfolding of at least a portion of the reaction area to expose additional portions of the reaction area, as depicted in FIGS. 11A and 11B. In FIG. 11A, an interaction region 450, which includes or is made up of a remotely activatable control element, can be expanded by unfolding to the form depicted in FIG. 11B. Interaction region 450 has a pleated structure that includes ridges 452a-452e and valleys 454a-454d. Reaction sites 456 may be located in or on ridges 452a-452e and valleys 454a-454d. In the folded form illustrated in FIG. 11A, reaction sites 456 located in valleys 454a-454d are 'hidden' in the sense that reactants may not fit into the narrow valleys to approach those reaction sites, while reaction sites on ridges 452a-452e remain exposed. When interaction region 450 is unfolded to the form shown in FIG. 11B, reaction sites 456 in valleys 454a-456d are exposed, because the open valleys permit access of reactants to the reaction sites in the valleys.

Examples of materials that unfold in response to electromagnetic fields include ionic polymer-metal composites (IPMC) as described in Shahinpoor et al., "Artificial Muscle Research Institute: Paper: Ionic Polymer-Metal Composites (IPMC) As Biomimetic Sensors, Actuators and Artificial Muscles-A Review"; University of New Mexico; printed on Oct. 21, 2005; pp. 1-28; located at: http://www.unm.edu/~amri/paper.html, which is incorporated herein by reference.

Increasing the surface area of the interaction region may decrease the rate of the interaction in some circumstance and increase the rate of interaction in others. Exposure of additional portions of the interaction region may expose additional functional groups that are not reaction sites, but that may produce some local modification to a surface property of the interaction region that in turn modifies the rate or kinetics of the reaction. For example, exposed functional groups may produce at least a local change in pH, surface energy, or surface charge. See, for example, U.S. patent publication 2003/0142901 A1, which is incorporated herein by reference.

A related modification of the interaction region may include an increase in porosity or decrease in density of a remotely activatable control element. An increase in porosity may have a similar effect to the unfolding depicted in FIGS. 11A and 11B with respect to modifying the spacing or exposure of reaction sites, functional groups, etc. See, for example U.S. Pat. Nos. 5,643,246, 5,830,207, and 6,755,621, all of which are incorporated herein by reference.

A change in the spacing of interaction sites may increase or decrease the rate of interaction, or modify another parameter of an interaction, in a manner that depends on the specific reaction and reactants. Heating or cooling of a reaction volume may also modify a chemical reaction by modifying the pressure or the pH or the osmolality or other reaction-pertinent chemical variables within the reaction space.

In some embodiments, the osmotic pump device may include a secondary material within the osmotic chamber, the secondary material having at least one characteristic modifiable by the electromagnetic field control signal, wherein the concentration of the osmotic pressure-generating material is modifiable by a change in the at least one characteristic of the secondary material. The secondary material may include, for example, a material capable of binding, reacting, interacting, or forming a complex with the osmotic pressure-generating material. The at least one characteristic may include at least one of a solubility, a reactivity, a distribution within the osmotic chamber, a density, a temperature, a conformation, an orientation, an alignment, or a chemical potential-modifying mechanism.

In various embodiments as described herein, the interaction region may include interaction sites, which may include a secondary material capable of interacting with or influencing the behavior of the osmotic pressure-generating material. The remotely activatable control element may modify the influence of the secondary material. In some embodiments the secondary material may not be localized to an interaction region, but may be distributed within the osmotic chamber, but responsive to an electromagnetic control signal.

Figures 12A, 12B:
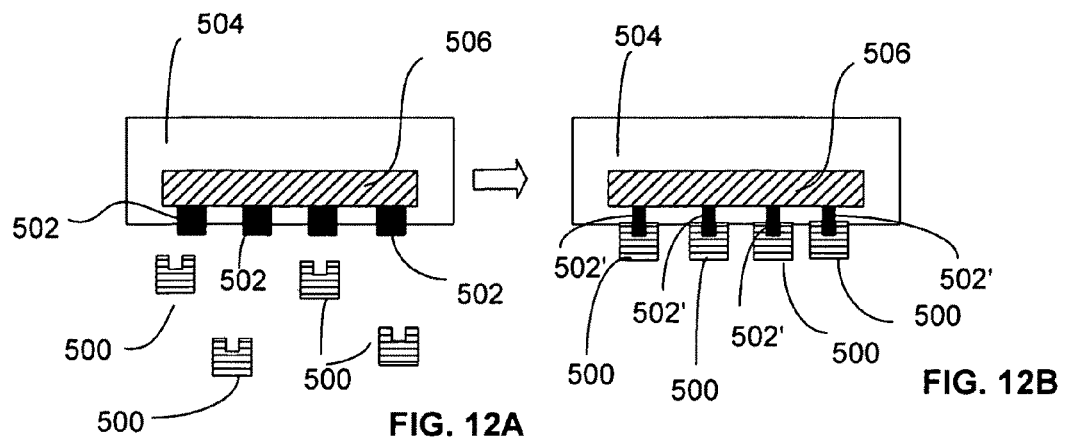
FIGS. 12A and 12B depict an exemplary embodiment of an interaction region.

The secondary material may interact with or influence osmotic pressure generating material in a variety of ways. As a first example, the secondary material may be a receptor or other binding location that binds or sequesters the osmotic pressure generating material, either specifically or non-specifically, to take it out of solution. FIGS. 12A and 12B depict an interaction between osmotic pressure generating material 500 and secondary material 502 in interaction region 504. In FIG. 12A, prior to activation of remotely activatable control element 506, osmotic pressure generating material 500 does not bind to secondary material 502 in interaction region 504. Following activation of remotely activatable control element 506, secondary material 502 undergoes a change to modified form 502' as depicted in FIG. 12B, which allows osmotic pressure generating material 500 to bind to it and go out of solution, thus reducing the osmotic pressure.

Figures 13A, 13B:
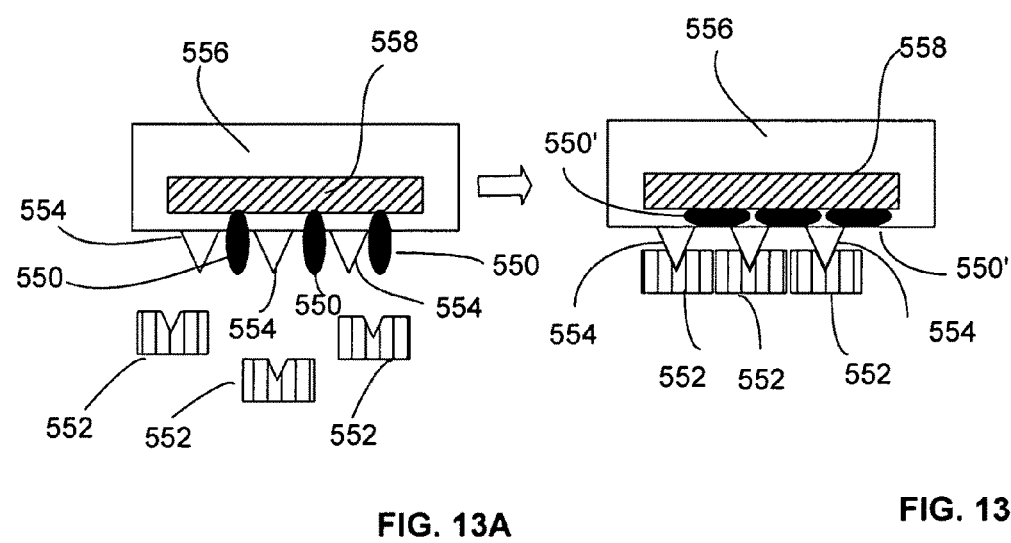
FIGS. 13A and 13B depict another exemplary embodiment of an interaction region.

In the example shown in FIGS. 13A and 13B, secondary material 550 is not itself a receptor or binding site for the osmotic pressure generating material 552, but modifies interaction between the osmotic pressure generating material 552 and an interaction site 554 (which may be, for example, a binding or receptor site) in interaction region 556. In FIG. 13A, the secondary material 550 is in a first configuration which blocks access of osmotic pressure generating material 552 to interaction site 554. In FIG. 13B, under the influence of a remotely activatable control element 558, secondary material 550 has assumed a second configuration 550' which permits access of osmotic pressure generating material 552 to interaction site 554. Secondary material 550 may be a material that modifies the rate or nature of the interaction between osmotic pressure generating material 552 and interaction site 554 in response to an electromagnetic control signal by steric effects, by modifying the polarity of at least a portion of an interaction region, such as e.g., hydrophobic or hydrophilic groups; by modifying the pH of at least a portion of the interaction region, with acids or acidifiers (e.g., ammonium chloride), bases or alkalizers (sodium bicarbonate, sodium acetate) or buffering agents (e.g., mono- or di-hydrogen phosphates); or it may be a material that modifies the charge of at least a portion of the interaction region, such as including various enzyme, neuraminidase, transferase, antioxidants, and charge donors.

Figures 14A, 14B:
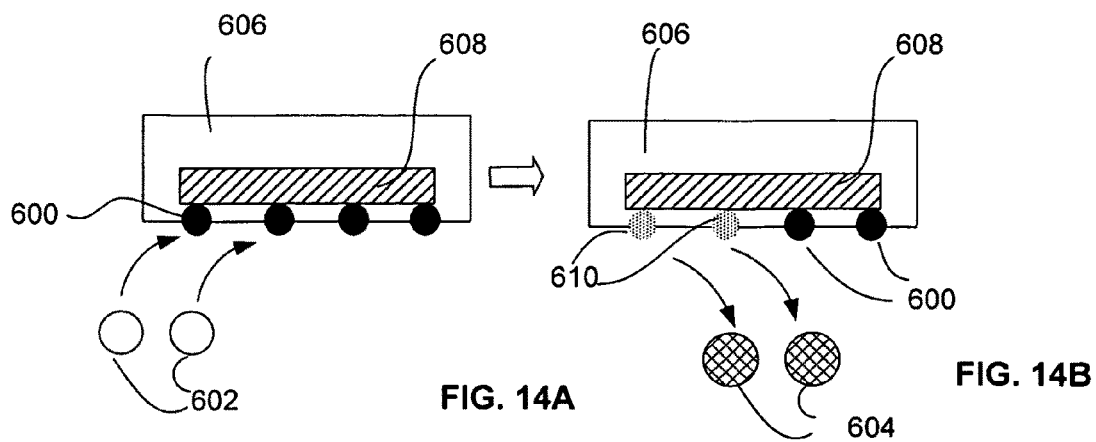
FIGS. 14A and 14B depict another exemplary embodiment of an interaction region.

In the example of FIGS. 14A and 14B, secondary material 600 is a reactant that reacts with osmotic pressure generating material 602 to produce reaction product 604. Osmotic pressure generating material 602 approaches secondary material 600 in interaction region 606 in FIG. 14A, and reaction product 604 leaves interaction region 606 in FIG. 14B. The reaction between secondary material 600 and osmotic pressure generating material 602 is caused, produced, facilitated, or otherwise increased or enhanced by activation of remotely activatable control element 608, (e.g., to produce heating, a cooling, a change in surface charge, conformation, etc.) Reaction product 606 may have a different osmotic pressure generating ability than osmotic pressure generating material 602 due to different solubility, or because the reaction results in an increase or decrease in the number of osmotic pressure generating molecules in the reaction chamber. A reaction by-product 610 may remain at interaction region 606, as depicted in FIG. 13B, or secondary material 600 may be completely consumed by the reaction.

The influence of the remotely activatable control element in the examples depicted in FIGS. 12A-14B may be any of various influences, including but not limited to those described herein; e.g., modifying the temperature of the interaction region or exposing reaction sites or functional groups. The interaction that takes place at the interaction region may change the osmotic pressure within the reaction chamber by changing the concentration of osmotic pressure-generating material within the osmotic chamber by producing reaction products in different quantities or with different solubility or chemical activity than the reactants. In some embodiments, the interaction region may include a catalyst that facilitates a chemical reaction but is not modified by the chemical reaction, for example, metals such as platinum, acid-base catalysts, catalytic nucleic acids such as ribozymes or DNAzymes. The interaction region may include an enzyme, such as an oxidoreductase (e.g. glucose oxidase), transferase (including glycosyltransferase, kinase/phosphorylase), hydrolase, lyase, isomerase, ligase, and enzymatic complexes and/or cofactors. Various examples of catalysts are provided in Kozhevnikov, "Catalysts for Fine Chemical Synthesis, Volume 2, Catalysis by Polyoxometalates"; Chipsbooks.com; Bearing dates of 2002 and 1998-2006, printed on Oct. 21, 2005; pp 1-3 (201 pages); Volume 2; Culinary and Hospitality Industry Publications Services; located at: http://www.chipsbooks.com/catcem2.htm, which is incorporated herein by reference.

Modifying a reaction condition at the interaction region may also be accomplished by heating or cooling at least a portion of the interaction region, or by modifying the osmolality or pH, surface charge, or surface energy of at least a portion of the interaction region. Similarly, modifying a reaction condition at the interaction region may include modifying a parameter of a reaction space within the osmotic pump device, the reaction space containing the interaction region, e.g. by modifying the volume of the reaction space, heating or cooling at least a portion of the reaction space, or modifying the osmolality, pH, pressure, temperature, chemical composition, or chemical activity of at least a portion of the reaction space.

Figure 15A:
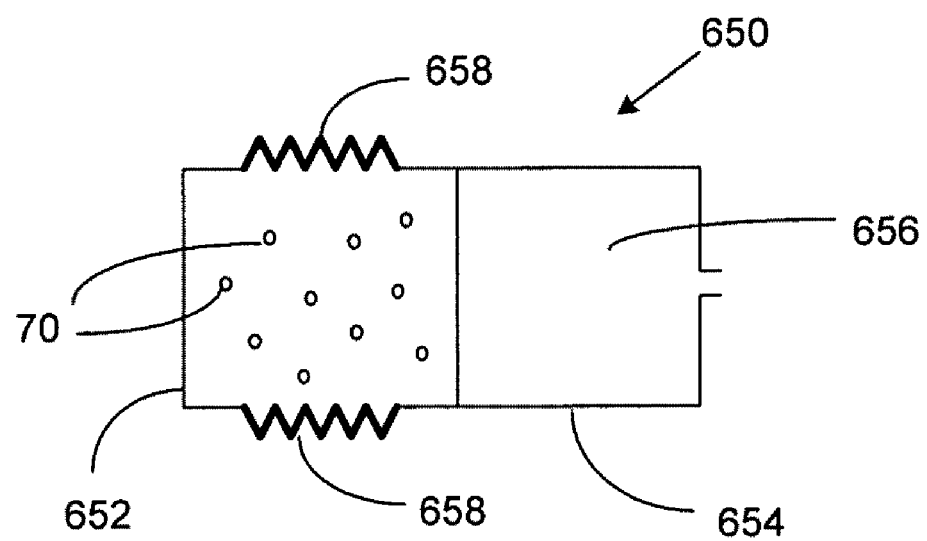
FIGS. 15A and 15B illustrate an increase in volume of an osmotic chamber.
Figure 15B:
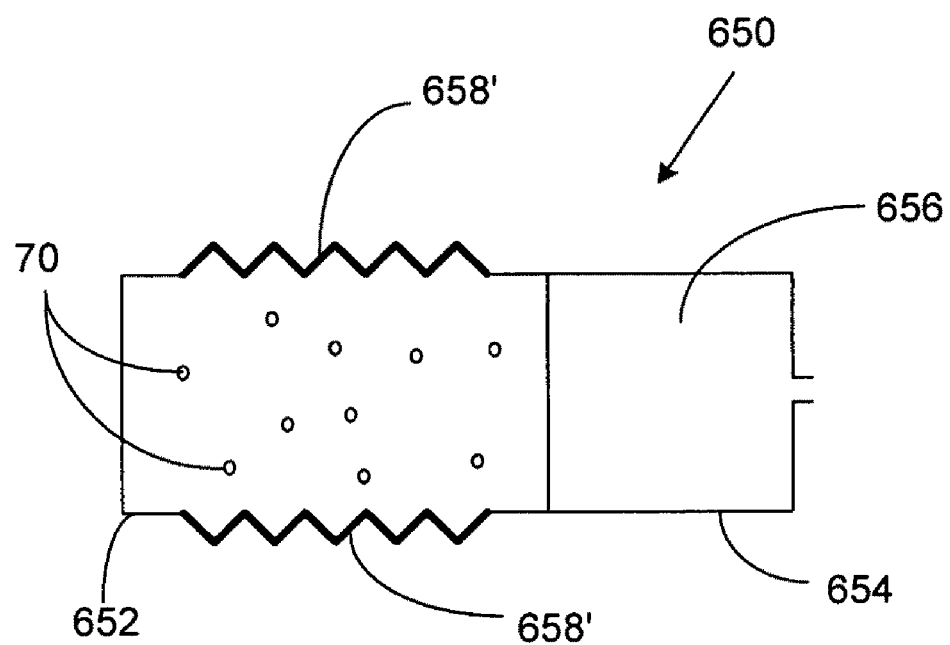

In some embodiments, expansion or other conformation change of a remotely activatable control element may produce other modifications to a chemical reaction. For example, a volume of a reaction space containing the interaction region may be increased by expansion of a remotely activatable control element, as depicted in FIGS. 15A and 15B. An osmotic pump device 650 includes osmotic chamber 652 containing osmotic pressure generating material 70 and having a first volume as shown in FIG. 15A. Osmotic pump device 650 also include delivery reservoir 654 containing a delivery fluid 656. A remotely activatable control element 658 that changes dimension in response to an electromagnetic control signal forms an expandable portion of the wall of osmotic chamber 652. Upon expansion of remotely activatable control element to expanded form 658' shown in FIG. 15B, the volume of reaction space osmotic chamber 652 is increased. The concentration of osmotic pressure-generating material 70 within osmotic chamber 652 is thus decreased, which may have a corresponding influence on the osmotic pumping rate.

The effects illustrated in FIGS. 8A-8D, 11A-11B, and 15A-15B may be reversed by suitable adjustment to the control signal, leading to corresponding decrease in interaction region surface area, volume of the reaction space, or number of exposed reaction sites.

Figure 16:
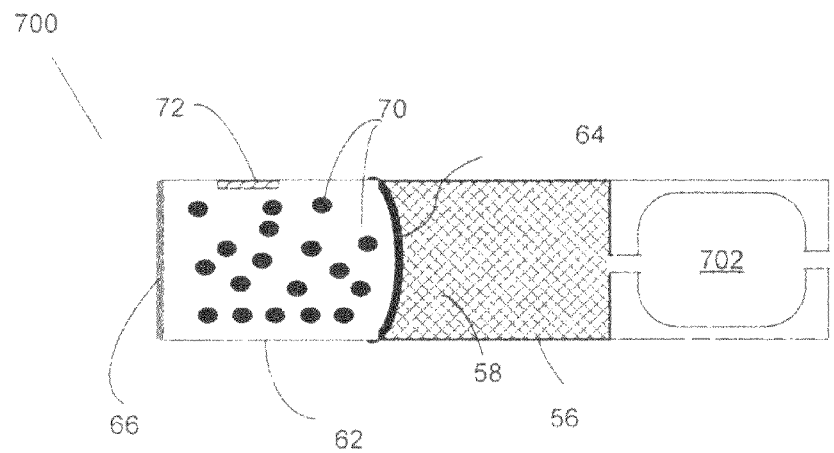
FIG. 16 illustrates an osmotic pump device with a downstream fluid handling structure.

As depicted in various embodiments, e.g., as shown in FIGS. 2A and 2B, 5A and 5B, 6A and 6B, 7A and 7B, and 15A and 15B, the delivery reservoir may include an outlet through which the delivery fluid moves into the environment in response to the change in at least one of pressure or volume in the delivery reservoir. Alternatively, as depicted in FIG. 16, an osmotic pump system 700 may include a downstream fluid handling structure 702 in fluid communication with the delivery reservoir 56 and configured to receive fluid 58 ejected from the delivery reservoir 56 in response to the change in at least one of pressure or volume in the delivery reservoir 56. The downstream fluid handling structure 702 may include a chamber, as depicted in FIG. 16, a channel, or a combination of one or more channels, chambers, or other fluid handling structures. Examples of fluid handling structures suitable for use in selected embodiments are described in U.S. Pat. Nos. 6,146,103 and 6,802,489, and in Krauβ et al., "Fluid pumped by magnetic stress"; Bearing a date of Jul. 1, 2004; pp. 1-3;

located at: http://arxiv.org/PS_cache/physics/pdf/0405/0405025.pdf, all of which are incorporated herein by reference. Fluid handling structures may include, but are not limited to, channels, chambers, valves, mixers, splitters, accumulators, pulse-flow generators, and surge-suppressors, among others.

Figure 17:
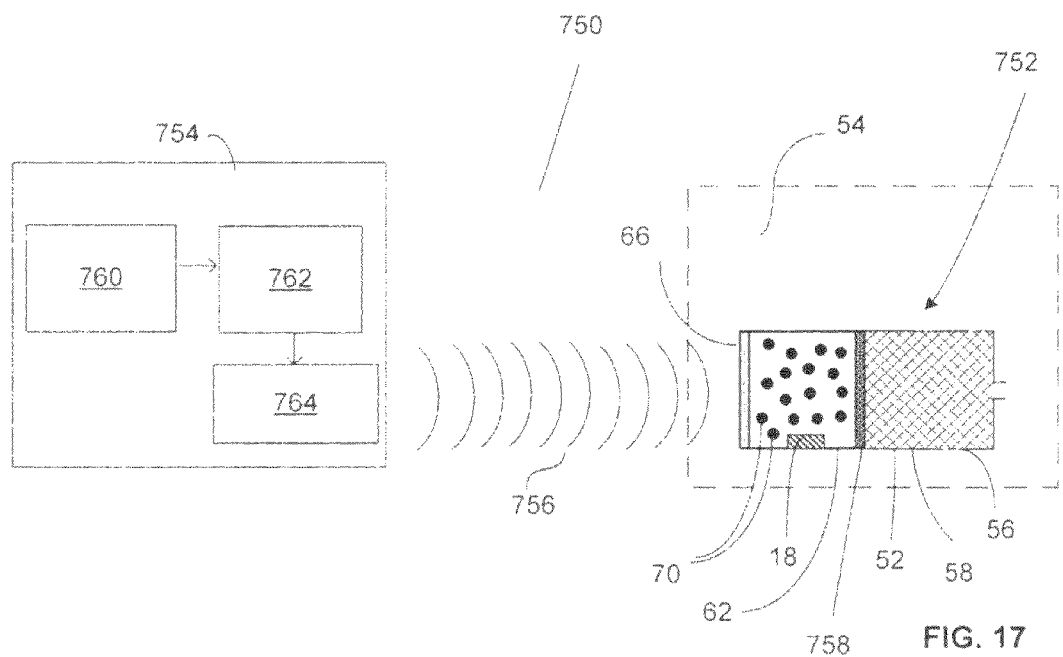
FIG. 17 is a schematic diagram of an osmotic pump system including a remote controller.

FIG. 17 is a schematic diagram of an embodiment of an osmotic pump system 750, which may include an osmotic pump device 752 and a remote control signal source 754 capable of generating an electromagnetic field control signal 756 sufficient to control the generation of osmotic pressure by the osmotic pressure-generating material 70 within the osmotic chamber 62 of the osmotic pump device 752. The osmotic pump device 752 may include a body structure 52 configured for placement in an environment 54; a delivery reservoir 56 capable of containing a delivery fluid 58 to be delivered into the environment 54; osmotic chamber 62; osmotic pressure-generating material 70 contained within the osmotic chamber, the generation of osmotic pressure by the osmotic pressure-generating material 70 controllable by an electromagnetic field control signal 756; a pressure-responsive movable barrier 758 separating the osmotic chamber 62 from the delivery reservoir 56, the pressure-responsive barrier 758 being substantially impermeable to the osmotic pressure-generating material 70 and configured to move in response to a change in pressure in the osmotic chamber 62 to produce a change in at least one of pressure or volume in the delivery reservoir 56; and a semi-permeable membrane 66 separating the osmotic chamber 62 from an osmotic fluid source, the semi-permeable membrane 66 being substantially permeable to fluid from the osmotic fluid source but substantially impermeable to the osmotic pressure-generating material.

The remote control signal source 754 may include electrical circuitry 760, signal generator 762, and signal transmitter 764, and may be configured to produce an electromagnetic control signal 756 having various characteristics, depending upon the intended application of the system. Design specifics of electrical circuitry 760, signal generator 762, and signal transmitter 764 will depend upon the type of electromagnetic control signal 756. The design of circuitry and related structures for generation and transmission of electromagnetic signals can be implemented using tools and techniques known to those of skill in the electronic arts. See, for example, Electrodynamics of Continuous Media, $2^{nd}$ Edition, by L. D. Landau, E. M. Lifshitz and L. P. Pitaevskii, Elsevier Butterworth-Heinemann, Oxford, especially but not exclusively pp. 1-13- and 199-222, which is incorporated herein by reference, for discussion of theory underlying the generation and propagation of electrical, magnetic, and electromagnetic signals. The electronic circuitry may include any or all of analog circuitry, digital circuitry, one or more microprocessors, computing devices, memory devices, and so forth. Remote control signal source 754 may include at least one of hardware, firmware, or software configured to control generation of the electromagnetic control field signal.

The osmotic pump device 752 of the osmotic pump system may include a body structure 52 adapted for positioning in an environment selected from a body of an organism, a body of water or other fluid, or a contained fluid volume. In some embodiments, the body structure may be adapted for positioning in a contained fluid volume selected from an industrial fluid volume, an agricultural fluid volume, a swimming pool, an aquarium, a drinking water supply, and an HVAC system cooling water supply. Various embodiments may be used in connection with selected biomedical applications (e.g., with osmotic pump devices adapted for placement in the body of a human or other animal). It is also contemplated that osmotic pump systems as described herein may be used in a variety of environments, not limited to the bodies of humans or other animals. Osmotic pump devices may be placed in other types of living organisms (e.g., plants). Osmotic pump devices may also be placed in bodies of water, or in various enclosed fluid volumes, in industrial, agricultural, and various other types of applications. The environments for use of embodiments described herein are merely exemplary, and the osmotic pump systems as disclosed herein are not limited to use in the exemplary applications.

Figure 18:
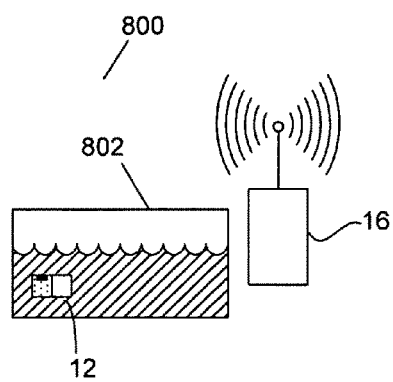
FIG. 18 illustrates an embodiment of a system including a remotely controlled osmotic pump device.

FIG. 18 illustrates an exemplary embodiment of an osmotic pump system 800 in which an osmotic pump device 12 is located in a small enclosed fluid volume 802 (e.g., an aquarium). A remote controller or remote control signal generator 16 is located outside enclosed fluid volume 802.

Figure 19:
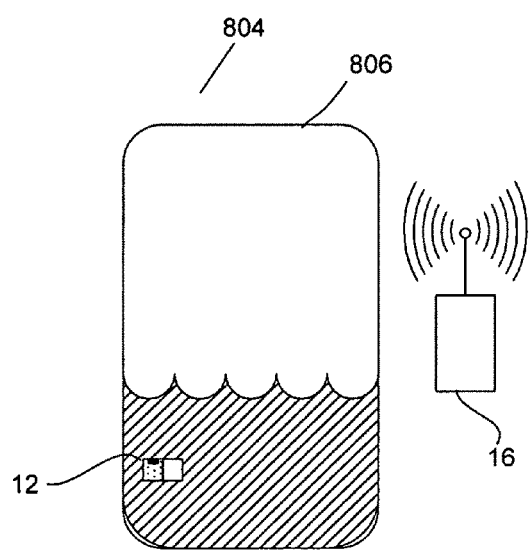
FIG. 19 illustrates an embodiment of a system including a remotely controlled osmotic pump device.

FIG. 19 illustrates a further exemplary embodiment of an osmotic pump system 804 in which an osmotic pump device 12 is located in a larger enclosed fluid volume 806 (which may be, for example, a water storage tank, an HVAC system cooling water tank, a tank containing an industrial fluid or an agricultural fluid). A remote controller or remote control signal generator 16 is located outside enclosed fluid volume 1001.

Figure 20:
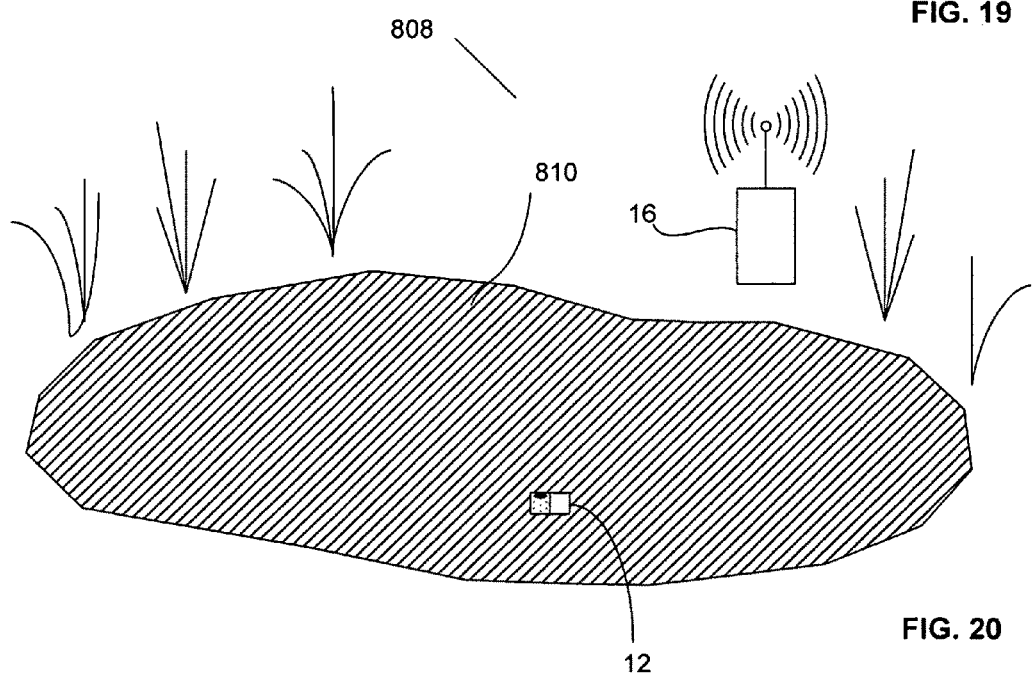
FIG. 20 illustrates an embodiment of a system including a remotely controlled osmotic pump device.

FIG. 20 illustrates a further exemplary embodiment of an osmotic pump system 808 in which an osmotic pump device 12 is located in a body of water 810 (a lake or pond is depicted here, but such osmotic pump systems may also be designed for use in rivers, streams, or oceans). The remote controller or remote control signal generator 16 is shown located outside of body of water 810, though in some embodiments it may be advantageous to place remote controller 16 at a location within body of water 810.

A wide variety of materials may be stored in a delivery reservoir of osmotic pump devices as described herein, and the choice of material will depend upon the use environment and intended application for the osmotic pump device. Materials which may be delivered into an environment by an osmotic pump device may include, but are not limited to, fertilizers, nutrients, remediation agents, antibiotics/microbicides, herbicides, fungicides, disinfectants, materials for adjusting a chemical composition or pH, such as buffers, acids, bases, chelating agents, and surfactant, etc. Examples of materials that may be delivered into the body of an organism include nutrients, hormones, growth factors, medications, therapeutic compounds, enzymes, genetic materials, vaccines, vitamins, imaging agents, cell-signaling materials, pro- or anti-apoptotic agents, or neurotransmitters. Materials may also include precursors or components of certain materials such as genetic materials, vaccines, nutrients, vitamins, imaging agents, therapeutic compounds, hormones, growth factors, pro- or anti-apoptotic agents, or neurotransmitters. Such precursors, may include, for example, prodrugs (see, e.g., "Liver-Targeted Drug Delivery Using HepDirect1 Prodrugs," Erion et al., Journal of Pharmacology and Experimental Therapeutics Fast Forward, JPET 312:554-560, 2005 (first pub Aug. 31, 2004) and "LEAPT: Lectin-directed enzyme-activated prodrug therapy", Robinson et al., PNAS Oct. 5, 2004 vol. 101, No. 40, 14527-14532, published online before print Sep. 24, 2004 (http://www.pnas.org/cgi/content/full/101/40/14527), both of which are incorporated herein by reference. Beneficial materials may be produced, for example, by conversion of pro-drug to drug, enzymatic reaction of material in bloodstream (CYP450, cholesterol metabolism, e.g., with cholesterol monooxygenase, cholesterol reductase, cholesterol oxidase). The term "delivery fluid" as used herein, is intended to cover materials having any form that exhibits fluid or fluid-like behavior, including liquids, gases, powders or other solid particles in a liquid or gas carrier. The delivery fluid may be a solution, suspension, or emulsion. Materials to be delivered into the environment may have suitable fluid properties in some cases, while in other cases the material of interest may be delivered in a fluid solvent or carrier, in solution, suspension, or emulsion, as noted above, or in a gaseous or solid carrier material.

An osmotic pump device as depicted in FIG. 17 may include a remotely activatable control element responsive to the electromagnetic field control signal to control the generation of osmotic pressure by the osmotic pressure-generating material. The remotely activatable control element may include a magnetically or electrically active material including at least one of a permanently magnetizable material, a ferromagnetic material, a ferrimagnetic material, a ferrous material, a ferric material, a dielectric or ferroelectric or piezoelectric material, a diamagnetic material, a paramagnetic material, and an antiferromagnetic material. The remotely activatable control element may include a polymer, ceramic, dielectric or metal. In some embodiments, the osmotic pump system may include a shape memory material. In some embodiments, the remotely activatable control element may include a polymer and a magnetically or electrically active component.

In some embodiments, the remotely activatable control element may respond to the control signal by changing shape. In some embodiments, the remotely activatable control element may respond to the control signal by changing in at least one dimension. The response of the remotely activatable control element may include one or more of heating, cooling, vibrating, expanding, stretching, unfolding, contracting, deforming, softening, or folding globally or locally. The remotely activatable control element may include various materials, such as polymers, ceramics, plastics, dielectrics or metals, or combinations thereof. The remotely activatable control element may include a shape memory material such as a shape memory polymer or a shape memory metal, or a composite structure such as a bimetallic structure. The remotely activatable control element may include a magnetically or electrically active material. Examples of magnetically active materials include permanently magnetizable materials, ferromagnetic materials such as iron, nickel, cobalt, and alloys thereof, ferrimagnetic materials such as magnetite, ferrous materials, ferric materials, diamagnetic materials such as quartz, paramagnetic materials such as silicate or sulfide, and antiferromagnetic materials such as canted antiferromagnetic materials which behave similarly to ferromagnetic materials; examples of electrically active materials include ferroelectrics, piezoelectrics and dielectrics having both positive and negative real permittivities. In some embodiments, the remotely activatable control element may include a hydrogel or a ferrogel.

In some embodiments, the remotely activatable control element may include a polymer and an electrically active component (including highly polarizable dielectrics) or a magnetically active component (including ferropolymers and the like) as well as remotely activatable control elements including one (or possibly more) large magnetically or electrically active components. In embodiments in which the remotely activatable control element includes one or more electrically or magnetically active components, the electrically or magnetically active component may respond to an electromagnetic control signal in a first manner (e.g., by heating) and the response of the remotely activatable control element may be produced in response to the electrically or magnetically active component (e.g. expansion or change in shape in response to heating of the electrically or magnetically active component).

Various types and frequencies of electromagnetic control signals may be used in osmotic pump systems as described herein. For example, in some embodiments, the osmotic pump system may include a remote control signal source configured to generate a static or quasi-static electrical field control signal or static or quasi-static magnetic field control sufficient to activate the remotely activatable control element to control the generation of osmotic pressure in a desired manner. In other embodiments, the remote control signal source may be configured to generate a radio-frequency, microwave, infrared, millimeter wave, optical, or ultraviolet electromagnetic field control signal sufficient to activate the remotely activatable control element to control the generation of osmotic pressure in a desired manner.

A remote controller for an osmotic pump device may include an electromagnetic signal generator capable of producing an electromagnetic signal sufficient to activate a remotely activatable control element of an osmotic pump device located in an environment to change a concentration of an osmotic pressure-generating material within an osmotic chamber of the osmotic pump device; and an electromagnetic signal transmitter capable of wirelessly transmitting the electromagnetic signal to the remotely activatable control element.

Referring back to FIG. 17, signal transmitter 764 may include a sending device which may be, for example, an antenna or waveguide suitable for use with an electromagnetic signal. Static and quasistatic electrical fields may be produced, for example, by charged metallic surfaces, while static and quasistatic magnetic fields may be produced, for example, by passing current through one or more wires or coils, or through the use of one or more permanent magnets, as known to those of skill in the art. As used herein, the terms transmit, transmitter, and transmission are not limited to only transmitting in the sense of radiowave transmission and reception of electromagnetic signals, but are also applied to wireless coupling and/or conveyance of magnetic signals from one or more initial locations to one or more remote locations.

The remote control signal source 754 as depicted generally in FIG. 17 may be configured to produce an electromagnetic control signal having various characteristics, depending upon the intended application of the system. In some embodiments, a specific remote control signal source may be configured to produce only a specific type of signal (e.g., of a specific frequency or frequency band) while in other embodiments, a specific remote control signal source may be adjustable to produce a signal having variable frequency content. Signals may include components which contribute a DC bias or offset in some cases, as well as AC frequency components. The remote control signal source 754 of the osmotic pump system 750 may be configured to generate a static or quasi-static electrical field control signal or static or quasi-static magnetic field control signal sufficient to activate a remotely activatable control element 18 to produce a desired osmotic pressure or pumping rate. In other embodiments, the remote control signal source 754 may be configured to generate an electromagnetic control signal at various different frequencies sufficient to activate the remotely activatable control element 18 to produce a desired rate or kinetics of the chemical reaction. Electromagnetic control signals may have radio-frequency, microwave, infrared, millimeter wave, optical, or ultraviolet frequencies, for example. Generation of radio frequency electromagnetic signals is described, for example, in *The ARRL*

*Handbook for Radio Communications* 2006, R. Dean Straw, Editor, published by ARRL, Newington, Conn., which is incorporated herein by reference.

The remote controller/remote control signal source (e.g., 754 in FIG. 17) may be modified as appropriate for its intended use. For example, it may be configured to be wearable on the body of a human (or other organism) in which an osmotic pump device has been deployed, for example on a belt, bracelet or pendant, or taped or otherwise adhered to the body of the human. Alternatively, it may be configured to be placed in the surroundings of the organism, e.g., as a table-top device for use in a home or clinical setting.

Various types of electromagnetic field control signals may be used to activate the remotely activatable control element. The remotely activatable control element may be responsive to a static or quasi-static electrical field or a static or quasi-static magnetic field. It may be responsive to various types of non-ionizing electromagnetic radiation, or in some cases, ionizing electromagnetic radiation. Electromagnetic field control signals that may be used in various embodiments include radio-frequency electromagnetic radiation, microwave electromagnetic radiation, infrared electromagnetic radiation, millimeter wave electromagnetic radiation, optical electromagnetic radiation, or ultraviolet electromagnetic radiation.

The electromagnetic signal generator may include electrical circuitry and/or a microprocessor. In some embodiments, the electromagnetic signal may be produced at least in part according to a pre-determined activation pattern. The remote controller may include a memory capable of storing the pre-determined activation pattern. In some embodiments, the electromagnetic signal may be produced based on a model-based calculation; the remote controller may include a memory capable of storing model parameters used in the model-based calculation.

Figure 21:
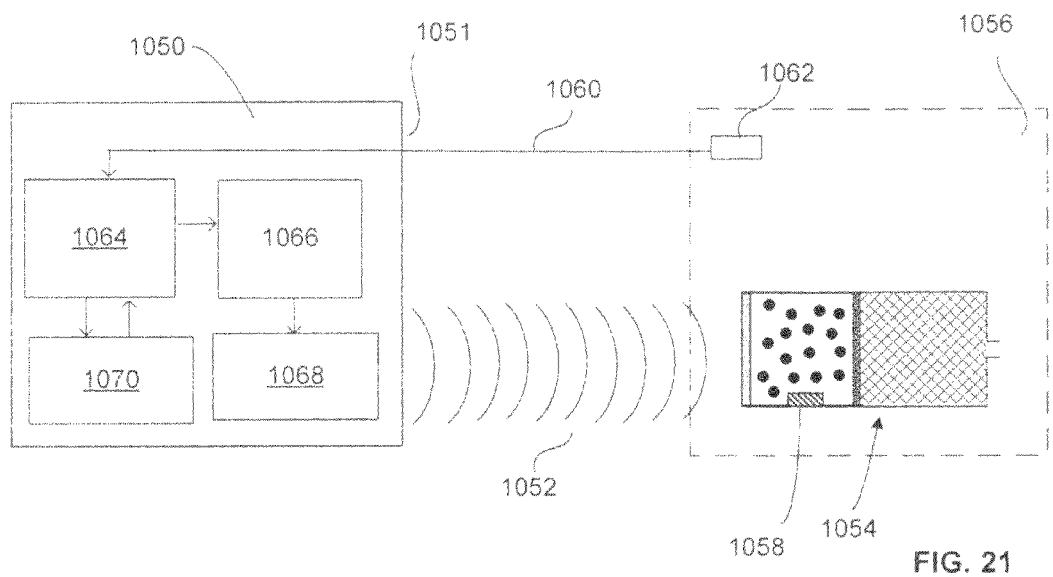
FIG. 21 depicts an embodiment of a system including a remote control device, an osmotic pump device, and a sensor.

FIG. 21 illustrates an osmotic pump system including a remote controller 1050 that produces electromagnetic control signal 1052 that is transmitted to osmotic pump device 1054 in environment 1056. Electromagnetic control signal 1052 is received by remotely activatable control element 1058 in osmotic pump device 1054. Remote controller 1050 may include a signal input 1051 adapted for receiving a feedback signal 1060 sensed from an environment 1056 by a sensor 1062, wherein the electromagnetic signal 1052 is produced based at least in part upon the feedback signal 1060 sensed from the environment. For example, the feedback signal 1052 may correspond to the osmolality or the pH of the environment, the concentration or chemical activity of a chemical in the environment, a temperature or pressure of the environment, or some other sensed signal. Remote controller 1050 may include electrical circuitry 1064, signal generator 1066, signal transmitter 1068, and memory 1070. Feedback from sensor 1062 may be sent over a wire connection or, in some embodiments, transmitted wirelessly.

Figure 22:
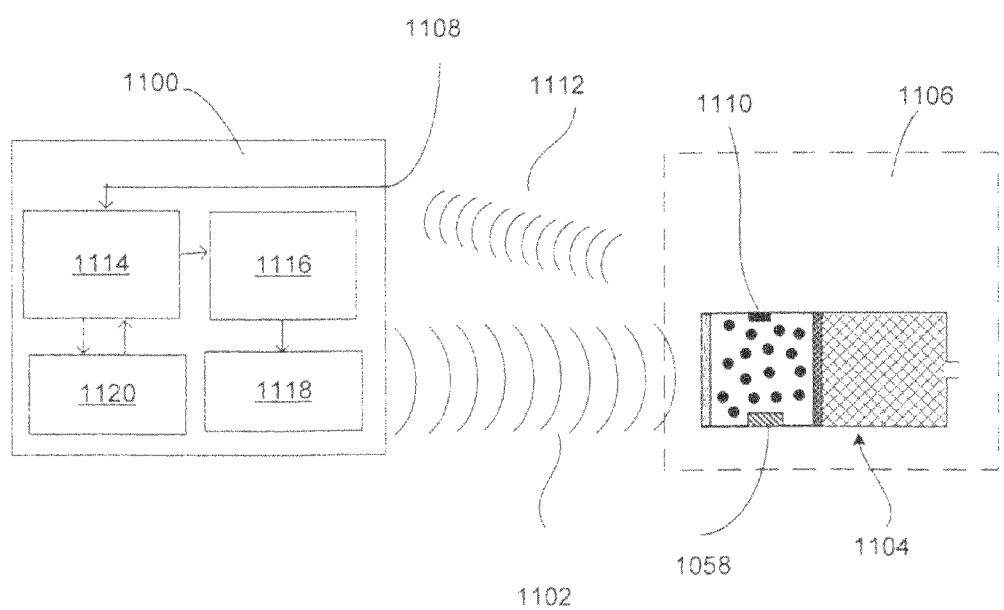
FIG. 22 depicts an embodiment of a system including a remote control device and an osmotic pump device including a sensor.

FIG. 22 illustrates another embodiment of an osmotic pump system, including remote controller 1100, which transmits electromagnetic control signal 1102 to osmotic pump device 1104 in environment 1106. Remote controller 1100 may include a signal input 1108 adapted for receiving a feedback signal 1112 from sensor 1110 in osmotic pump device 1104. The electromagnetic signal 1102 may be determined based at least in part upon the feedback signal 1112. Examples of sensors are described in U.S. Pat. No. 6,935,165, and U.S. Patent Publication 2004/0007051, both of which are incorporated herein by reference. Osmotic pump device 1104 includes remotely activatable control element 1058. Feedback signal 1112 may be transmitted wirelessly back to remote controller 1100. Remote controller 1100 may include processor 1114, signal generator 1116, signal transmitter 1118, and memory 1120. In some embodiments, the remote controller 1100 may include a signal input 1108 adapted for receiving a feedback signal from the osmotic pump device, wherein the electromagnetic signal is produced based at least in part upon the feedback signal sensed from the osmotic pump device. A feedback signal from the osmotic pump device may correspond to the osmolality or the pH within or around the osmotic pump device, the concentration or chemical activity of a chemical within or around the osmotic pump device, a temperature or pressure within or around the osmotic pump device, the pumping rate of the osmotic pump device, or some other parameter sensed from the osmotic pump device.

Figure 23:
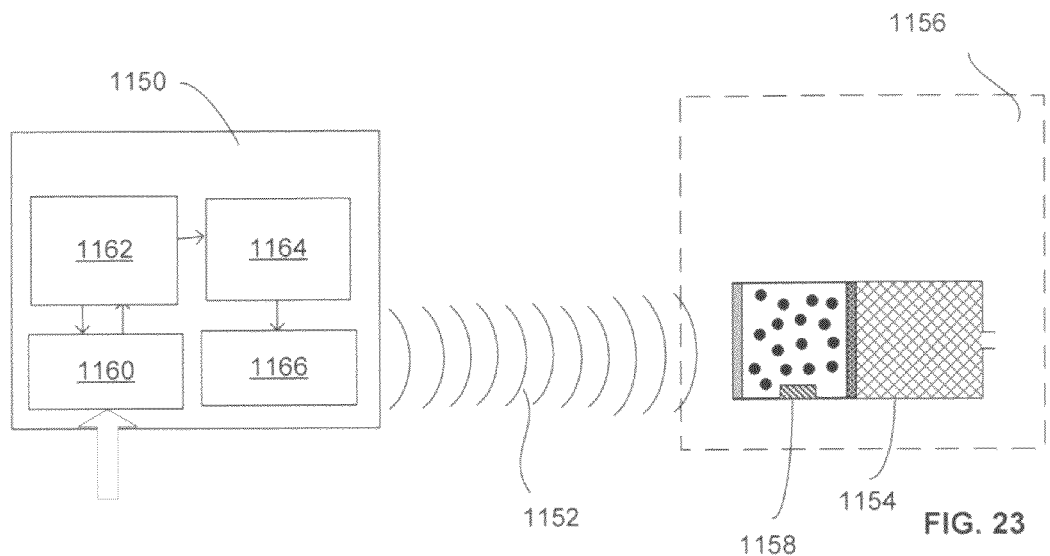
FIG. 23 depicts an embodiment of a system including a remote control device and an osmotic pump device.

As illustrated in FIG. 23, in some embodiments, the remote controller may be configured to receive user input of control parameters. Remote controller 1150 includes input 1160 for receiving input of information or instructions from a user such as, for example, commands, variables, durations, amplitudes, frequencies, waveforms, data storage or retrieval instructions, patient data, etc. As in the other embodiments, remote controller 1150 transmits electromagnetic control signal 1152 to osmotic pump device 1154 in environment 1156, where it activates remotely activatable control element 1158. Input 1160 may include one or more input devices such as a keyboard, keypad, microphone, mouse, etc. for direct input of information from a user, or input 1160 may be any of various types of analog or digital data inputs or ports, including data read devices such as disk drives, memory device readers, and so forth in order to receive information or data in digital or electronic form. Data or instructions entered via input 1160 may be used by electrical circuitry 1162 to modify the operation of remote controller 1150 to modulate generation of an electromagnetic control signal 1152 by signal generator 1164 and transmission of the control signal 1152 by transmitter 1166.

In this and other embodiments disclosed herein, the remote controller may include software, which may include, for example, instructions for controlling the generation of the electromagnetic control signal and instructions for controlling the transmission of the electromagnetic control signal to the electromagnetically responsive control element.

Figure 24:
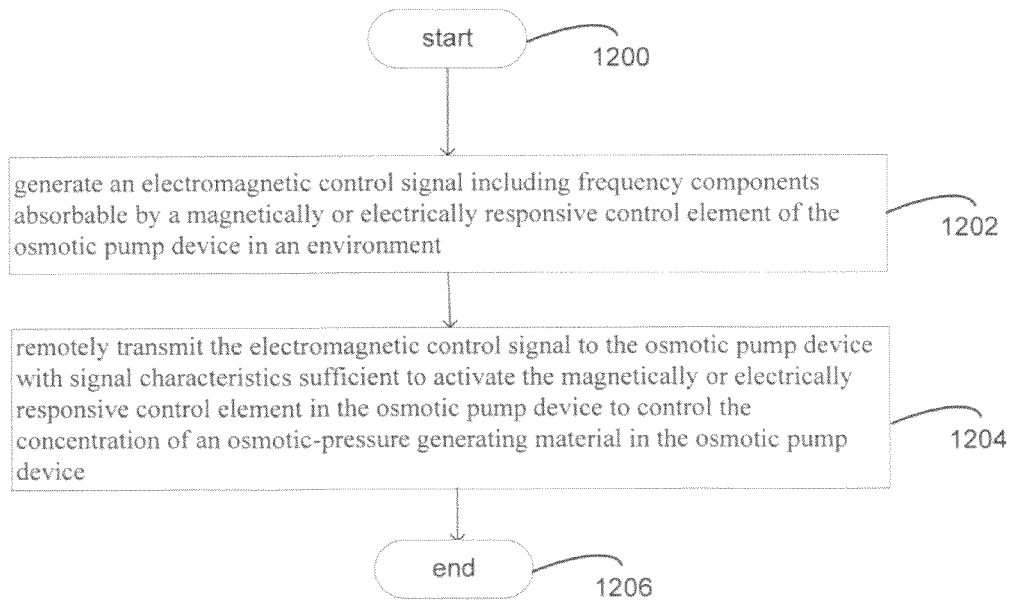
FIG. 24 is a flow diagram of an embodiment of a method of controlling an osmotic pump device.

Osmotic pump devices as disclosed herein may be controlled by a method as illustrated in FIG. 24, which may include generating an electromagnetic control signal including frequency components absorbable by a magnetically or electrically responsive control element of the osmotic pump device in an environment, at step 1202, and remotely transmitting the electromagnetic control signal to the osmotic pump device with signal characteristics sufficient to activate the magnetically or electrically responsive control element in the osmotic pump device to control the concentration of an osmotic-pressure generating material in the osmotic pump device, at step 1204.

Figure 25:
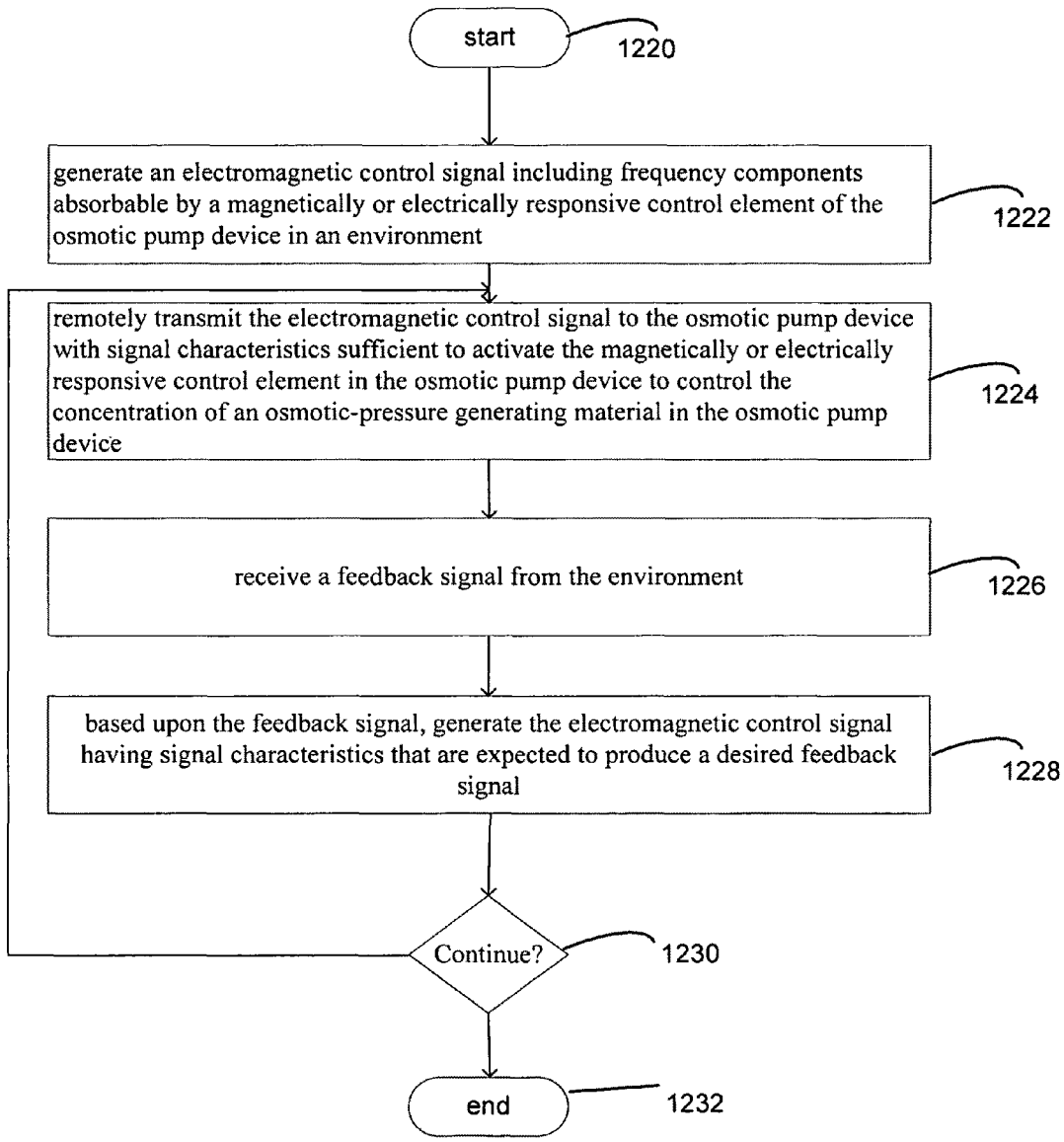
FIG. 25 is a flow diagram of an embodiment of a method of controlling an osmotic pump device.

The method as depicted generally in FIG. 24 may include generating and transmitting the electromagnetic control signal to the osmotic pump device with a remote control signal source. Generating an electromagnetic control signal may include generating the electromagnetic control signal from a model-based calculation or generating the electromagnetic control signal based on a stored pattern. As shown in FIG. 25, in addition to steps of generating an electromagnetic control signal including frequency components absorbable by a magnetically or electrically responsive control element of the osmotic pump device in an environment, at 1222, and remotely transmitting the electromagnetic control signal to the osmotic pump device with signal characteristics sufficient to activate the magnetically or electrically responsive control element in the osmotic pump device to control the concentration of an osmotic-pressure generating material in the osmotic pump device, at 1224. The method may also include receiving a feedback signal from the environment at step 1226 and, based upon the feedback signal, generating the electromagnetic control signal with signal characteristics expected to produce a desired feedback signal at step 1228. The method steps may be repeated until a decision to quit is made a decision point 1230. Receiving a feedback signal from the environment may include receiving a measure of osmolality, pH, temperature, pressure or concentration or chemical activity of a chemical within at least a portion of the environment.

Figure 26:
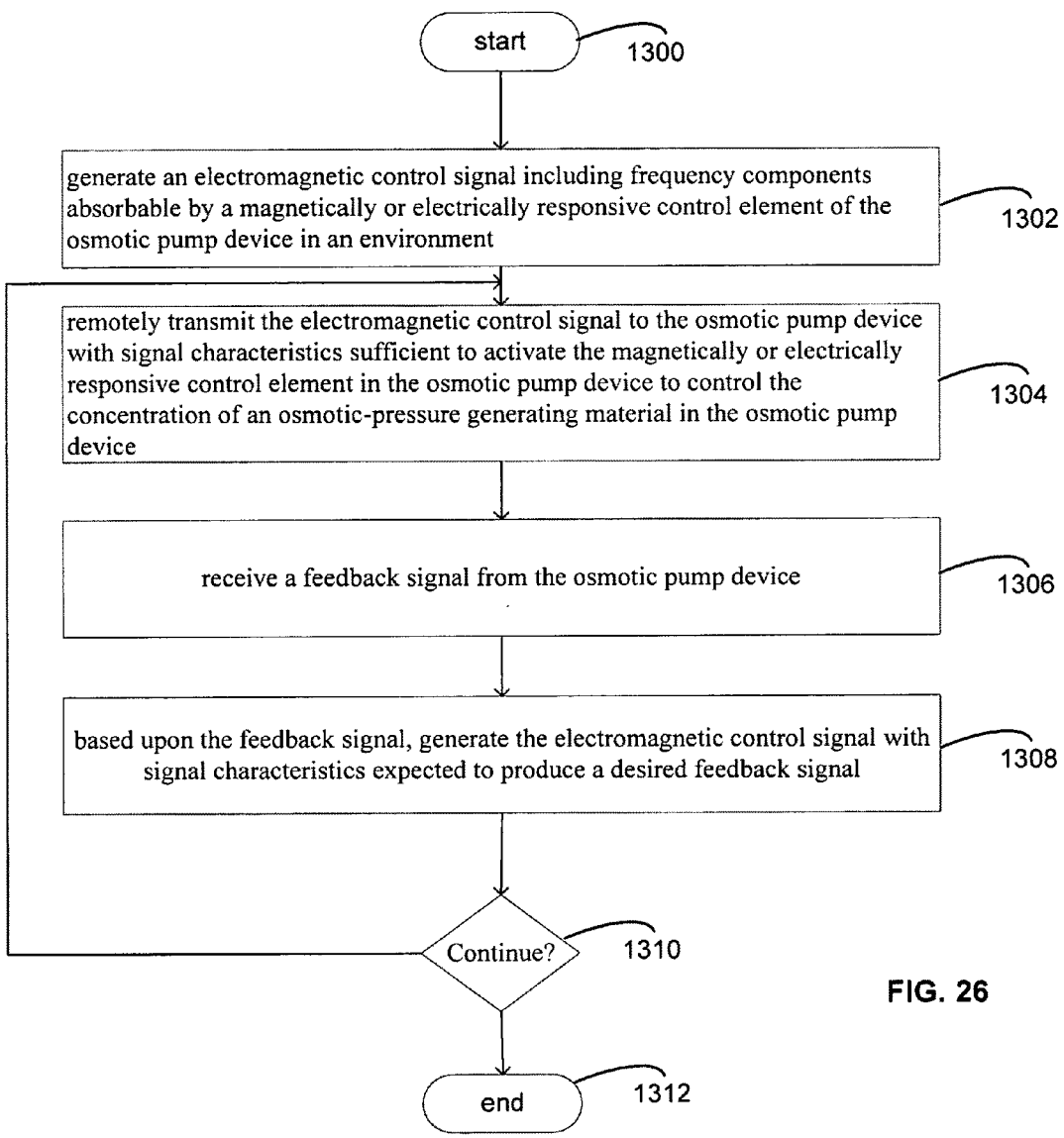
FIG. 26 is a flow diagram of an embodiment of a method of controlling an osmotic pump device.

As shown in FIG. 26, the method may include generating an electromagnetic control signal including frequency components absorbable by a magnetically or electrically responsive control element of the osmotic pump device in an environment, at step 1302, remotely transmitting the electromagnetic control signal to the osmotic pump device with signal characteristics sufficient to activate the magnetically or electrically responsive control element in the osmotic pump device to control the concentration of an osmotic-pressure generating material in the osmotic pump device, at 1304, receiving a feedback signal from the osmotic pump device at step 1306, and based upon the feedback signal, generating an electromagnetic control signal having signal characteristics that are expected to produce a desired feedback signal at step 1308. As noted in connection with other related embodiments, the method steps may be repeated until a decision to quit is made a decision point 1310. Receiving a feedback signal from the osmotic pump device may include receiving a signal representing a concentration of osmotic pressure-generating material within the osmotic pump device, the concentration or chemical activity of a chemical within or around the osmotic pump device, or the osmolality, pH, temperature, or pressure within or around the osmotic pump device.

Figure 27:
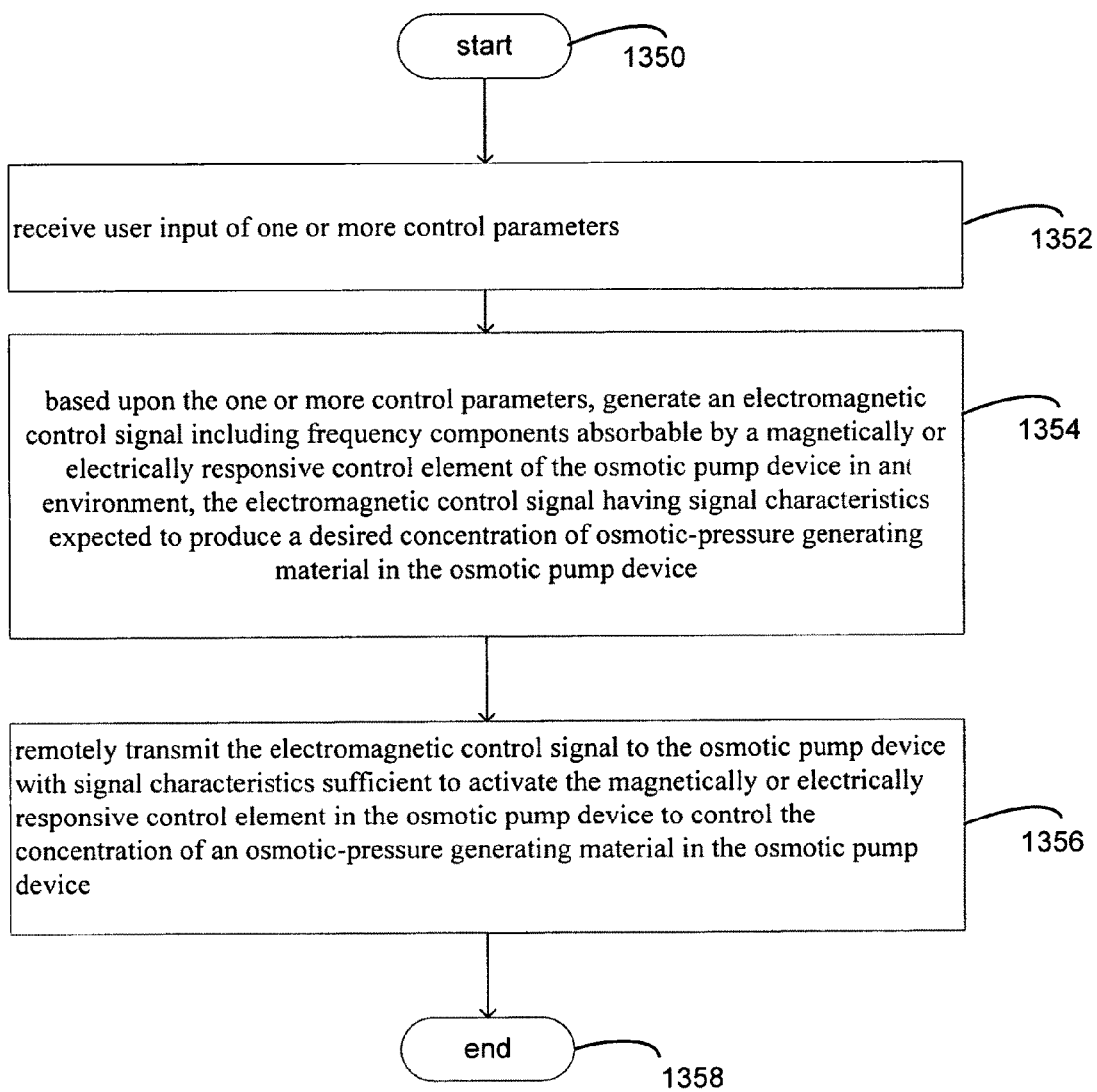
FIG. 27 is a flow diagram of an embodiment of a method of controlling an osmotic pump device.

In some embodiments, as shown in FIG. 27, the method may include receiving user input of one or more control parameters at step 1352, and based upon the one or more control parameters, generating an electromagnetic control signal including frequency components absorbable by a magnetically or electrically responsive control element of the osmotic pump device in an environment, the electromagnetic control signal having signal characteristics expected to produce a desired concentration of osmotic-pressure generating material in the osmotic pump device, at step 1354. The method also may include step 1356, including remotely transmitting the electromagnetic control signal to the osmotic pump device with signal characteristics sufficient to activated the magnetically or electrically responsive control element in the osmotic pump device to control the concentration of an osmotic pressure-generating material in the osmotic pump device. The desired concentration of osmotic pressure generating material in the osmotic pump device may be a concentration sufficient to produce a desired pumping rate by the osmotic pump device. The method may include activating the magnetically or electrically responsive control element to produce heating or cooling, or to produce a change in configuration of the magnetically or electrically responsive control element.

In some embodiments, the steps of generating an electromagnetic control signal and remotely transmitting the electromagnetic control signal to the osmotic pump device may be performed according to instructions provided in the form of software, hardware or firmware. Generating the electromagnetic control signal may include generating a static or quasi-static magnetic field, static or quasi-static electrical field, or radio-frequency, microwave, infrared, optical, or ultraviolet wavelength electromagnetic signal. The method may include generating the electromagnetic control signal under software control. The method may include modifying the concentration of the osmotic pressure-generating material within an osmotic chamber of the osmotic pump device by modifying the area of an interaction region within the osmotic chamber. Modifying the area of the interaction region may include increasing the area of the interaction region, which may include one or both of increasing the distances between interaction sites in the interaction region and increasing the number of available interaction sites in the reaction area. Conversely, modifying the area of the interaction region may include decreasing the area of the interaction region, which may include decreasing the distances between interaction sites in the interaction region and/or decreasing the number of available interaction sites in the reaction area.

Modifying the concentration of the osmotic pressure-generating material within an osmotic chamber of the osmotic pump device may include modifying a condition at an interaction region within the osmotic chamber, which may include, for example, heating or cooling at least a portion of the interaction region. Alternatively, or in addition, modifying a condition at the interaction region may include modifying the osmolality or the pH of at least a portion of the interaction region, or modifying the surface charge or surface energy of at least a portion of the interaction region. Modifying a condition at the interaction region may include modifying a condition within the osmotic chamber, such as modifying the volume of the osmotic chamber, heating or cooling at least a portion of the osmotic chamber, or modifying the osmolality or the pH within at least a portion of the osmotic chamber.

Figure 28:
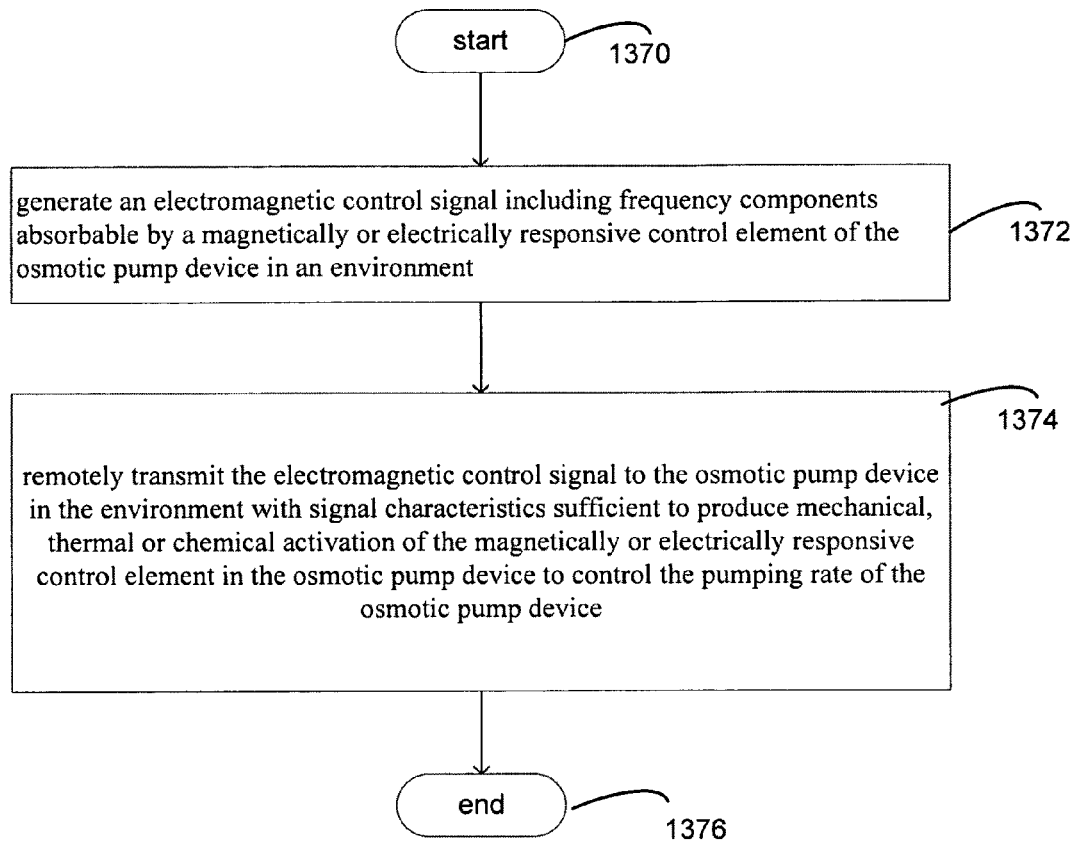
FIG. 28 is a flow diagram of an embodiment of a method of controlling an osmotic pump device.

A further method of controlling an osmotic pump device is depicted in FIG. 28, which includes generating an electromagnetic control signal including frequency components absorbable by a magnetically or electrically responsive control element of the osmotic pump device in an environment at step 1372, and remotely transmitting the electromagnetic control signal to the osmotic pump device in the environment with signal characteristics sufficient to produce mechanical, thermal or chemical activation of the magnetically or electrically responsive control element in the osmotic pump device to control the pumping rate of the osmotic pump device at step 1374. The method may include generating and transmitting the electromagnetic control signal with a remote control signal source. As in other described embodiments, the method may include generating the electromagnetic control signal from a model-based calculation or from a stored pattern. The method may also include receiving a feedback signal from the environment, and based at least in part upon the feedback signal, generating an electromagnetic control signal having signal characteristics expected to produce a desired feedback signal. Receiving a feedback signal from the environment may include receiving a measure of osmolality, pH, temperature, pressure, or concentration or chemical activity of a chemical within at least a portion of the environment.

Alternatively, or in addition, the method may include receiving a feedback signal from the osmotic pump device; and based at least in part upon the feedback signal, generating an electromagnetic control signal having signal characteristics expected to produce a desired feedback signal. Receiving a feedback signal from the osmotic pump device may include receiving a signal representing a concentration or a chemical activity of a material at an interaction region within an osmotic chamber of the osmotic pump device. The signal may represent the concentration or chemical activity of an osmotic pressure-generating material, for example. The method may include receiving user input of one or more control parameters, and based at least in part upon the one or more control parameters, generating an electromagnetic control signal having signal characteristics expected to produce a desired pumping rate of the osmotic pump device. The method may include activating the magnetically or electrically responsive control element to produce heating or cooling, wherein the heating or cooling modifies an interaction at an interaction region of the osmotic pump device and wherein the interaction modifies the osmotic pressure in the osmotic pump device, or activating the magnetically or electrically responsive control element to produce a change in configuration of the magnetically or electrically responsive control element, wherein the change in configuration modifies an interaction at an interaction region of the osmotic pump device and wherein the interaction modifies the osmotic pressure in the osmotic pump device. Such a change in configuration may include expansion or contraction of the magnetically or electrically responsive control element. Expansion may cause exposure of interaction sites at the interaction region, or change the density of interaction sites at the interaction region. In cases where the magnetically or electrically responsive control element includes a polymer, the expansion of the magnetically or electrically responsive control element may cause opening of pores in the polymer. A change in configuration may include a change in shape of a magnetically or electrically responsive control element.

In some embodiments, the steps of generating an electromagnetic control signal and of remotely transmitting the electromagnetic control signal to the osmotic pump device may be performed according to instructions provided in the form of software, hardware or firmware. Software for controlling an osmotic pump device may include, for example, instructions for generating an electromagnetic control signal including frequency components absorbable by a magnetically or electrically responsive control element of the osmotic pump device in an environment, and instructions for remotely transmitting the electromagnetic control signal to the osmotic pump device in the environment with signal characteristics sufficient to produce at least one of mechanical, thermal or chemical activation of the magnetically or electrically responsive control element in the osmotic pump device to control the pumping rate of osmotic pump device. The instructions for generating the electromagnetic control signal may include instructions for calculating the electromagnetic control signal based on a model, and/or for generating the electromagnetic control signal based on a pattern stored in a data storage location.

The software may also include instructions for receiving a feedback signal from the environment and instructions for generating the electromagnetic control signal based at least in part upon the received feedback signal, the electromagnetic control signal having signal characteristics expected to produce a desired feedback signal. In some software embodiments, the software may also include instructions for receiving a feedback signal from the osmotic pump device and for generating the electromagnetic control signal based at least in part on the received feedback signal, the electromagnetic control signal having frequency composition and amplitude expected to produce a desired feedback signal. The software may include instructions for receiving user input of one or more control parameters and instructions for generating the electromagnetic control signal based at least in part upon the one or more control parameters.

The remote controller may produce an electromagnetic signal having one or both of a defined magnetic field strength or defined electric field strength. In general, the term field strength, as applied to either magnetic or electric fields, may refer to field amplitude, squared-amplitude, or time-averaged squared-amplitude. The electromagnetic signal may have signal characteristics sufficient to produce a change in dimension of the remotely activatable control element, a change in temperature of the remotely activatable control element, a change in conformation of the remotely activatable control element, or a change in orientation or position of the remotely activatable control element. In some embodiments, the electromagnetic signal generator may include an electromagnet or electrically-polarizable element, or at least one permanent magnet or electret. The electromagnetic signal may be produced at least in part according to a pre-programmed pattern. The electromagnetic signal may have signal characteristics sufficient to produce a change in dimension in the remotely activatable control element, the change in dimension causing a change in the concentration of the osmotic pressure-generating material within the osmotic chamber of the osmotic pump device. It may have signal characteristics sufficient to produce a change in temperature of the remotely activatable control element, the change in temperature causing a change in the concentration of the osmotic pressure-generating material within the osmotic chamber of the osmotic pump device. In some embodiments, it may have signal characteristics sufficient to produce a change in one or more of shape, volume, surface area or configuration of the remotely activatable control element, the change in dimension in one or more of shape, volume, surface area or configuration of the remotely activatable control element causing a change in the concentration of the osmotic pressure-generating material within the osmotic chamber of the osmotic pump device. The electromagnetic signal may have signal characteristics sufficient to produce a change in shape in a remotely activatable control element including a shape memory material, a bimetallic structure, or a polymeric material. The electromagnetic signal may have a defined magnetic field strength or spatial orientation, or a defined electric field strength or spatial orientation.

Figure 29:
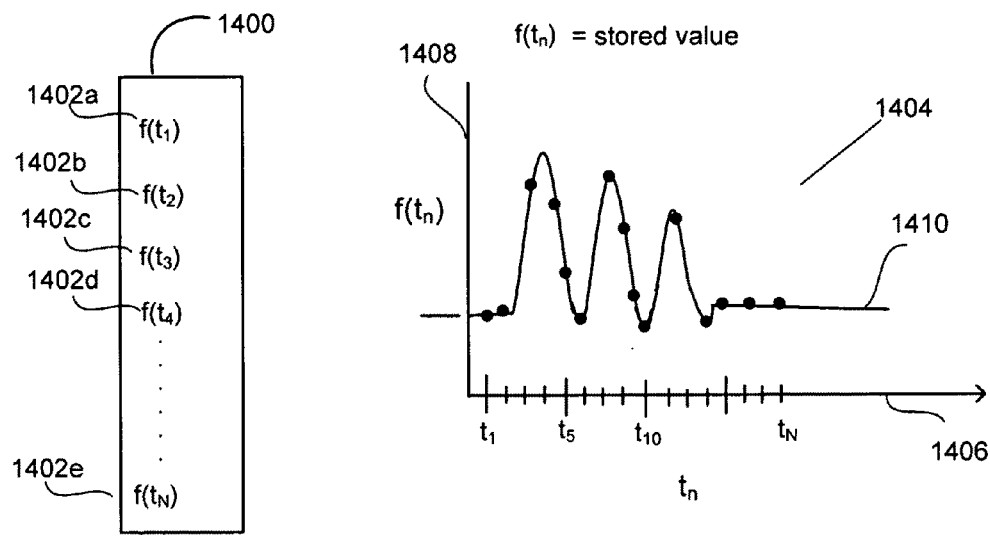
FIG. 29 illustrates a control signal generated from stored pattern data.

The electromagnetic control signal may be produced based at least in part upon a predetermined activation pattern. As shown in FIG. 29, a predetermined activation pattern may include a set of stored data 1402a, 1402b, 1402c, 1402d, ... 1402e, having values $f(t_1), f(t_2), f(t_3), f(t_4), \ldots f(t_N)$, stored in a memory location 1400. The activation pattern upon which the electromagnetic signal is based is depicted in plot 1404 in FIG. 29. In plot 1404, time $t_n$ is indicated on axis 1406 and signal amplitude $f(t_n)$, which is a function of $t_n$, is indicated on axis 1408. The value of the electromagnetic signal over time is represented by trace 1410. The predetermined activation pattern represented by data 1402a, 1402b, 1402c, 1402d, ... 1402e may be based upon calculation, measurements, or any other method that may be used for producing an activation pattern suitable for activating a remotely activatable control element. Memory 1400 may be a memory location in a remote controller. As an example, a simple remote controller may include a stored activation pattern in memory and include electrical circuitry configured to generate an electromagnetic control signal according to the pattern for a preset duration or at preset intervals, without further input of either feedback information or user data. In a more complex embodiment, a predetermined activation pattern may be generated in response to certain feedback or user input conditions.

Figure 30:
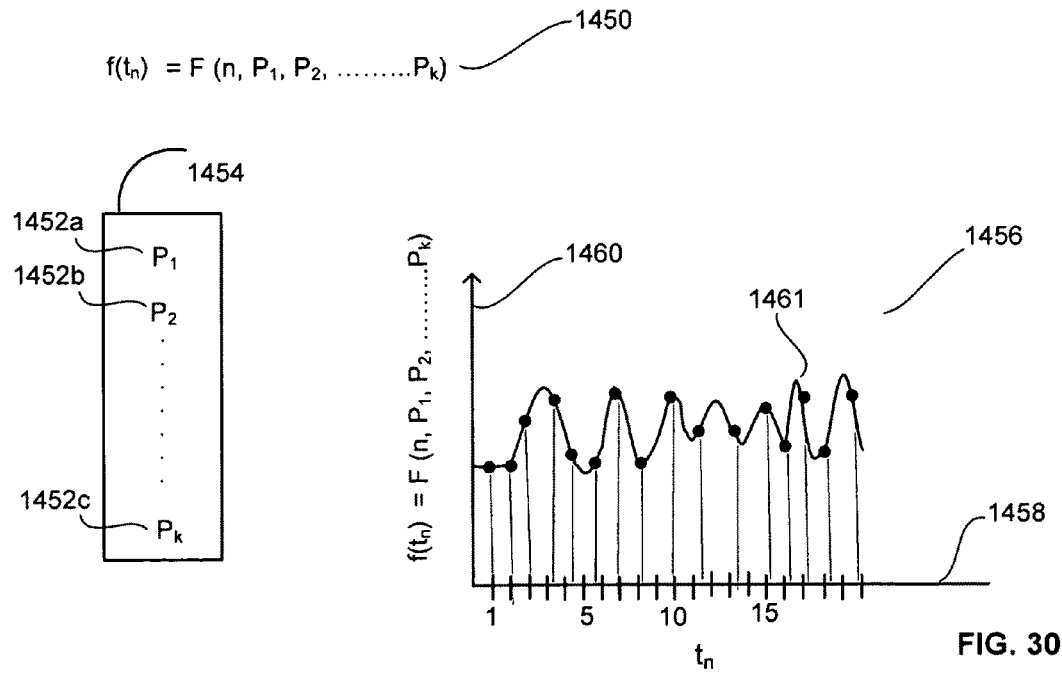
FIG. 30 illustrates a control signal calculated from a model based on stored parameters.

An electromagnetic signal may also be produced based upon a model-based calculation. As shown in FIG. 30, an activation pattern $f(t_n)$ may be a function not only of time $(t_n)$ but also of model parameters $P_1, P_2, \ldots P_k$, as indicated by equation 1450. Data 1452a, 1452b, ... 1452c having values $P_1, P_2, \ldots P_k$ may be stored in memory 1454. An electromagnetic control signal may be computed from the stored model parameters and time information. For example, as indicated in plot 1456, time is indicated on axis 1458 and the strength or amplitude of the electromagnetic control signal is indicated on axis 1460, so that trace 1461 represents $f(t_n)$. Memory 1454 may be a memory location in a remote controller. The remote controller may generate an electromagnetic control signal based upon the stored function and corresponding parameters. In some embodiments, the electromagnetic control signal may also be a function of one or more feedback signals (from the osmotic pump device or the environment, for example) or of some user input of data or instructions.

Figure 31:
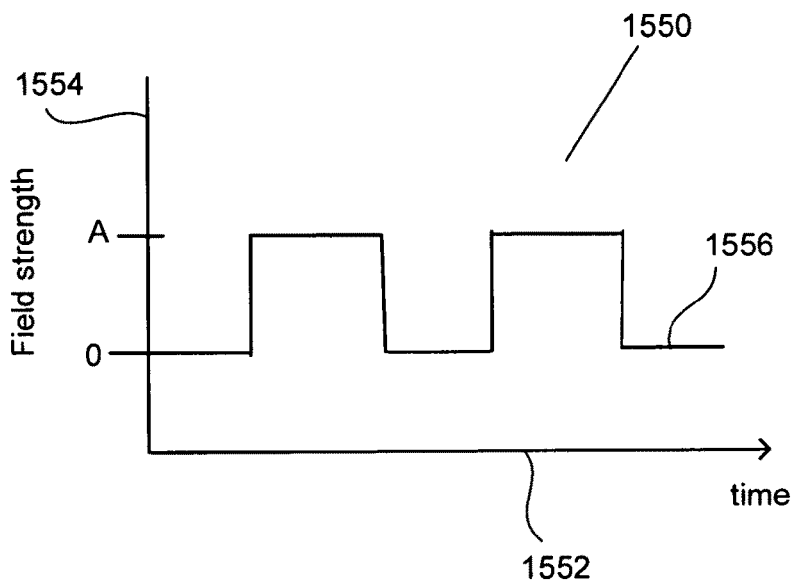
FIG. 31 depicts an exemplary control signal.

FIG. 31 depicts an example of an electromagnetic waveform. In plot 1550, time is plotted on axis 1552, and electromagnetic field strength is plotted on axis 1554. Trace 1556 has the form of a square wave, switching between zero amplitude and a non-zero amplitude, A.

Figure 32:
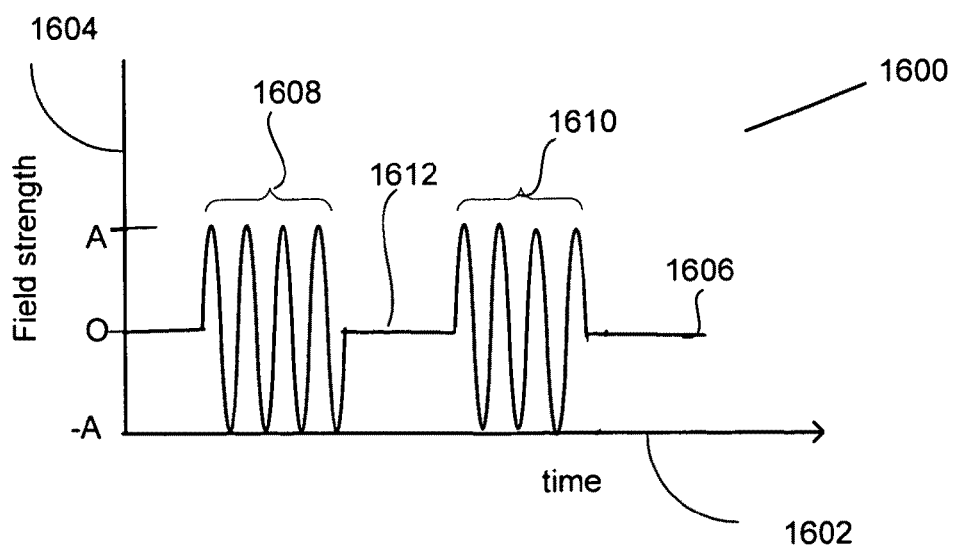
FIG. 32 depicts another exemplary control signal.

FIG. 32 depicts another example of an electromagnetic waveform. In plot 1600, time is plotted on axis 1602, and electromagnetic field strength is plotted on axis 1604. Trace 1606 includes bursts 1608 and 1610, during which the field strength varies between A and −A, at a selected frequency, and interval 1612, during which field strength is zero.

Figure 33:
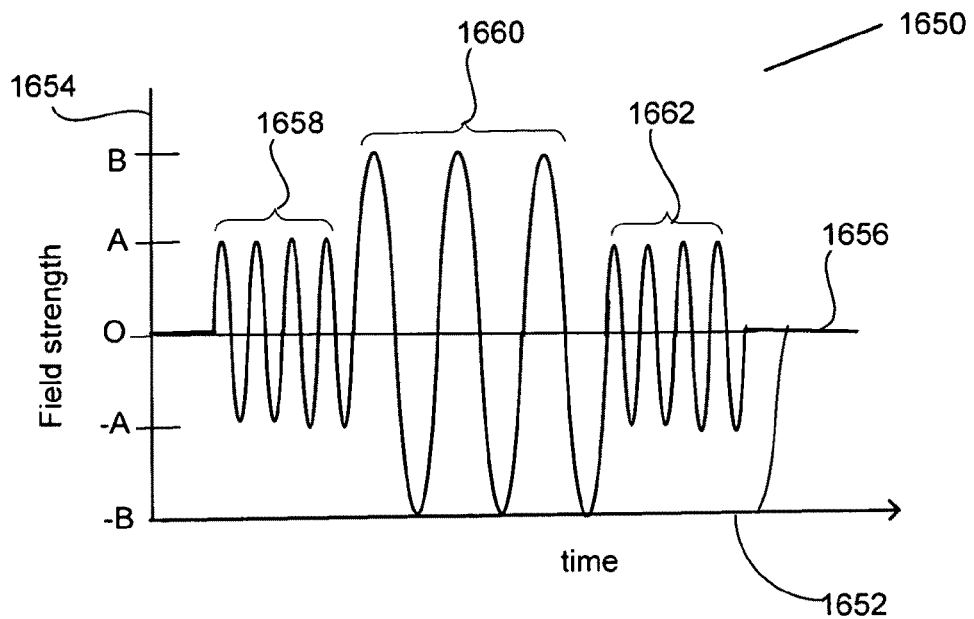
FIG. 33 depicts another exemplary control signal.

FIG. 33 depicts another example of an electromagnetic waveform. In plot 1650, time is plotted on axis 1652, and electromagnetic field strength is plotted on axis 1654. Trace 1656 includes bursts 1658, and 1662, during which the field strength varies between A and −A at a first frequency, and burst 1660, during which the field strength varies between B and −B at a second (lower) frequency. Different frequencies may be selectively received by certain individuals or classes of remotely activatable control elements within a device or system including multiple remotely activatable control elements. An electromagnetic control signal may be characterized by one or more frequencies, phases, amplitudes, or polarizations. An electromagnetic control signal may have a characteristic temporal profile and direction, and characteristic spatial dependencies.

The magnetic or electric field control signal produced by the remote controller may have one or both of a defined magnetic field strength or a defined electric field strength. At low frequencies the electrical and magnetic components of an electromagnetic field are separable when the field enters a medium. Therefore, in static and quasi-static field application, the electromagnetic field control signal may be considered as an electrical field or a magnetic field. A quasi-static field is one that varies slowly, i.e., with a wavelength that is long with respect to the physical scale of interest or a frequency that is low compared to the characteristic response frequency of the object or medium; therefore, the frequency beyond which a field will no longer be considered 'quasi-static' is dependent upon the dimensions or electrodynamic properties of the medium or structure(s) influenced by the field.

Figure 34:
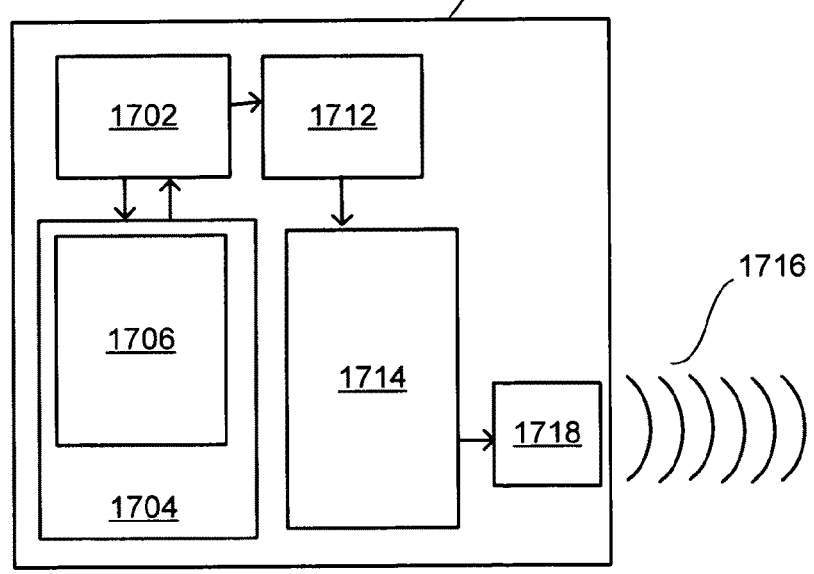
FIG. 34 illustrates an embodiment of a remote control device including software for controlling control signal generation and transmission.

FIG. 34 depicts a remote controller 1700 having a memory 1704 capable of storing pre-determined data values or parameters used in model-based calculation, as described in connection with FIGS. 29 and 30. Remote controller 1700 may also include electrical circuitry 1702, signal generator 1712, and signal transmitter 1714 for transmitting electromagnetic control signal 1716, generally as described previously. Memory 1704 may include memory location 1706 for containing a stored activation pattern or model parameters; portions of memory 1704 may also be used for storing operating system, program code, etc. for use by processor 1702. The controller 1700 may also include a beam director 1718, such as an antenna, optical element, mirror, transducer, or other structure that may impact control of electromagnetic signaling.

The remote controller may include an electromagnetic signal generator capable of producing various types of control signals. The remote controller may include an electromagnetic signal generator configured to generate a static or quasi-static electrical field control signal or a static or quasi-static magnetic field control signal sufficient to activate the remotely activatable control element to control the concentration of the osmotic pressure-generating material within the osmotic chamber in a desired manner. Alternatively, the remote controller may include an electromagnetic signal generator configured to generate a radio-frequency, microwave, infrared, millimeter wave, optical, or ultraviolet electromagnetic signal sufficient to activate the remotely activatable control element to control the concentration of the osmotic pressure-generating material within the osmotic chamber in a desired manner.

Figure 35:
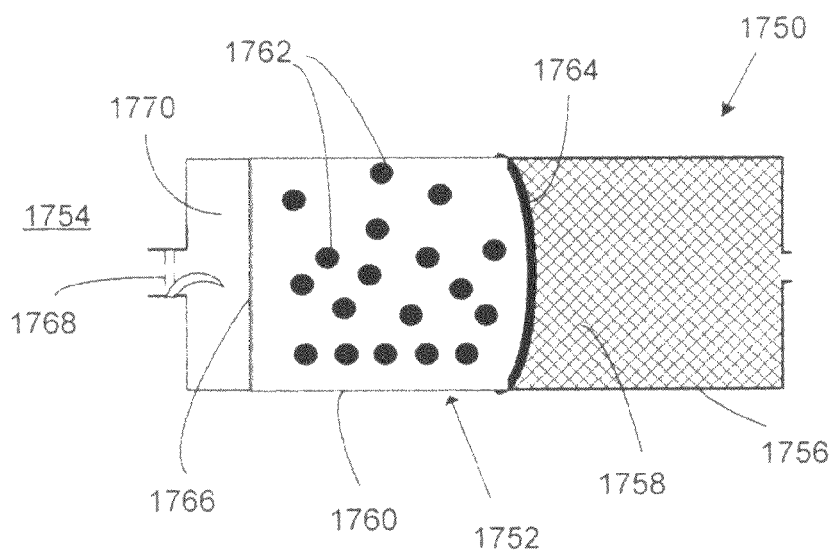
FIG. 35 is a cross-sectional view of an osmotic pump device having a valve at an inlet.
Figure 36:
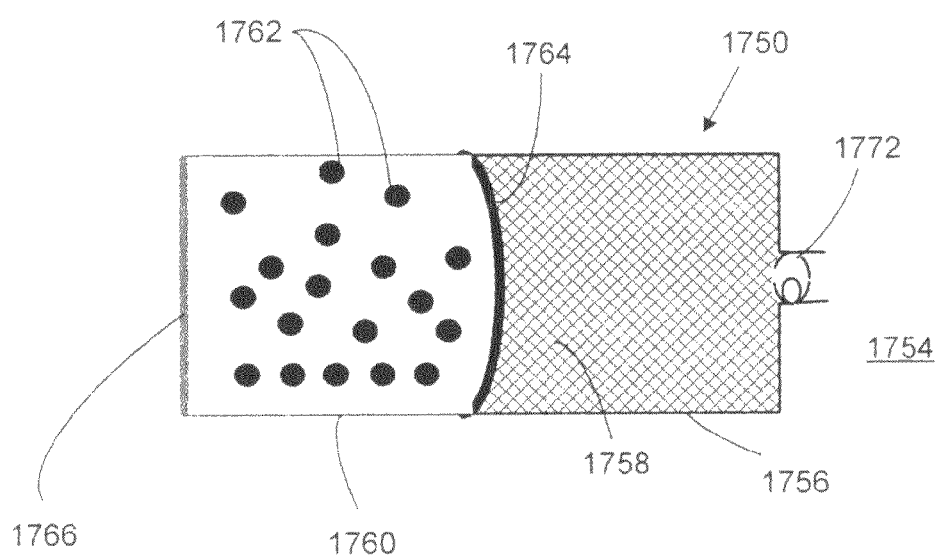
FIG. 36 is a cross-sectional view of an osmotic pump device having a valve at an outlet.

In a further embodiment as exemplified in FIG. 35, an osmotic pump device 1750 may include a housing 1752 configured for placement in an environment 1754; a delivery reservoir 1756 capable of containing a delivery fluid 1758; an osmotic chamber 1760; an osmotic pressure-generating material 1762 contained within the osmotic chamber 1760; a pressure-responsive movable barrier 1764 separating the osmotic chamber 1760 from the delivery reservoir 1756, the pressure-responsive barrier 1764 being substantially impermeable to the osmotic pressure-generating material 1762 and configured to move in response to a change in pressure in the osmotic chamber 1760 to produce a change in at least one of pressure or volume of the delivery reservoir 1756; a semi-permeable membrane 1766 separating the osmotic chamber 1760 from an osmotic fluid source (in this example, environment 1754), the semi-permeable membrane being substantially permeable by fluid from the osmotic fluid source but substantially impermeable to the osmotic pressure-generating material 1762; and at least one remotely controllable valve 1768 configured to regulate the pumping of the material from the delivery reservoir in an on-going fashion responsive to a time-varying electromagnetic field control signal. As depicted in FIG. 35, the remotely controllable valve 1768 may be located between the osmotic fluid source (environment 1754, via antechamber 1770) and the osmotic chamber 1760 to regulate the flow of osmotic fluid into the osmotic chamber 1760. Alternatively, as depicted in FIG. 36, a remotely controllable valve 1772 may be located downstream of the delivery reservoir 1756 to regulate the flow of delivery fluid 1758 out of the delivery reservoir. The delivery reservoir may include an outlet through which the delivery fluid moves into the environment in response to the change in at least one of pressure or volume in the delivery reservoir.

The remotely controllable valve (e.g. 1728 or 1772 in FIGS. 35 and 36, respectively) may include an electromagnetically responsive control element, which may, for example, include at least one of a permanently magnetizable material, a ferromagnetic material, a ferrimagnetic material, a ferrous material, a ferric material, a dielectric or ferroelectric or piezoelectric material, a diamagnetic material, a paramagnetic material, and an antiferromagnetic material. The electromagnetically responsive control element may include a shape memory material, for example, a shape memory polymer or a shape memory metal. In some embodiments, the electromagnetically responsive control element may include a bimetallic structure, polymer, ceramic, dielectric or metal, a hydrogel, a ferrogel or a ferroelectric. In some embodiments, the electromagnetically responsive control element may be a composite structure, and may include, for example, a polymer and a magnetically or electrically active component. In some embodiments, the electromagnetically responsive control element may include an expanding element.

The osmotic pump device may include a valve responsive to a change in at least one dimension of the remotely activatable control element. The valve may be formed in its entirety by the remotely activatable control element, or the remotely activatable control element may form only a part of the valve or the valve actuation mechanism. The remotely activatable control element may respond to the control signal by changing in at least one dimension, and may include various materials, for example polymer, ceramic, dielectric or metal. For example, the remotely activatable control element may include a shape memory material such as a shape memory polymer, a memory foam, or a shape memory alloy such as nitinol (an alloy of titanium and nickel) or ferromagnetic shape memory materials (e.g., a $Ni_2MnGa$ alloy). The remotely activatable control element may include a bimetallic structure.

In the embodiment of an osmotic pump device depicted in FIG. 35, a remotely activatable valve/control element 1768 is formed from a shape memory material. The open position of the valve formed by remotely activatable control element 1768 is indicated by a solid line, while the closed position is indicated by a dashed line.

In the embodiment of FIG. 36, valve 1772 is a remotely activatable control element that may include an expandable gel structure, such as hydrogel or a ferrogel. The remotely activatable control element forms valve 1772 for controlling the flow of fluid into the osmotic pump device 1764, shown in its open (contracted) form by a solid line and shown in its closed (expanded) form by a dashed line. The osmotic pressure generated may be modified by adjusting the valve 1772 to control the flow of fluid out of the osmotic pump device. An example of a magnetically controlled hydrogel valve is described in "A temperature controlled micro valve for biomedical applications using a temperature sensitive hydrogel" Micro Total Analysis Systems Symposium, Nov. 3-7, Nara, Japan, 1: 142-144H. J. van der Linden, D. J. Beebe, and P. Bergveld (2002), incorporated herein by reference. Other potential materials and structures for valves may be as described in U.S. Pat. Nos. 6,682,521, 6,755,621, 6,720,402, 6,607,553, which are incorporated herein by reference.

Figure 37:
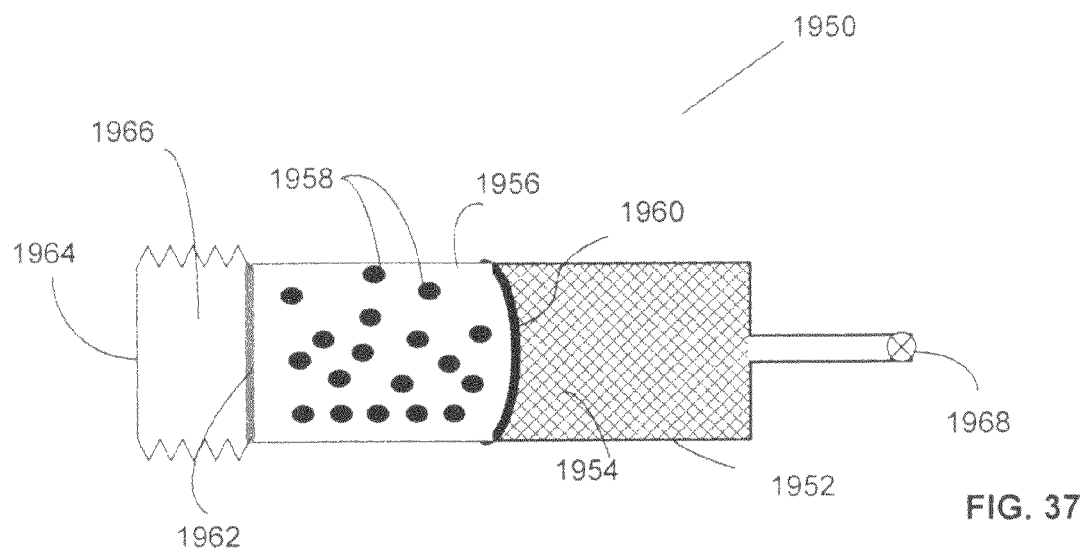
FIG. 37 illustrates an embodiment of an osmotic pump device.

In some embodiments, the osmotic fluid source may be the environment, while in other embodiments the osmotic fluid source may be a reservoir on the osmotic pump device. FIG. 37 depicts osmotic pump device 1950, including delivery reservoir 1952 containing delivery fluid 1954, osmotic chamber 1956 containing osmotic pressure-generating material 1958, pressure-responsive movable barrier 1960, and semi-permeable barrier 1962, all of which function as described previously. Osmotic pump device 1950 also includes collapsible reservoir 1964 containing osmotic fluid 1966. Collapsible reservoir 1964 is designed to collapse as osmotic fluid 1966 is drawn through semi-permeable barrier 1962. Flow of fluid out of delivery reservoir 1952 may be regulated by remotely activatable valve 1968.

Figure 38:
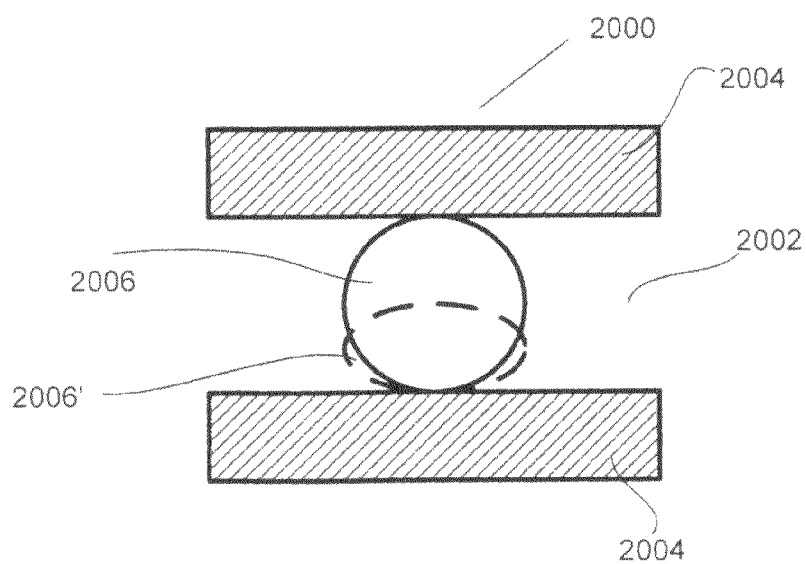
FIG. 38 is a cross-sectional view of an embodiment of a valve including a remotely activatable valve element.

FIG. 38 is a cross-sectional view of an embodiment of a valve 2000 in channel 2002 defined by walls 2004 and including a remotely activatable valve element 2006 positioned in a channel 2002. Valve element 2006 may be a magnetically or electrically responsive element formed from, for example, a ferropolymer or other material responsive to applied magnetic or electric or electromagnetic fields or radiation. Valve element may have a first form 2006, indicated by the solid outline, when exposed to a first magnetic or electric field strength, and a second form 2006', indicated by the dashed outline, when exposed to a second magnetic or electric field strength. Valves of this type are disclosed, for example, in "A temperature controlled micro valve for biomedical applications using a temperature sensitive hydrogel" Micro Total Analysis Systems Symposium, Nov. 3-7, Nara, Japan, 1: 142-144, H. J. van der Linden, D. J. Beebe, and P. Bergveld (2002), incorporated herein by reference. See also U.S. Pat. Nos. 5,643,246, 5,830,207, and 6,755,621, which are also incorporated herein by reference. In first form 2006, valve element 2006 obstructs channel 2002, blocking the flow of fluid through valve 2000. In its second form 2006', valve element 2006 does not obstruct channel 2002, and fluid flow through valve 2000 is unimpeded.

Figure 39:
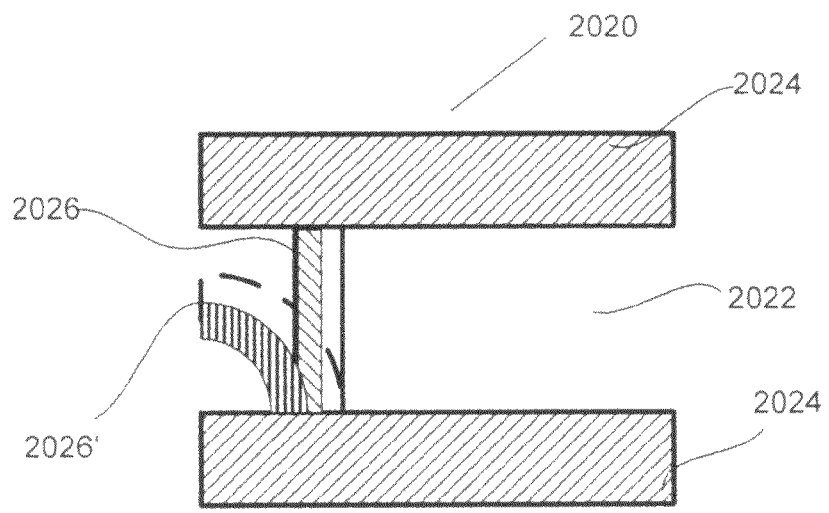
FIG. 39 is a cross-sectional view of an embodiment of a valve including a remotely activatable valve element.

FIG. 39 is a cross-sectional view of an embodiment of another type of valve 2020, in which fluid channel 2022 defined by walls 2024 includes a remotely activatable valve element 2026. Remotely activatable valve element 2026 is formed, for example from a bimetallic strip that changes from a first configuration to a second configuration during heating produced by exposure to a magnetic or electric or electromagnetic field or radiation control signal. An open configuration of remotely activatable valve element 2026 is indicated by reference number 2026'.

In some valve embodiments, opening or closing of the valve may be produced by a transient application of a magnetic or electric or electromagnetic control signal, the control signal serving to cause switching of the valve element from a first configuration to a second configuration, while in other continuous application of a control signal may be required to maintain the valve element in one of the two configurations, with the valve element returning to the other configuration upon removal of the control signal. Such a valve elements may be formed from a shape memory metal, a shape memory polymer, or a bimetallic strip formed from laminated layer of metals having different coefficients of thermal expansion, for example. The construction of such valve elements is known to those of skill in the relevant arts, for example.

Figure 40:
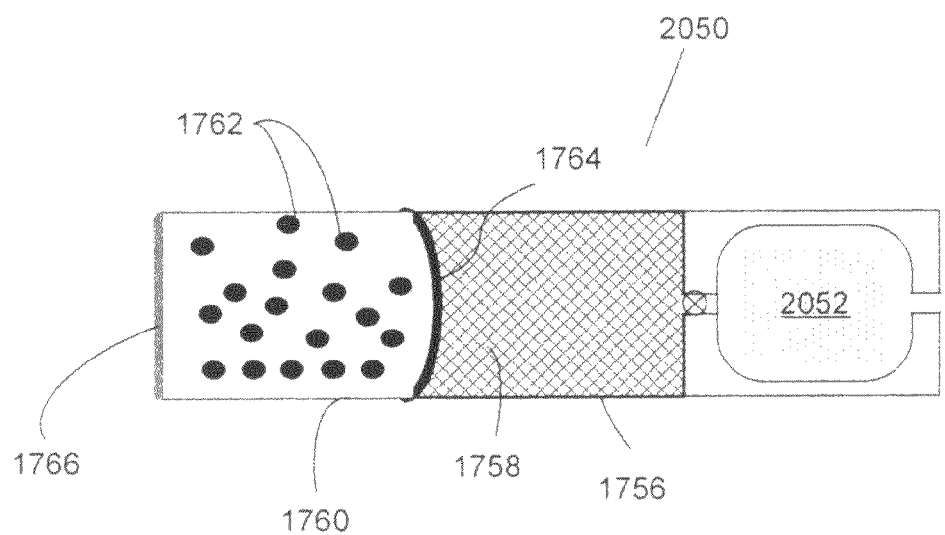
FIG. 40 depicts an embodiment of an osmotic pump device including a downstream fluid handling structure.

In some embodiments, as illustrated in FIG. 40, an osmotic pump system 2050 may include a downstream fluid handling structure 2052 in fluid communication with delivery reservoir 1756 and configured to receive delivery fluid 1758 ejected from the delivery reservoir 1756 in response to the change in at least one of pressure or volume in delivery reservoir 1756. The downstream fluid handling structure 2052 may include at least one of a channel or a chamber. The pressure-responsive movable barrier 1764 may include a flexible membrane, for example as depicted in FIG. 40, or a piston, for example, as depicted in FIGS. 5A and 5B. Osmotic pump system 2050 also includes osmotic pressure generating material 1762, osmotic chamber 1760, and semi-permeable membrane 1766, e.g., as described in connection with FIGS. 35 and 36. The osmotic pressure-generating material may include ionic and non-ionic water-attracting or water absorbing materials, non-volatile water-soluble species, salts, sugars, polysaccharides, polymers, hydrogels, osmopolymers, hydrophilic polymers, and absorbent polymers, examples of which are disclose herein.

Figure 41:
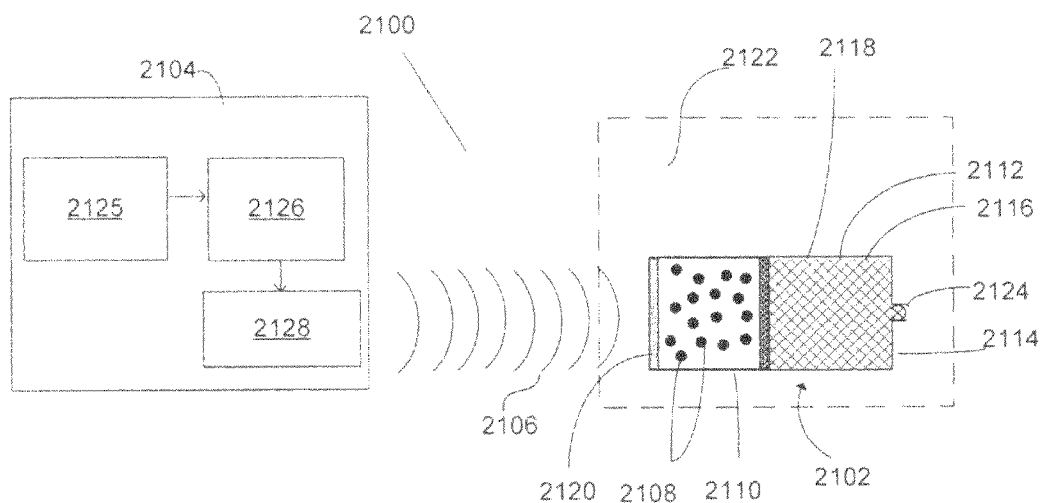
FIG. 41 is a schematic diagram of an osmotic pump system including a remote controller.

An osmotic pump device of the type depicted in FIGS. 35-37 or 40 may form a part of an osmotic pump system 2100 as shown in FIG. 41 that includes an osmotic pump device 2102 and a remote control signal source 2104 capable of generating a time-varying electromagnetic field control signal 2106 sufficient to modify the concentration of osmotic pressure-generating material 2108 within the osmotic chamber 2110 of the osmotic pump 2102. As described previously, the osmotic pump device may include a housing 2112 configured for placement in an environment, a delivery reservoir 2114 capable of containing a delivery fluid, an osmotic chamber 2110, an osmotic pressure-generating material 2108 contained within the osmotic chamber 2110, a pressure-responsive movable barrier 2118 separating the osmotic chamber from the delivery reservoir 2114, the pressure-responsive barrier being substantially impermeable to the osmotic pressure-generating material 2108 and configured to move in response to a change in pressure in the osmotic chamber 2110 to produce a change in at least one of pressure or volume of the delivery reservoir, a semi-permeable membrane 2120 separating the osmotic chamber from an osmotic fluid source, the semi-permeable membrane 2120 being substantially permeable by fluid from the osmotic fluid source (e.g. environment 2122) but substantially impermeable to the osmotic pressure-generating material 2108, and at least one remotely controllable valve 2124 configured to regulate the pumping of the material from the delivery reservoir 2114 in an on-going fashion responsive to a time-varying electromagnetic field control signal. Remote control signal source 2104 may include electrical circuitry 2125, signal generator 2126, and signal transmitter 2128, which may function in the same fashion as the components of remote control signal source 754 in FIG. 17, for example. The environment 2122 may be selected, for example, from a body of an organism, a body of water, or a contained fluid volume The remote control signal source 2104 may include at least one of hardware, firmware, or software configured to control generation of the electromagnetic control field signal. The remotely controllable valve 2124 may include an electromagnetically responsive control element, which may include at least one of a permanently magnetizable material, a ferromagnetic material, a ferrimagnetic material, a ferrous material, a ferric material, a dielectric or ferroelectric or piezoelectric material, a diamagnetic material, a paramagnetic material, and an antiferromagnetic material. The electromagnetically responsive control element may include a shape memory material such as a shape memory polymer or a shape memory metal, or a bimetallic structure. The electromagnetically responsive control element includes a polymer, ceramic, dielectric or metal. The electromagnetically responsive control element may include at least one of a hydrogel, a ferrogel or a ferroelectric, or a combination of a polymer and a magnetically or electrically active component. An electromagnetically responsive control element includes an expanding element.

Remote control signal source 2104 may be configured to generate a static or quasi-static electrical field control signal sufficient to activate the remotely controllable valve to control the pumping of material from the delivery reservoir in a desired manner, or a static or quasi-static magnetic field control signal sufficient to activate the remotely controllable valve to control the pumping of material from the delivery reservoir in a desired manner. In some embodiments, the remote control signal source may be configured to generate a radio-frequency, microwave, infrared, millimeter wave, optical, or ultraviolet electromagnetic field control signal sufficient to activate the remotely controllable valve to control the pumping of material from the delivery reservoir in a desired manner.

A remote controller for an osmotic pump device may include an electromagnetic signal generator capable of producing a time-varying electromagnetic field control signal sufficient to adjust a remotely controllable valve in an osmotic pump device located in an environment to produce a desired time-varying pumping rate of delivery fluid from a delivery reservoir of the pump to the environment, the pumping rate depending on the flow rate of fluid through the valve, and an electromagnetic signal transmitter capable of transmitting the electromagnetic signal to an electromagnetically responsive control element of the remotely controllable valve.

The electromagnetic signal generator may include electrical circuitry and/or a microprocessor. The electromagnetic signal may be produced at least in part according to a pre-determined activation pattern, and the remote controller may include a memory capable of storing the pre-determined activation pattern. In addition, or as an alternative, the electromagnetic signal may be produced based on a model-based calculation, and the remote controller may include a memory capable of storing model parameters used in the model-based calculation. In some embodiments, the electromagnetic signal may be produced based at least in part upon a feedback signal sensed from the environment.

The electromagnetic signal may have a defined magnetic field strength or defined electric field strength. In some embodiments of the remote controller, the electromagnetic signal may have signal characteristics sufficient to produce a change in dimension in the electromagnetically responsive control element of the remotely controllable valve. For example, the electromagnetic signal may have signal characteristics sufficient to produce contraction in at least one dimension of the electromagnetically responsive control element, or expansion in at least one dimension of the electromagnetically responsive control element. In some embodiments, the electromagnetic signal may have signal characteristics sufficient to produce a change in temperature, shape, volume, surface area, or orientation in the electromagnetically responsive control element. The electromagnetic signal may have signal characteristics sufficient to produce a change in shape in an electromagnetically responsive control element comprising a shape memory material; the shape memory material may be a shape memory metal or a shape memory polymer. Alternatively, the electromagnetic signal has signal characteristics sufficient to produce a change in shape in an electromagnetically responsive control element including a bimetallic structure. The electromagnetic signal has signal characteristics sufficient to produce a change in shape in an electromagnetically responsive control element including a polymeric material.

Figure 42:
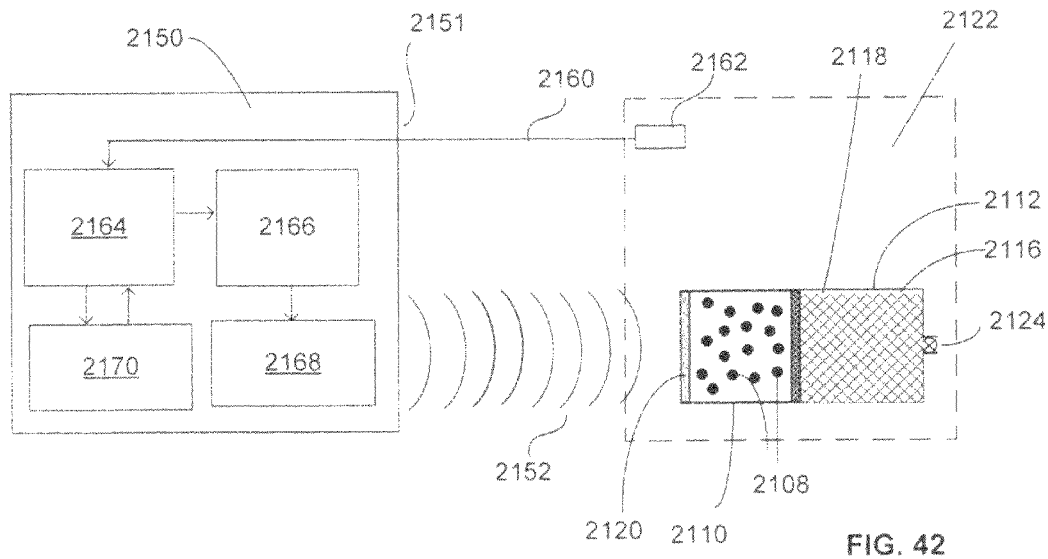
FIG. 42 depicts an embodiment of a system including a remote control device, an osmotic pump device, and a sensor.

As depicted in FIG. 42, in some embodiments of an osmotic pump system, a remote controller 2150 may include a signal input 2151 adapted for receiving a feedback signal 2160 from sensor 2162 in the environment 2122, wherein the electromagnetic signal 2152 is determined based at least in part upon the feedback signal 2160. The feedback signal 2160 may correspond to the concentration or chemical activity of a chemical in the environment, or the osmolality, pH, temperature, or pressure of the environment. Remote controller 2150 may include electrical circuitry 2164, signal generator 2166, signal transmitter 2168, and memory 2170, for example. Feedback from sensor 2162 may be sent over a wire connection or, in some embodiments, transmitted wirelessly.

Figure 43:
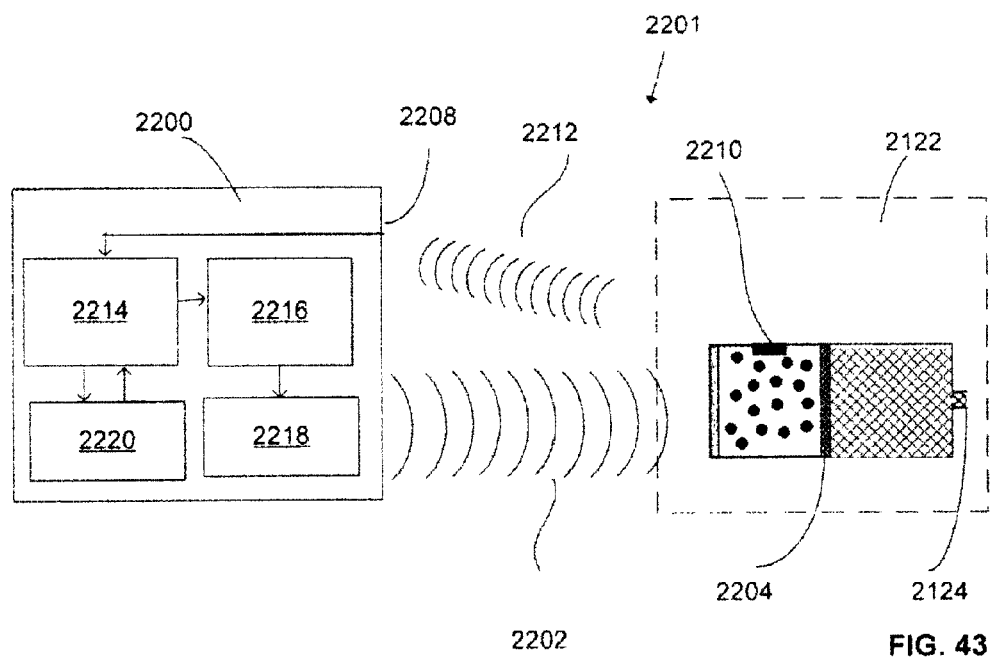
FIG. 43 depicts an embodiment of a system including a remote control device and an osmotic pump device including a sensor.

In some embodiments, as depicted in FIG. 43, a remote controller 2200 may include a signal input 2208 adapted for receiving a feedback signal 2212 from sensor 2210 in osmotic pump device 2204. Osmotic pump system 2201 in FIG. 43 include remote controller 2200, which transmits electromagnetic control signal 2202 to osmotic pump device 2204 in environment 2122. Feedback signal 2212 from the osmotic pump device may correspond to the osmolality or the pH within or around the osmotic pump device, the concentration or chemical activity of a chemical within or around the osmotic pump device, a temperature or pressure within or around the osmotic pump device, the pumping rate of the osmotic pump device, or some other parameter sensed from the osmotic pump device. The electromagnetic signal 2202 may be determined based at least in part upon the feedback signal 2212. Examples of sensors are described in, U.S. Pat. No. 6,935,165, and U.S. Patent Publication 2004/0007051, both of which are incorporated herein by reference. Osmotic pump device 2204 includes remotely activatable control element 2124. Feedback signal 2212 may be transmitted wirelessly back to remote controller 2200. Remote controller 2200 may include electrical circuitry 2214, signal generator 2216, signal transmitter 2218, and memory 2220. Signal generator 2216 may be capable of producing an electromagnetic signal that includes a static or quasi-static magnetic field, a static or quasi-static electrical field, non-ionizing electromagnetic radiation, radio-frequency electromagnetic radiation, microwave electromagnetic radiation, millimeter wave electromagnetic radiation, optical electromagnetic radiation, or ultraviolet electromagnetic radiation.

Figure 44:
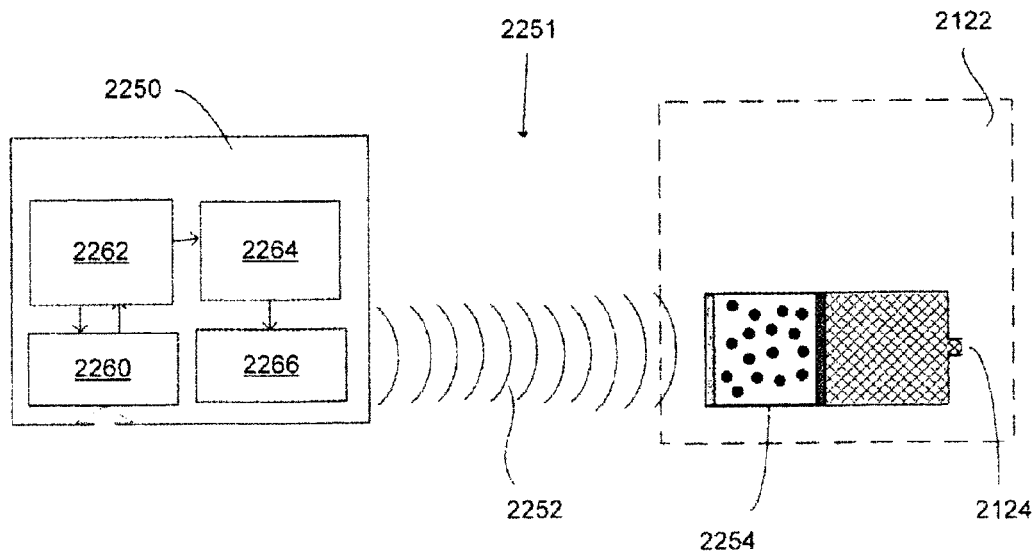
FIG. 44 depicts an embodiment of a system including a remote control device and an osmotic pump device.

As illustrated in FIG. 44, in some embodiments of osmotic pump systems, the remote controller may be configured to receive user input of control parameters. Remote controller 2250 includes input 2260 for receiving input of information or instructions from a user such as, for example, commands, variables, durations, amplitudes, frequencies, waveforms, data storage or retrieval instructions, patient data, etc. As in the other embodiments, remote controller 2250 transmits electromagnetic control signal 2252 to osmotic pump device 2254 in environment 2122, where it activates remotely activatable control element 2124. Input 2260 may include one or more input devices such as a keyboard, keypad, microphone, mouse, etc. for direct input of information from a user, or input 2260 may be any of various types of analog or digital data inputs or ports, including data read devices such as disk drives, memory device readers, and so forth in order to receive information or data in digital or electronic form. Data or instructions entered via input 2260 may be used by electrical circuitry 2262 to modify the operation of remote controller 2250 to modulate generation of an electromagnetic control signal 2252 by signal generator 2264 and transmission of the control signal 2252 by transmitter 2266.

Figure 45:
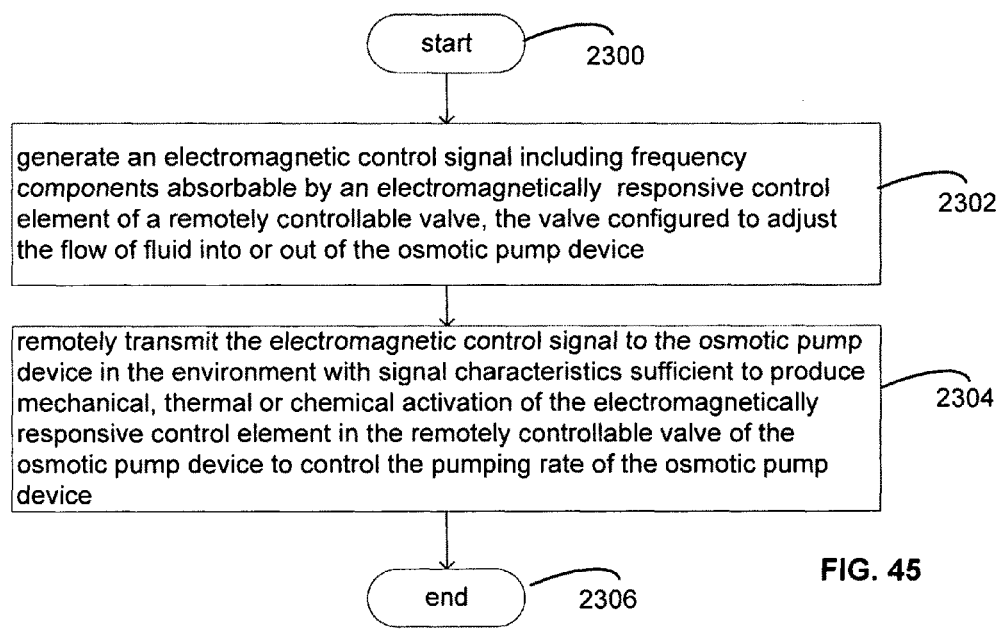
FIG. 45 is a flow diagram of an embodiment of a method of controlling an osmotic pump device.

A method of controlling an osmotic pump device is shown in FIG. 45. The method of controlling the osmotic pump device includes generating an electromagnetic control signal including frequency components absorbable by an electromagnetically responsive control element of a remotely controllable valve, the valve configured to adjust the flow of fluid into or out of the osmotic pump device at step 2302 and remotely transmitting the electromagnetic control signal to the osmotic pump device in the environment with signal characteristics sufficient to produce mechanical, thermal or chemical activation of the electromagnetically responsive control element in the remotely controllable valve of the osmotic pump device to control the pumping rate of the osmotic pump device at step 2304. The method may include generating and transmitting the electromagnetic control signal with a remote control signal source. The electromagnetic control signal may be generated from a model-based calculation or from a stored pattern.

Figure 46:
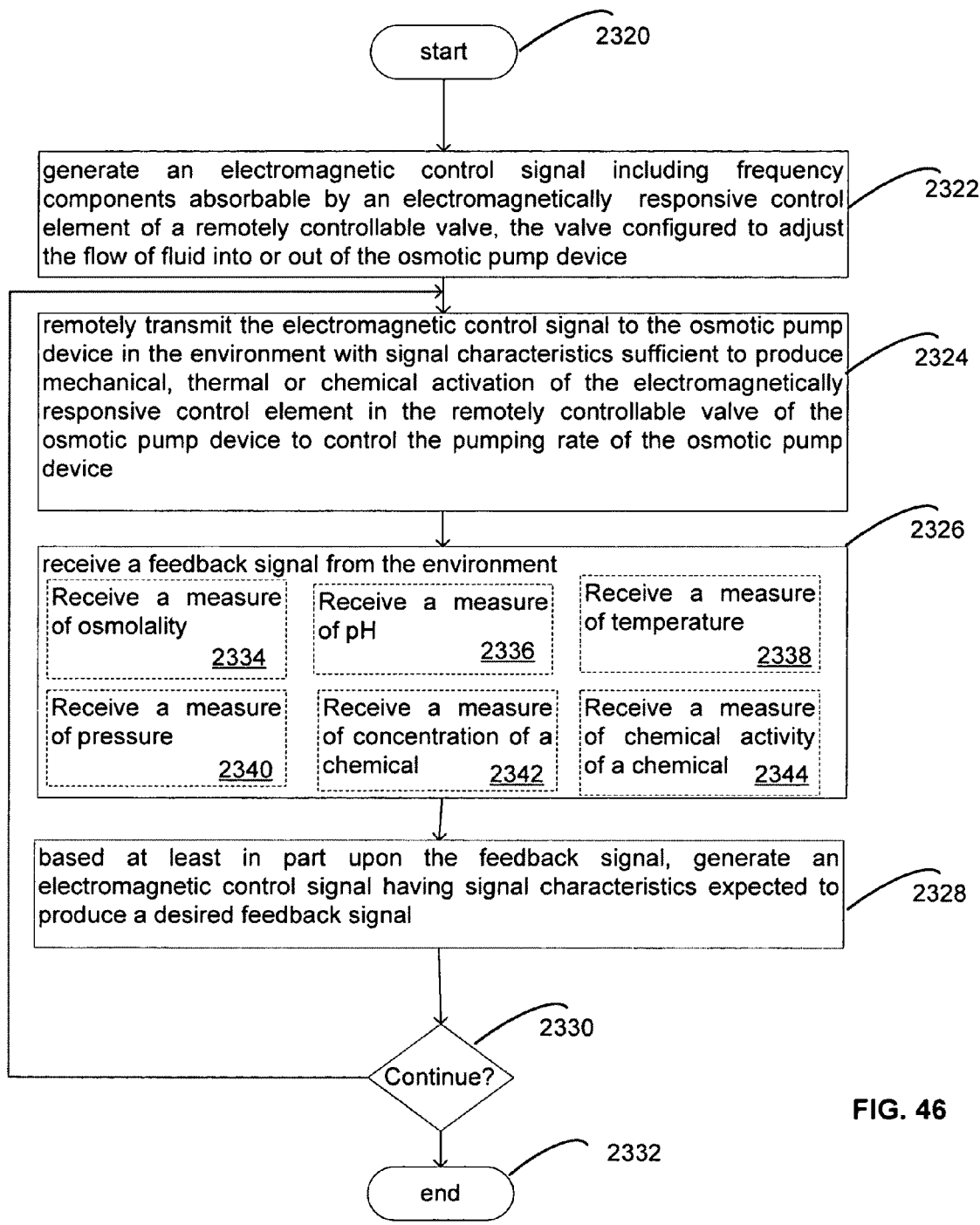
FIG. 46 is a flow diagram of an embodiment of a method of controlling an osmotic pump device.

As shown in FIG. 46, the method of controlling the osmotic pump device may include generating an electromagnetic control signal including frequency components absorbable by an electromagnetically responsive control element of a remotely controllable valve, the valve configured to adjust the flow of fluid into or out of the osmotic pump device at step 2322, remotely transmitting the electromagnetic control signal to the osmotic pump device in the environment with signal characteristics sufficient to produce mechanical, thermal or chemical activation of the electromagnetically responsive control element in the remotely controllable valve of the osmotic pump device to control the pumping rate of the osmotic pump device at step 2324, receiving a feedback signal from the environment at step 2326, and based at least in part upon the feedback signal, generating an electromagnetic control signal having signal characteristics expected to produce a desired feedback signal at step 2328. The process may repeat until a decision to quit is made at decision point 2330. Receiving a feedback signal from the environment may include receiving a measure of osmolality, as shown at step 2334, pH as shown at step 2336, temperature as shown at step 2338, pressure as shown at step 2340, or concentration or chemical activity of a chemical within at least a portion of the environment as shown at steps 2342 and 2344, respectively.

Figure 47:
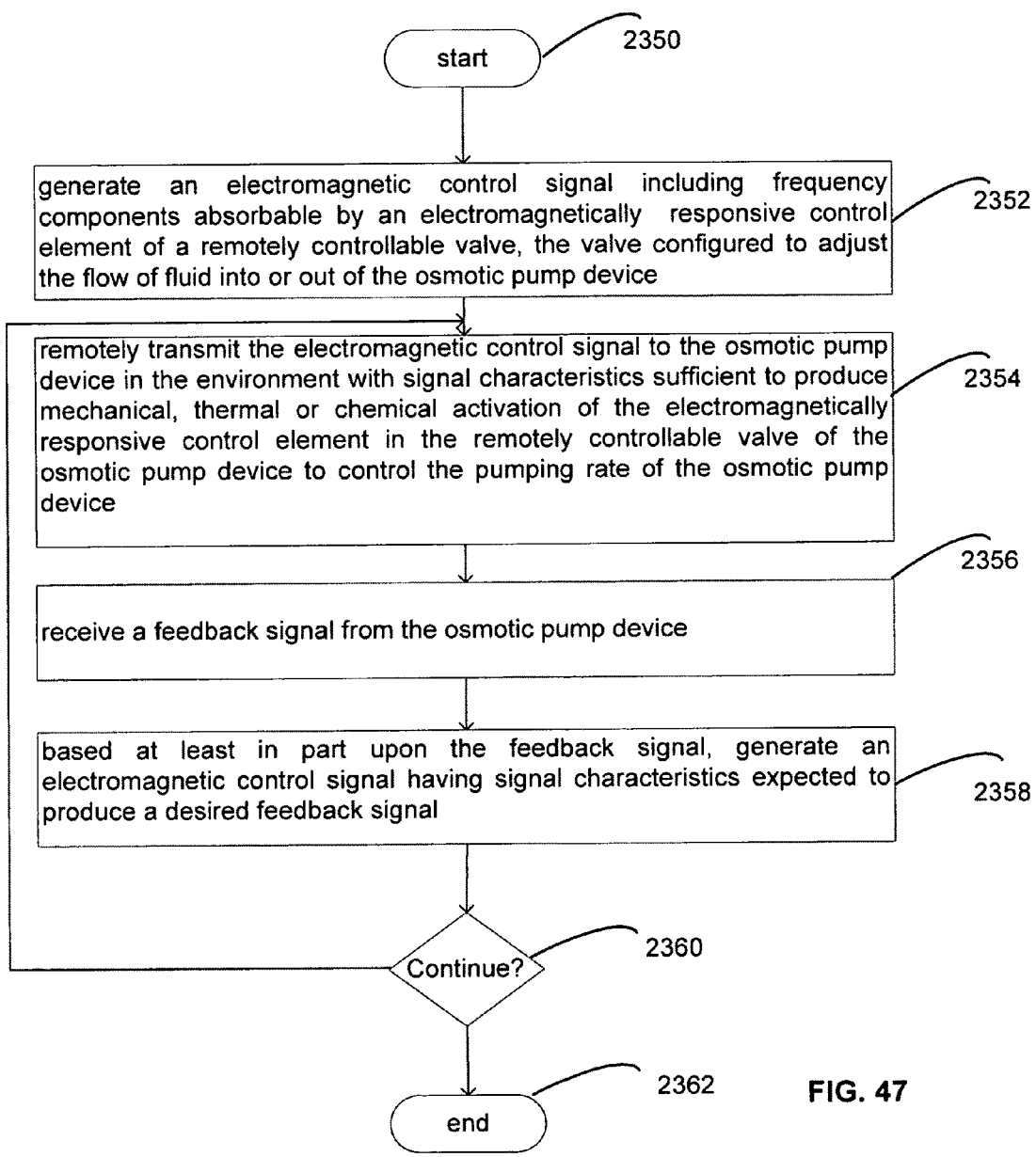
FIG. 47 is a flow diagram of an embodiment of a method of controlling an osmotic pump device.

In some embodiments, as shown in FIG. 47, the method of controlling the osmotic pump device may include generating an electromagnetic control signal including frequency components absorbable by an electromagnetically responsive control element of a remotely controllable valve, the valve configured to adjust the flow of fluid into or out of the osmotic pump device at step 2352 and remotely transmitting the electromagnetic control signal to the osmotic pump device in the environment with signal characteristics sufficient to produce mechanical, thermal or chemical activation of the electromagnetically responsive control element in the remotely controllable valve of the osmotic pump device to control the pumping rate of the osmotic pump device at step 2354. The method may also include receiving a feedback signal from the osmotic pump device at step 2356, and based at least in part upon the feedback signal, generating an electromagnetic control signal having signal characteristics expected to produce a desired feedback signal at step 2358. The process may repeat until a decision to quit is made at decision point 2360. Receiving a feedback signal from the osmotic pump device may include receiving a signal representing a concentration of an osmotic pressure-generating material in an osmotic fluid within the osmotic pump device.

Figure 48:
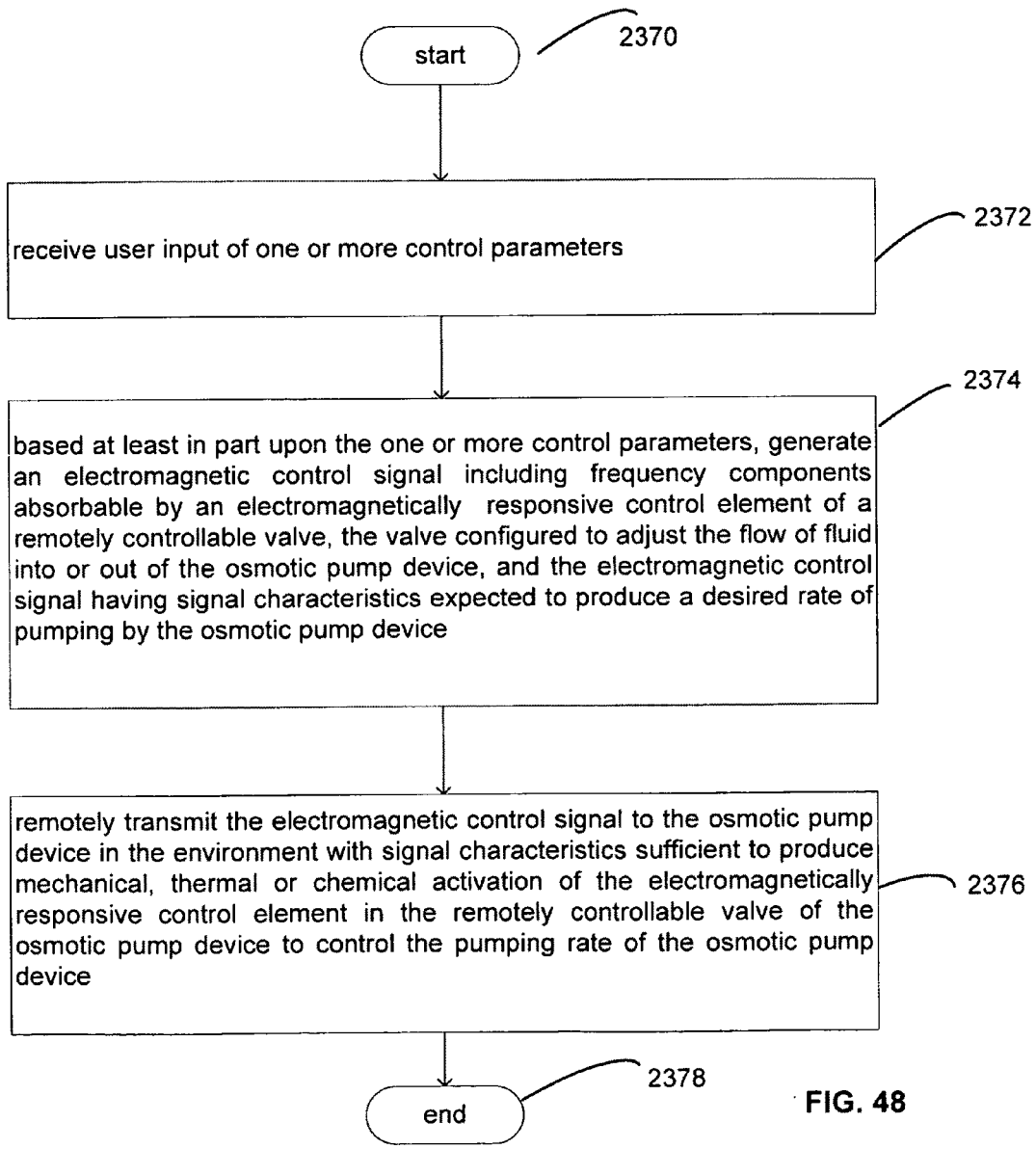
FIG. 48 is a flow diagram of an embodiment of a method of controlling an osmotic pump device.

In some embodiments, as shown in FIG. 48, a method of controlling the osmotic pump device may include receiving user input of one or more control parameters at step 2372. Step 2374 includes, based at least in part upon the one or more control parameters, generating an electromagnetic control signal including signal frequency components absorbable by an electromagnetically responsive control element of a remotely controllable valve, the valve configured to adjust the flow of fluid into or out of the osmotic pump device, and the electromagnetic control signal having signal characteristics expected to produce a desired rate of pumping by the osmotic pump device. Step 2376 includes remotely transmitting the electromagnetic control signal to the osmotic pump device in the environment with signal characteristics sufficient to produce mechanical, thermal, or chemical activation of the electromagnetically responsive control element in the remotely controllable valve of the osmotic pump device to control the pumping rate of the osmotic pump device.

In any or all of the embodiments, the method may include activating the electromagnetically responsive control element to produce heating or cooling, wherein the heating or cooling modifies flow rate of fluid through the remotely controllable valve, or activating the electromagnetically responsive control element to produce a change in configuration of the electromagnetically responsive control element, wherein the change in configuration modifies the flow rate of fluid through the remotely controllable valve.

The steps of generating an electromagnetic control signal and remotely transmitting the electromagnetic control signal to the osmotic pump device may be performed according to instructions provided in the form of software, hardware or firmware. Software for controlling the osmotic pump device may include instructions for generating an electromagnetic control signal including frequency components absorbable by an electromagnetically responsive control element of a remotely controllable valve, the valve configured to adjust the flow of fluid into or out of the osmotic pump device, and instructions for remotely transmitting the electromagnetic control signal to the osmotic pump device in the environment with signal characteristics sufficient to produce mechanical, thermal or chemical activation of the electromagnetically responsive control element in the remotely controllable valve of the osmotic pump device to control the pumping rate of the osmotic pump device.

The software instructions for generating an electromagnetic control signal may include instructions for calculating the electromagnetic control signal based on a model, or instructions for generating the electromagnetic control signal based on a pattern stored in a data storage location. The software may include instructions for receiving a feedback signal from the environment, and instructions for generating the electromagnetic control signal based at least in part upon the received feedback signal, the electromagnetic control signal having signal characteristics expected to produce a desired feedback signal. Alternatively, or in addition, the software may include instructions for receiving a feedback signal from the osmotic pump device and instructions for generating the electromagnetic control signal based upon at least in part on the received feedback signal, the electromagnetic control signal having frequency composition and amplitude expected to produce a desired feedback signal. In some embodiments, the software may include instructions for receiving user input of one or more control parameters and instructions for generating the electromagnetic control signal based at least in part upon the one or more control parameters.

Figure 49:
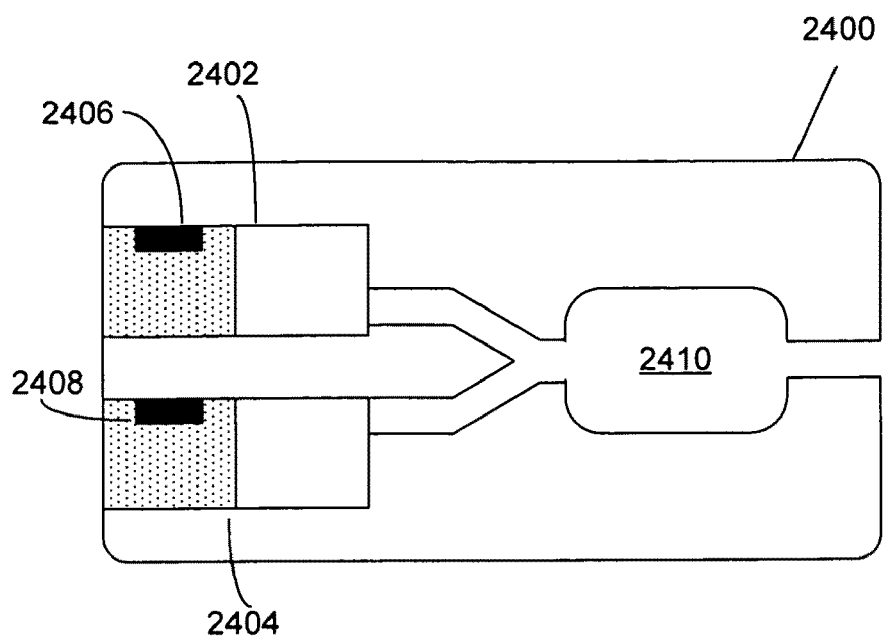
FIG. 49 depicts an embodiment of an osmotic pump device including two osmotic pumps operating in parallel.

Osmotic pump devices as described herein may include one or multiple remotely activatable control elements. In devices that include multiple remotely activatable control elements, the multiple remotely activatable control elements may all be of the same type, or may be of different types. Multiple remotely activatable control elements may be activated or controlled in parallel as exemplified in FIG. 49, or in series as exemplified in FIG. 50. In FIG. 49, osmotic pump device 2400 includes first osmotic pump 2402 and second osmotic pump 2404. Osmotic pumps 2402 and 2404 are regulated by remotely activatable control elements 2406 and 2408, respectively. Osmotic pumps 2402 and 2404 may be operated in parallel to pump two reactant fluids into chamber 2410, which may be a reaction chamber in which the reactant fluids react prior to release into the environment.

Figure 50:
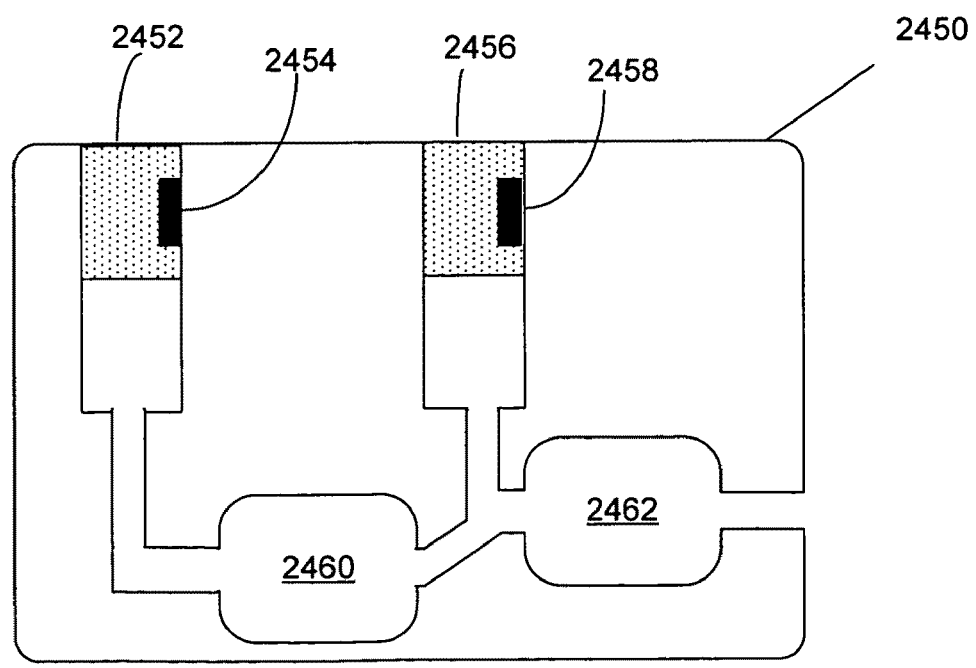
FIG. 50 depicts an embodiment of an osmotic pump device including two osmotic pumps operating in series.

In FIG. 50, osmotic pump device 2450 includes first osmotic pump 2452 controlled by first remotely activatable control element 2454, and second osmotic pump 2456 controlled by second remotely activatable control element 2458. First osmotic pump 2452 may pump a fluid into a reaction chamber 2460 to react with a reactant already present in reaction chamber 2460, for example, and subsequently into chamber 2462, where it may react with fluid pumped into chamber 2462 by second osmotic pump 2456. The osmotic pump systems depicted in FIGS. 49 and 50 are merely exemplary of a large variety of systems that may be constructed including remotely activatable osmotic pumps.

Figure 51:
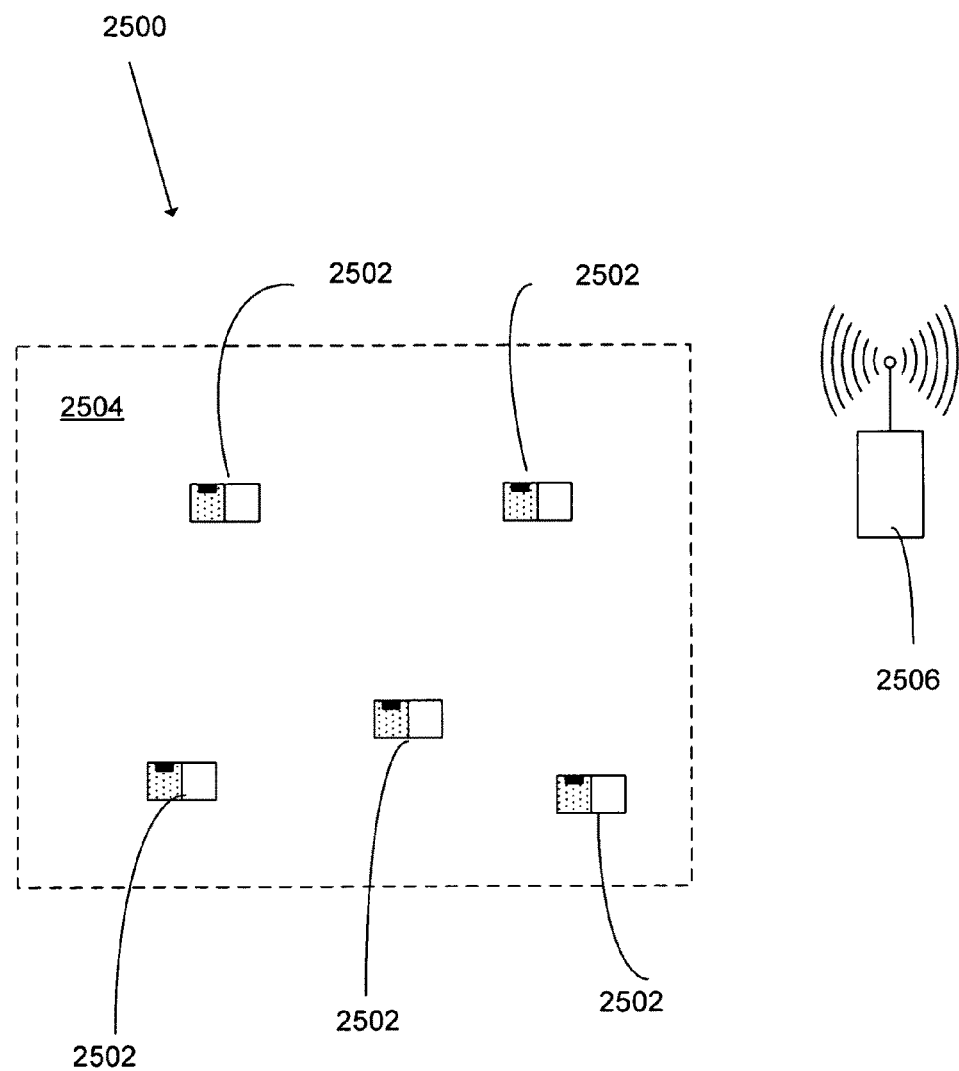
FIG. 51 depicts an embodiment of an osmotic pump system including multiple osmotic pump devices.

Selective activation or control of remotely activatable control elements may be achieved by configuring remotely activatable control elements to be activated by electromagnetic control signals having particular signal characteristics, which may include, for example, particular frequency, phase, amplitude, temporal profile, polarization, and/or directional characteristics, and spatial variations thereof. For example, different control elements may be responsive to different frequency components of a control signal, thereby allowing selective activation of the different control elements. An osmotic pump device may include multiple selectively activatable control elements, each associated with a particular fluid handling element, which may thus be controlled to perform multiple fluid-handling or reaction steps in a particular sequence. It is also contemplated that an osmotic pump system may include multiple osmotic pump devices which may be of the same or different types. As shown in FIG. 51, an osmotic pump system 2500 may include multiple identical osmotic pump devices 2502 distributed throughout an environment 2504 in order to perform a particular chemical reaction or process at multiple locations within the environment, and controlled by a remote controller 2506. Alternatively, an osmotic pump system may include multiple different osmotic pump devices at different locations within an environment, each performing or controlling a reaction suited for the particular location. The invention as described herein is not limited to devices or systems including any specific number or configuration of remotely activatable control elements within an osmotic pump device, or specific number or configuration of osmotic pump devices or remote controllers within an osmotic pump system. Depending upon the particular application of a system, remotely activatable control elements and/or osmotic pump devices may be controlled in a particular pattern to producing a desired distribution of a delivery material in an environment. Control of such systems may be performed with the use of suitable hardware, firmware, or software, through one or multiple remote controllers.

With regard to the hardware and/or software used in the control of osmotic pump devices and systems according to the present embodiments, and particularly to the sensing, analysis, and control aspects of such systems, those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency or implementation convenience tradeoffs. Those having skill in the art will appreciate that there are various vehicles by which processes and/or systems described herein can be effected (e.g., hardware, software, and/or firmware), and that the preferred vehicle will vary with the context in which the processes are deployed. For example, if an implementer determines that speed and accuracy are paramount, the implementer may opt for a hardware and/or firmware vehicle; alternatively, if flexibility is paramount, the implementer may opt for a solely software implementation; or, yet again alternatively, the implementer may opt for some combination of hardware, software, and/or firmware. Hence, there are several possible vehicles by which the processes described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be implicitly understood by those with skill in the art that each function and/or operation within such block diagrams, flowcharts, or examples can be implemented, individually and/or collectively, by a wide range of hardware, software, firmware, or virtually any combination thereof. In one embodiment, several portions of the subject matter subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in standard integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the capabilities of one of skill in the art in light of this disclosure. In addition, those skilled in the art will appreciate that certain mechanisms of the subject matter described herein are capable of being distributed as a program product in a variety of forms, and that an illustrative embodiment of the subject matter described herein applies equally regardless of the particular type of signal bearing media used to actually carry out the distribution. Examples of a signal bearing media include, but are not limited to, the following: recordable type media such as floppy disks, hard disk drives, CD ROMs, digital tape, and computer memory; and transmission type media such as digital and analog communication links using TDM or IP based communication links (e.g., links carrying packetized data).

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment).

Those skilled in the art will recognize that it is common within the art to describe devices for detection or sensing, signal processing, and device control in the fashion set forth herein, and thereafter use standard engineering practices to integrate such described devices and/or processes into osmotic pump systems as exemplified herein. That is, at least a portion of the devices and/or processes described herein can be integrated into an osmotic pump system via a reasonable amount of experimentation.

Those having skill in the art will recognize that systems as described herein may include one or more of a memory such as volatile and non-volatile memory, processors such as microprocessors and digital signal processors, computational-supporting or -associated entities such as operating systems, user interfaces, drivers, sensors, actuators, applications programs, one or more interaction devices, such as data ports, control systems including feedback loops and control implementing actuators (e.g., devices for sensing osmolality, pH, pressure, temperature, or chemical concentration, signal generators for generating electromagnetic control signals). A system may be implemented utilizing any suitable available components, combined with standard engineering practices.

The foregoing-described aspects depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermediate components. Likewise, any two components so associated can also be viewed as being "operably connected", or "operably coupled", to each other to achieve the desired functionality.

While particular aspects of the present subject matter described herein have been shown and described, it will be obvious to those skilled in the art that, based upon the teachings herein, changes and modifications may be made without departing from this subject matter described herein and its broader aspects and, therefore, the appended claims are to encompass within their scope all such changes and modifications as are within the true spirit and scope of this subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should NOT be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" and/or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense of one having skill in the art would understand the convention (e.g., "a system having at least one of A, B, and C" would include but not be limited to systems that have A alone, B alone, C alone, A and B together, A and C together, B and C together, and/or A, B, and C together). In those instances where a convention analogous to "at least one of A, B, or C, etc." is used, in general such a construction is intended in the sense of one having skill in the art would understand the convention (e.g., "a system having at least one of A, B, or C" would include but not be limited to systems that have A alone, B alone, C alone, A and B together, A and C together, B and C together, and/or A, B, and C together).

Although the methods, devices, systems and approaches herein have been described with reference to certain preferred embodiments, other embodiments are possible. As illustrated by the foregoing examples, various choices of remote controller, system configuration and osmotic pump device may be within the scope of the invention. As has been discussed, the choice of system configuration may depend on the intended application of the system, the environment in which the system is used, cost, personal preference or other factors. System design, manufacture, and control processes may be modified to take into account choices of use environment and intended application, and such modifications, as known to those of skill in the arts device design and construction, may fall within the scope of the invention. Therefore, the full spirit or scope of the invention is defined by the appended claims and is not to be limited to the specific embodiments described herein.

The invention claimed is:

1. A system comprising:
a signal-bearing medium bearing one or more instructions related to controlling an osmotic pump device, the one or more instructions including:
  instructions for generating an electromagnetic control signal including frequency components absorbable by an electromagnetically responsive control element of a remotely controllable valve, the valve configured to adjust the movement of fluid into or out of the osmotic pump device; and
  instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device.

2. The system of claim 1, wherein the instructions for generating an electromagnetic control signal include instructions for calculating the electromagnetic control signal based on a model.

3. The system of claim 1, wherein the instructions for generating an electromagnetic control signal include instructions for generating the electromagnetic control signal based on a pattern stored in a data storage location.

4. The system of claim 1, wherein the one or more instructions include:
  instructions for receiving a feedback signal from the environment; and
  instructions for generating the electromagnetic control signal based at least in part upon the received feedback signal, the electromagnetic control signal having signal characteristics expected to produce a desired feedback signal.

5. The system of claim 1, wherein the one or more instructions include:
  instructions for receiving a feedback signal from the osmotic pump device; and
  instructions for generating the electromagnetic control signal based at least in part upon the received feedback signal, the electromagnetic control signal having frequency composition and amplitude expected to produce a desired feedback signal.

6. The system of claim 1, wherein the one or more instructions include:
  instructions for receiving user input of one or more control parameters; and
  instructions for generating the electromagnetic control signal based at least in part upon the one or more control parameters.

7. The system of claim 1, wherein the instructions for generating an electromagnetic control signal including frequency components absorbable by an electromagnetically responsive control element of a remotely controllable valve include instructions for generating a radio frequency electromagnetic control signal.

8. The system of claim 1, wherein the instructions for generating an electromagnetic control signal including frequency components absorbable by an electromagnetically responsive control element of a remotely controllable valve include instructions for generating a microwave frequency electromagnetic control signal.

9. The system of claim 1, wherein the instructions for generating an electromagnetic control signal including frequency components absorbable by an electromagnetically responsive control element of a remotely controllable valve include instructions for generating an infrared electromagnetic control signal.

10. The system of claim 1, wherein the instructions for generating an electromagnetic control signal including frequency components absorbable by an electromagnetically responsive control element of a remotely controllable valve include instructions for generating a millimeter wave electromagnetic control signal.

11. The system of claim 1, wherein the instructions for generating an electromagnetic control signal including frequency components absorbable by an electromagnetically responsive control element of a remotely controllable valve include instructions for generating an optical control signal.

12. The system of claim 1, wherein the instructions for generating an electromagnetic control signal including frequency components absorbable by an electromagnetically responsive control element of a remotely controllable valve include instructions for generating an ultraviolet control signal.

13. The system of claim 1, wherein the instructions for generating an electromagnetic control signal including frequency components absorbable by an electromagnetically responsive control element of a remotely controllable valve include instructions for generating an electromagnetic control signal including frequency components absorbable by an electromagnetically responsive control element including an expandable gel structure.

14. The system of claim 1, wherein the instructions for generating an electromagnetic control signal including frequency components absorbable by an electromagnetically responsive control element of a remotely controllable valve include instructions for generating an electromagnetic control signal including frequency components absorbable by an electromagnetically responsive control element including a bimetallic structure.

15. The system of claim 1, wherein the instructions for generating an electromagnetic control signal including frequency components absorbable by an electromagnetically responsive control element of a remotely controllable valve include instructions for generating an electromagnetic control signal including frequency components absorbable by an electromagnetically responsive control element including a shape memory metal.

16. The system of claim 1, wherein the instructions for generating an electromagnetic control signal including frequency components absorbable by an electromagnetically responsive control element of a remotely controllable valve include instructions for generating an electromagnetic control signal including frequency components absorbable by an electromagnetically responsive control element including a shape memory polymer.

17. The system of claim 1, wherein the instructions for generating an electromagnetic control signal including frequency components absorbable by an electromagnetically responsive control element of a remotely controllable valve include instructions for generating an electromagnetic control signal including frequency components absorbable by an electromagnetically responsive control element including a ferroelectric material.

18. The system of claim 1, wherein the signal-bearing medium includes a CD-ROM.

19. The system of claim 1, wherein the signal-bearing medium includes a computer memory.

20. The system of claim 1, wherein the signal-bearing medium includes a transmission medium.

21. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal characteristics sufficient to produce heating of the electromagnetically responsive control element.

22. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal characteristics sufficient to produce expansion of the electromagnetically responsive control element.

23. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal characteristics sufficient to produce change in shape of the electromagnetically responsive control element.

24. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal characteristics sufficient to produce change in configuration of the electromagnetically responsive control element.

25. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal amplitude sufficient to produce mechanical, thermal or chemical activation of the electromagnetically responsive control element.

26. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal waveform sufficient to produce mechanical, thermal or chemical activation of the electromagnetically responsive control element.

27. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal polarization sufficient to produce mechanical, thermal or chemical activation of the electromagnetically responsive control element.

28. The system of claim 1, wherein the instructions for remotely transmitting the electromagnetic control signal to the osmotic pump device in an environment with signal characteristics sufficient to produce mechanical, thermal or chemical activation of the electromagnetically responsive control element in the remotely controllable valve of the osmotic pump device to control the pumping rate of the osmotic pump device, include instructions for remotely transmitting the electromagnetic control signal with signal duration sufficient to produce mechanical, thermal or chemical activation of the electromagnetically responsive control element.

* * * * *